US011111311B2

(12) United States Patent
Yoshida et al.

(10) Patent No.: US 11,111,311 B2
(45) Date of Patent: *Sep. 7, 2021

(54) ANTI-DLL3 ANTIBODY

(71) Applicants: CHUGAI SEIYAKU KABUSHIKI KAISHA, Tokyo (JP); THE UNIVERSITY OF TOKYO, Tokyo (JP)

(72) Inventors: Kenji Yoshida, Meguro-ku (JP); Hiroyuki Aburatani, Bunkyo-ku (JP); Shumpei Ishikawa, Bunkyo-ku (JP)

(73) Assignees: CHUGAI SEIYAKU KABUSHIKI KAISHA, Tokyo (JP); THE UNIVERSITY OF TOKYO, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/846,135

(22) Filed: Sep. 4, 2015

(65) Prior Publication Data

US 2015/0368355 A1 Dec. 24, 2015
US 2016/0244530 A2 Aug. 25, 2016

Related U.S. Application Data

(63) Continuation of application No. 13/575,861, filed as application No. PCT/JP2011/000485 on Jan. 28, 2011, now Pat. No. 9,127,071.

(30) Foreign Application Priority Data

Jan. 29, 2010 (JP) .............................. JP2010-019391

(51) Int. Cl.
C07K 16/30 (2006.01)
C07K 16/28 (2006.01)
A61K 39/395 (2006.01)
A61K 39/00 (2006.01)
C12Q 1/6886 (2018.01)
G01N 33/574 (2006.01)

(52) U.S. Cl.
CPC ........ *C07K 16/3023* (2013.01); *A61K 39/395* (2013.01); *C07K 16/28* (2013.01); *C12Q 1/6886* (2013.01); *G01N 33/574* (2013.01); *A61K 2039/505* (2013.01); *C07K 2317/24* (2013.01); *C07K 2317/30* (2013.01); *C07K 2317/732* (2013.01); *C07K 2317/77* (2013.01); *C07K 2319/30* (2013.01); *C12Q 2600/118* (2013.01); *G01N 2333/4703* (2013.01)

(58) Field of Classification Search
CPC ........ A61K 47/48592; A61K 47/48384; A61K 47/48507
See application file for complete search history.

(56) References Cited

U.S. PATENT DOCUMENTS

2007/0141066 A1 6/2007 Phillips et al.
2012/0328624 A1 12/2012 Yoshida et al.

FOREIGN PATENT DOCUMENTS

| EP | 2 078 731 A1 | 7/2009 |
|---|---|---|
| EP | 2817338 B1 | 7/2017 |
| JP | H11299493 A | 11/1999 |
| JP | 2008273973 A | 11/2008 |
| JP | 2009523709 A | 6/2009 |
| WO | 00/47602 | 8/2000 |
| WO | 01/12664 A2 | 2/2001 |
| WO | 01/075067 A3 | 10/2001 |
| WO | 02/14358 A2 | 2/2002 |
| WO | 03/025138 A2 | 3/2003 |
| WO | 04/030615 A2 | 4/2004 |
| WO | 2004/053102 A2 | 6/2004 |
| WO | 2005/077090 A2 | 8/2005 |
| WO | 2007/080597 A2 | 7/2007 |
| WO | 2007/111733 A2 | 10/2007 |
| WO | 2008/047925 A1 | 4/2008 |
| WO | 2009/124931 A2 | 10/2009 |
| WO | 2011/093097 A1 | 8/2011 |
| WO | 2013/126746 A2 | 8/2013 |
| WO | 2015/127407 A1 | 8/2015 |
| WO | 2017/021349 A1 | 2/2017 |

OTHER PUBLICATIONS

Lloyd et al. Protein Engineering, Design & Selection 2009, 22:159-168 (Year: 2009).*
Edwards et al., J Mol Biol. Nov. 14, 2003;334(1):103-118 (Year: 2003).*
Ayyakannu Ayyanan et al., "Increased Wnt signaling triggers oncogenic conversion of human breast epithelial cells by a Notch-dependent mechanism", Proceedings of the National Academy of Sciences of USA, 2006, pp. 3799-3804, vol. 103, No. 10.
Communication dated Mar. 24, 2015, issued by the Japanese Patent Office in counterpart Application No. 2011551775.
Communication for EP 11736812.6 dated Jun. 6, 2013, along with Supplementary European Search Report dated May 29, 2013.
Ena Ladi et al., "The divergent DSL ligand Dll3 does not activate Notch signaling but cell autonomously attenuates signaling induced by other DSL ligands", The Journal of Cell Biology, 2005, pp. 983-992, vol. 170, No. 6.

(Continued)

*Primary Examiner* — Daniel C Gamett
(74) *Attorney, Agent, or Firm* — Sughrue Mion, PLLC

(57) ABSTRACT

It is intended to disclose an antibody which binds to DLL3 protein. Preferably, the antibody of the present invention recognizes a region from amino acids 216 to 492 in human DLL3 having the amino acid sequence as set forth in SEQ ID NO: 1. The present invention also provides a pharmaceutical composition, for example, an anticancer agent, comprising the antibody of the present invention as an active ingredient. The present invention further discloses a method for diagnosing cancer using the antibody of the present invention and a diagnostic drug for cancer comprising the antibody of the present invention.

17 Claims, 12 Drawing Sheets

Specification includes a Sequence Listing.

(56) References Cited

OTHER PUBLICATIONS

Heidi S. Phillips et al., "Molecular subclasses of high-grade glioma predict prognosis, delineate a pattern of disease progression, and resemble stages in neurogenesis", Cancer Cell, 2006, pp. 157-173, vol. 9.
Insa Geffers et al., "Divergent functions and distinct localization of the Notch ligands DLL1 and DLL3 in vivo", The Journal of Cell Biology, 2007, pp. 465-476, vol. 178, No. 3.
International Preliminary Report on Patentability for International Application No. PCT/JP2011/000485, dated Sep. 27, 2012.
International Search Report for PCT/JP2011/000485 dated Mar. 1, 2011.
Jiang et al, "Achaete-Scute Complex Homologue 1 Regulates Tumor-Initiating Capacity in Human Small Cell Lung Cancer", Cancer Research, 69(3):845-854 (2009), Abstract No. XP002697824.
Kenya Shitara, "Potelligent Antibodies as Next Generation Therapeutic Antibodies", Yakugaku Zasshi, 2009, pp. 3-9, vol. 129, No. 1.
Michael E. Mullendore et al., "Ligand-dependent Notch Signaling Is Involved in Tumor Initiation and Tumor Maintenance in Pancreatic Cancer", Clin Cancer Res, 2009, pp. 2291-2301, vol. 15.
Michael P. Bulman et al., "Mutations in the human Delta homologue, DLL3, cause axial skeletal defects in spondylocostal dysostosis", Nature Genetics, 2000, pp. 438-441, vol. 24.
Millipore: "Anti-Delta3, clone 1E7.2", Internet citation, Abstract No. XP002697359, pp. 1-3 (Jul. 15, 2008).
P D Turnpenny et al., "Novel mutations in DLL3, a somitogenesis gene encoding a ligand for the Notch signaling pathway, cause a consistent pattern of abnormal vertebral segmentation in spondylcostal dysostosis", J Med Genet, 2003, pp. 333-339, vol. 40.
R&D Systems: "Human DLL3 Antibody", Monoclonal Mouse IgG2B Clone #378703, Catalog No. MAB4315, Internet Citation, Abstract No. XP002697358 (May 20, 2010).
De Pascalis et al. The Journal of Immunology (2002) 169, 3076-3084.
Lamminmaki et al. (JBC 2001, 276:36687-36694).
Padlan et al. (PNAS 1989, 86:5938-5942).
Song et al. (Biochem Biophys Res Comm 268:390-394 (2000)).
Kumar et al. (J. Biol. Chem. 275:35129-35136 (2000)).
Smith-Gill et al. (J. Immunol. 139:4135-4144 (1987)).
Ward et al. (Nature 341:544-546 (1989)).
Holm et al. ((2007) Mol. Immunol. 44: 1075-1084).
Vajdos et al. ((2002) J. Mol. Biol. 320, 415-428).
Casset et al. ((2003) BBRC 307, 198-205).
MacCallum et al. (J. Mol. Biol. (1996) 262:732-745).
Rudikoff et al. (Proc Natl Acad Sci USA 1982 vol. 79 p. 1979-1983).
Communication, dated Jan. 30, 2019, issued by the European Patent Office in counterpart Application No. 11736812.6.
Communication, dated Jan. 8, 2019, issued by the European Patent Office in counterpart Application No. 11736812.6.
Communication, dated Jan. 15, 2019, issued by the European Patent Office in counterpart Application No. 11736812.6.
"Monoclonal Anti-human DLL3 Antibody", Product sheet for Human DLL3 Antibody, MAB4315, R&D Systems, Inc., 2007.
"Immunoglobulin G" Immunoglobulin G, Review InvivoGen, 2011.
Nimmerjahn, Falk et al., "Fcγ Receptors Old Friends and New Family Members" Immunity, 2006, pp. 19-28, vol. 24, pp.
Stockwin, LH et al., "Antibodies as therapeutic agents: vive la renaissance!", Expert Opinion on Biological Therapy, 2003, vol. 3; No. 7, pp. 1133-1152.
Shields, Robert L. et al., "High Resolution Mapping of the Binding Site on Human IgG1 for FcγRI, FcγRII, FcγRIII, and FcRn and Design of IgG1 Variants with Improved Binding to the FcγR", The Journal of Biological Chemistry, 2001, vol. 276, No. 9 pp. 6591-6604.
Zanetti, M et al., "The Antibodies," Harwood Academic Publishers, 2000, vol. 6 pp. 36-37.
Goding, James W. et al., "Monoclonal Antibodies: Principles and Practice", Academic Press, 1996, Third Edition, pp. 134-135.
Carter, Paul et al., "Identification and validation of cell surface antigens for antibody targeting in oncology", Endocrine-Related Cancer, 2004, vol. 11, pp. 659-687.
Carter, Paul J. et al., "Antibody-Drug Conjugates for Cancer Therapy", The Cancer Journal, 2008, vol. 14, No. 3, pp. 154-169.
Adams, Gregory P et al., "Monoclonal antibody therapy of cancer", Nature Biotechnology, 2005, vol. 23, No. 9, pp. 1147-1157.
Sun, Yu et al., "Antibody-drug conjugates as targeted cancer therapeutics", Acta Pharmaceutica Sinica, 2009, vol. 44, No. 9, pp. 943-952.
Chen, Jin et al., "Antibody-cytotoxic agent conjugates for cancer therapy", Expert Opinion on Drug Delivery, 2005, vol. 2, No. 5, pp. 873-890.
Grant, Stefan C. et al., "Targeting of small-cell lung cancer using the anti-GD2 ganglioside monoclonal antibody 3F8: a pilot trial", European Journal of Nuclear Medicine, 1996; vol. 23, No. 2, pp. 145-149.
Dunwoodie, Sally L, "The role of Notch in patterning the human vertebral column", Current Opinion in Genetics & Development, 2009, vol. 19, pp. 329-337.
D'Souza, B. et al., "The many facets of Notch ligands", Oncogene, 2008, vol. 27, pp. 5148-5167.
Henke, R. Michael et al., "Ascl1 and Neurog2 Form Novel Complexes and Regulate *Delta-like3* (Dll3) Expression in the Neural Tube", Dev Biol., 2009, vol. 328, No. 2, pp. 529-540.
Ball. Douglas W., "Achaete—scute homolog-1 and Notch in lung neuroendocrine development and cancer", Cancer Letters, 2004, vol. 204, pp. 159-169.
Choi, Kuicheon, et al., "Distinct Biological Roles for the Notch Ligands Jagged-1 and Jagged-2", The Journal of Biological Chemistry, 2009, vol. 284, No. 26, pp. 17766-17774.
"Compugen Announces Discovery of Blood Based Biomarker for Diagnosis of Lung Cancer", Apr. 29, 2008 (2 pages), retrieved from https://www.cgen.com/mediacenter/compugen-announces-discovery-of-blood-based-biomarker-for-diagnosis-of-lung-cancer.
Taneja, Tarvinder K., et al., "Markers of small cell lung cancer", World Journal of Surgical Oncology, 2004, vol. 2, No. 10, pp. 1-5.
Chung, Shan et al., "Characterization of in vitro antibody-dependent cell-mediated cytotoxicity activity of therapeutic antibodies—Impact of effector cells", Journal of Immunological Methods, 2014, vol. 407, pp. 63-75.
Weng, Wen-Kai et al., "Two Immunoglobulin G Fragment C Receptor Polymorphisms Independently Predict Response to Rituximab in Patients With Follicular Lymphoma", Journal of Clinical Oncology, 2003, vol. 21, No. 21, pp. 3940-3947.
Livingston et al., "Selection of GM2, fucosyl GM1, globo H and polysialic acid as targets on small cell lung cancers for antibody mediated immunotherapy," Cancer Immunol. Immunother., 2005, 54: 1018-1025.
Chugai Seiyaku Kabushiki Kaisha, "Sequence Alignments," dated Mar. 6, 2020, submitted in counterpart European Patent Application No. 11736812.6, 2 pages.
Maier et al., "Correlation of mRNA and protein in complex biological samples," FEBS Letters, 2009, 583: 3966-3973.
Communication, dated Jun. 10, 2020, issued by the European Patent Office in counterpart European Patent Application No. 18 156 974.0-1111.
Chugai Seiyaku Kabushiki Kaisha, Final Written Submission, dated Mar. 6, 2020, submitted in counterpart European Patent Application No. 11736812.6.
Communication, dated Oct. 10, 2019, from the European Patent Office in counterpart European Application No. 11736812.6.
Brendan D'Souza, et al. "Canonical and Non-Canonical Notch Ligands", Current Topics in Developmental Biology, 2010, vol. 92, pp. 73-129 (57 pages total).
Dov Greenbaum, et al., "Comparing protein abundance and mRNA expression levels on a genomic scale", Genome Biology, Aug. 29, 2003, vol. 4, issue 9, article 117, pp. 117.1-117.8 (8 pages total).
Saunders et al., "A DLL3-targeted antibody-drug conjugate eradicates high-grade pulmonary neuroendocrine tumor-initiating cells in vivo," Science Translational Medicine, Aug. 26, 2015, vol. 7, Issue 302, pp. 1-13.

(56) References Cited

OTHER PUBLICATIONS

Declaration from Dr. William Decker, dated Dec. 2020, filed in the Defence of Oppositions Against European Patent No. 2,530,091.
Spirin, Alexander S., "Storage of Messenger RNA in Eukaryotes: Envelopment With Protein, Translational Barrier at 5' Side, or Conformational Masking by 3' Side?," Molecular Reproduction and Development, May 1994, vol. 38, Issue 1, pp. 107-117.
Ranjan et al., "Masking mRNA from translation in somatic cells," Genes and Development (1993) vol. 7, pp. 1725-1736.
Declaration from Professor Mark Gerstein, "Expert Opinion," dated Feb. 2020, submitted in opposition proceedings against European Patent No. 2,530,091.
Gad et al., "Nonclinical Vehicle Use in Studies by Multiple Routes in Multiple Species," International Journal of Toxicology, Nov-Dec. 2006, vol. 25, Issue 6, pp. 499-521.
Katoh et al., "Precision medicine for human cancers with Notch signaling dysregulation (Review)," International Journal of Molecular Medicine, Feb. 2020, vol. 45, Issue 2, pp. 279-297.
Espinoza et al. "Notch Inhibitors for Cancer Treatment," Pharmacology & Therapeutics, Aug. 2013, vol. 139, Issue 2, pp. 95-110.
Von Meerten et al. "Complement-Induced Cell Death by Rituximab Depends on CD20 Expression Level and Acts Complementary to Antibody-Dependent Cellular Cytotoxicity," Clinical Cancer Research, Jul. 1, 2006, vol. 12, Issue 13, pp. 4027-4035.
Gershoni et al., "Epitope Mapping-The First Step in Developing Epitope-Based Vaccines," Biodrugs, 2007, vol. 21, Issue 3, pp. 145-156.
Knowles et al., "Advances in Immuno-Positron Emission Tomography: Antibodies for Molecular Imaging in Oncology," Journal of Clinical Oncology, Nov. 1, 2012, vol. 30, No. 31, pp. 3884-3892.
Communication, dated Mar. 22, 2019, issued by European Patent Office in European Patent No. 2,990,420.
De La Lastra et al., "Epitope mapping of 10 monoclonal antibodies against the pig analogue of human membrane cofactor protein (MCP)," Immunology, Apr. 1999, vol. 96, No. 4, pp. 663-670.
Coullu et al., "Cooperation between Wnt and Notch signalling in human breast cancer," (2007) Breast Cancer Research, May 11, 2007, vol. 9: No. 3, (3 pages).
Guo et al., "Role of Notch and its oncogenic signaling crosstalk in breast cancer," Biochimica et Biophysica Acta (BBA)—Reviews on Cancer, Apr. 2011, vol. 1815, Issue 2, pp. 197-213.
Ercan et al., "Mammary Development and Breast Cancer: The Role of Stem Cells," Current Molecular Medicine, Jun. 2011, vol. 11, No. 4, pp. 270-285.
Wang et al., "Epithelial-mesenchymal transition in breast cancer progression and metastasis," Chinese Journal of Cancer; Sep. 2011, vol. 30, No. 9,: pp. 603-611.
Information about the result of oral proceedings in European Patent Application No. 11736812.6, dated Mar. 4, 2021.
Communication, dated Jun. 10, 2020, issued by European Patent Office in European Application No. 18 156 974.0.
Communication, dated Oct. 10, 2019, issued by European Patent Office in European Application No. 11736812.6.
Weinzierl, et al., Notice of opposition filed against EP 2 530 091 B1 dated Jan. 2, 2019 (50 pages).
Unsin, Dr. Claudia E, Notice of opposition filed against EP 2 530 091 B1 dated Jan. 2, 2019 (16 pages).
Campoli et al., "Immunotherapy of Malignant Disease with Tumor Antigen-Specific Monoclonal Antibodies", Clinical Cancer Research, vo. 16, No. 1, Jan. 1, 2010, pp. 11-20 (10 pages total).
Staerz et al., "Hybrid antibodies can target sites for attack by T cells", Nature, vol. 314, No. 6012, Apr. 18, 1985, pp. 628-631 (2 pages total).
Mezzanzanica et al., "Human Ovarian Carcinoma Lysis By Cytotoxic T Cells Targeted by Bispecific Monoclonal Antibodies: Analysis of the Antibody Components", Int. J. Cancer, vol. 41, No. 4, pp. 609-615, 1988 (4 pages total).
Staerz et al., "Hybrid hybridoma producing a bispecific monoclonal antibody that can focus effector T-cell activity", Proc. Natl. Acad. Sci. USA, vol. 83, vol. 5, pp. 1453-1457, Mar. 1986, Immunology (3 pages total).
Mack et al., "A small bispecific antibody construct expressed as a functional single-chain molecule with high tumor cell cytotoxicity", Proc. Natl. Acad. Sci. USA, vol. 92, pp. 7021-7025, Jul. 1995 (3 pages total).
Wolf et al., "BiTEs: bispecific antibody constructs with unique anti-tumor activity", Drug Discov Today, vol. 10, No. 18, pp. 1237-1244, Sep. 2005 (8 pages total).
Dreier et at., "Extremely Potent, Rapid and Costimulation-Independent Cytotoxic T-Cell Response Against Lymphoma Cells Catalyzed By a Single-Chain Bispecific Antibody", Int. J Cancer, Aug. 20, 2002, vol. 100, No. 6, pp. 690-697 (8 pages total).
Sebastian et al., "Treatment of non-small cell lung cancer patients with the trifunctional monoclonal antibody catumaxomab (anti-EpCAM x anti-CD3): a phase I study", Cancer Immunol Immunother, 2007, vol. 56, No. 10, pp. 1637-1644 (8 pages total).
Schlereth et al., "T-cell activation and B-cell depletion in chimpanzees treated with a bispecific anti-CD 19/anti-CD3 single-chain antibody construct", Cancer Immunol Immunother, 2006, vol. 55, No. 5, pp. 503-514 (12 pages total).
Amann et al., "Therapeutic window of an EpCAM/CD3-specific BiTE antibody in mice is determined by a subpopulation of EpCAM-expressing lymphocytes that is absent in humans", Cancer Immunol Immunother, 2009, vol. 58, No. 1, pp. 95-109 (15 pages total).
Bulman et al., "Mutations in the human *Delta* homologue, *DLL3*, cause axial skeletal defects in spondylocostal dysostosis", Nature Genetics, Apr. 2000, vol. 24, No. 4, pp. 438-441(4 pages total).
Turnpenny et al., "Novel mutations in *DLL3*, a somitogenesis gene encoding a ligand for the Notch signalling pathway, cause a consistent pattern of abnormal vertebral segmentation in spondylocostal dysostosis", J Med Genet., May 2003, vol. 40, No. 5, pp. 333-339 (7 pages total).
Phillips et al., "Molecular subclasses of high-grade glioma predict prognosis, delineate a pattern of disease progression, and resemble stages in neurogenesis", Cancer Cell, vol. 9, vol. 1, pp. 157-173, Mar. 2006 (17 pages total).
Mullendore et al., "Ligand-dependent Notch Signaling Is Involved in Tumor Initiation and Tumor Maintenance in Pancreatic Cancer", Clin. Cancer Res., Apr. 2009, vol. 15, No. 7, pp. 2291-2301 (11 pages total).

* cited by examiner

Fig.5
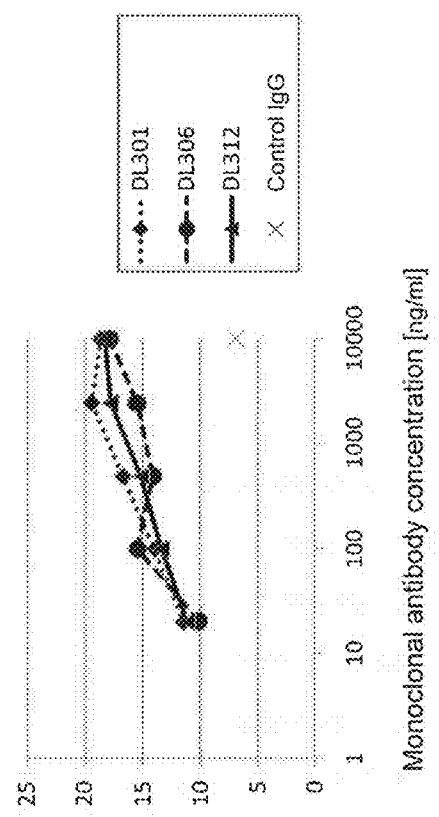
(a)
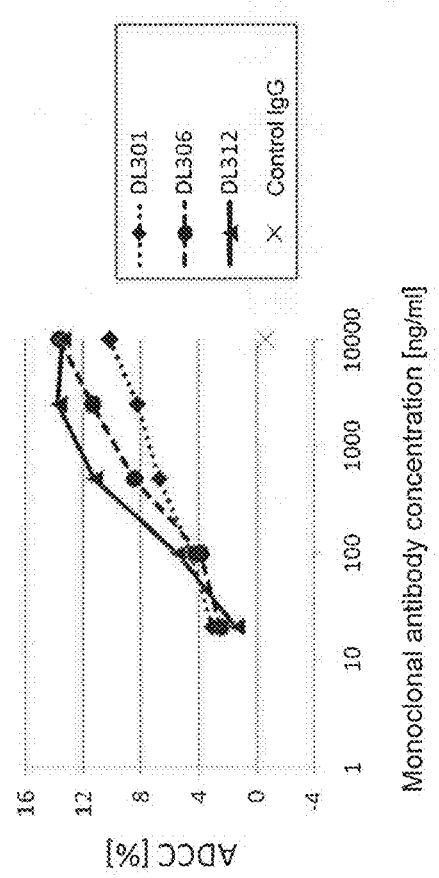
(b)

Fig.7
(a) Human DLL3/BaF3
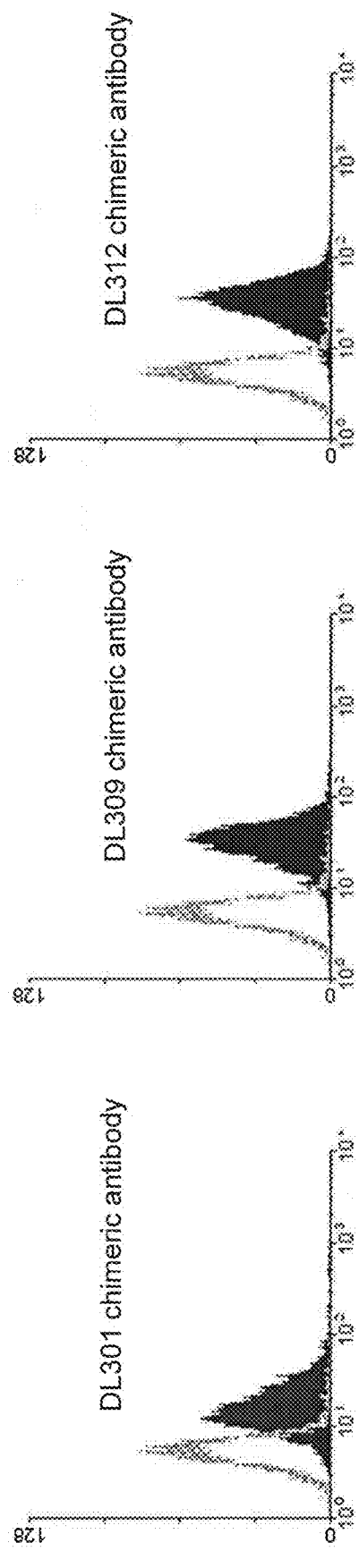
(b) Ba/F3
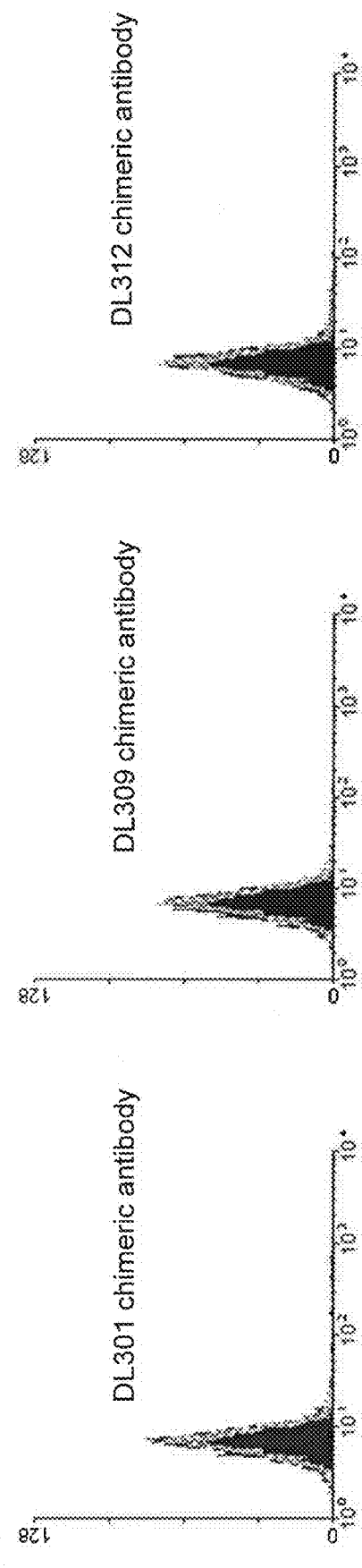

ANTI-DLL3 ANTIBODY

The present application is a Continuation of U.S. application Ser. No. 13/575,861, filed Sep. 12, 2012, (now U.S. Pat. No. 9,127,071, issued Sep. 8, 2015), which is a National Stage Application filed under § 371 of PCT Application No. PCT/JP2011/000485, filed Jan. 28, 2011, which claims the priority based on Japanese Patent Application No. 2010-019391 (filed on Jan. 29, 2010). The contents thereof are incorporated herein by reference. The present invention relates to an anticancer agent and a method for diagnosing cancer.

TECHNICAL FIELD

Background Art

Small-cell lung cancer accounts for approximately 20% of all lung cancer incidence. The small-cell lung cancer rapidly progresses and is difficult to be surgically removed because lymph node metastasis or distant metastasis has already occurred at the time of diagnosis in many cases. This cancer exhibits high response rates to an anticancer agent in its early stage. Thus, chemotherapy is considered as the first choice for treating the cancer. The cancer, however, immediately becomes resistant to chemotherapy and recurs, resulting in a 3-year survival rate of 5% or lower. Hence, new therapy has been demanded.

Delta-like 3 (DLL3) is a type I membrane protein belonging to Notch ligand family members. DLL3 is necessary for normal somite formation and patterning. Mutations in DLL3 cause rib defects or spondylolysis in autosomal recessive spondylocostal dysostosis patients [Non Patent Literatures 1 and 2]. DLL1 localizes on cell surface and binds to Notch, whereas DLL3 predominantly localizes in the Golgi apparatus and does not bind to Notch [Non Patent Literatures 3 and 4].

There exist previous studies reporting the amplification of the DLL3 gene on chromosome and increased expression of this gene in pancreatic cancer cell lines [Non Patent Literature 5] and increased DLL3 expression in some glioma cases [Non Patent Literature 6]. However, the number of the DLL3 protein on cell surface has not yet been reported. The expression of $10^5$ or more antigen molecules for unmodified antibodies or antigen molecules of $10^4$ order even for defucosylated antibodies having the enhanced ability to induce antibody-dependent cell-mediated cytotoxicity (ADCC) is required for targeting the antigen molecules on cell surface using such antibodies or for killing cancer cells under the anti-tumor mechanism of the ADCC activity [Non Patent Literature 7]. Thus, it is uncertain whether DLL3 is suitable as a therapeutic target based on antibodies.

Mouse anti-DLL3 monoclonal antibodies (MAB4315, R&D Systems, Inc.) are already commercially available as a research reagent.

CITATION LIST

Non Patent Literature

Non Patent Literature 1: Bulman, M. P. et al. (2000) Nat Genet 24, 438-441.
Non Patent Literature 2: Turnpenny, P. D. et al. (2003) J Med Genet 40, 333-339.
Non Patent Literature 3: Geffers, I. et al. (2007) J Cell Biol 178, 465-476.
Non Patent Literature 4: Ladi, E. et al. (2005) J Cell Biol 170, 983-992.
Non Patent Literature 5: Phillips, H. S. (2006) Cancer Cell 9, 157-173.
Non Patent Literature 6: Mulledndore, M. E. (2009) Clin Cancer Res 15, 2291-2301.
Non Patent Literature 7: Kenya Shitara (2009) YAKUGAKU ZASSHI 129, 3-9.

SUMMARY OF INVENTION

Technical Problem

An object of the present invention is to provide a novel antibody, an anticancer agent comprising the same, and a method for diagnosing cancer using the same.

Solution to Problem

The present inventors found that DLL3 mRNA expression was increased in small-cell lung cancer. Its expression was low in all normal tissues except for the fetal brain. The present inventors prepared monoclonal antibodies against the DLL3 protein. The antigen level on cell surface measured based on the capability of binding to the antibody was only less than $10^4$ per expressing cell. Unexpectedly, the present inventors found that an antibody that bound to DLL3 via a characteristic epitope in the vicinity of the C terminus of the extracellular domain stably resided on the cell membrane and had an ADCC-inducing activity.

Specifically, the present inventors successively screened for an antibody having an anti-tumor activity. Moreover, the present inventors found that an antibody conjugated with toxin had a cytotoxic activity against DLL3-expressing cells. From these findings, the present inventors found that the anti-DLL3 antibody was useful in the diagnosis, prevention, and treatment of primary or metastatic cancer expressing DLL3. Based on these findings, the present invention has been completed.

The present invention provides an antibody which binds to DLL3 protein. Preferably, the antibody of the present invention has a cytotoxic activity. Particularly preferably, the cytotoxic activity is an antibody-dependent cell-mediated cytotoxic activity (ADCC activity). Also preferably, the antibody of the present invention has an internalization activity. Also preferably, the antibody of the present invention is conjugated with a cytotoxic substance. Also preferably, the antibody of the present invention recognizes a region from amino acids 216 to 492 in human DLL3 having the amino acid sequence as set forth in SEQ ID NO: 1.

In another aspect, the present invention provides an antibody which binds to DLL3 protein described in any of the following:

(1) an antibody comprising a heavy chain variable region comprising heavy chain CDR1 having the amino acid sequence as set forth in SEQ ID NO: 12, heavy chain CDR2 having the amino acid sequence as set forth in SEQ ID NO: 13, and heavy chain CDR3 having the amino acid sequence as set forth in SEQ ID NO: 14;

(2) an antibody comprising a heavy chain variable region comprising heavy chain CDR1 having the amino acid sequence as set forth in SEQ ID NO: 24, heavy chain CDR2 having the amino acid sequence as set forth in SEQ ID NO: 25, and heavy chain CDR3 having the amino acid sequence as set forth in SEQ ID NO: 26;

(3) an antibody comprising a heavy chain variable region comprising heavy chain CDR1 having the amino acid sequence as set forth in SEQ ID NO: 36, heavy chain CDR2 having the amino acid sequence as set forth in SEQ ID NO: 37, and heavy chain CDR3 having the amino acid sequence as set forth in SEQ ID NO: 38;

(4) an antibody comprising a heavy chain variable region comprising heavy chain CDR1 having the amino acid sequence as set forth in SEQ ID NO: 48, heavy chain CDR2 having the amino acid sequence as set forth in SEQ ID NO: 49, and heavy chain CDR3 having the amino acid sequence as set forth in SEQ ID NO: 50;

(5) an antibody comprising a light chain variable region comprising light chain CDR1 having the amino acid sequence as set forth in SEQ ID NO: 18, light chain CDR2 having the amino acid sequence as set forth in SEQ ID NO: 19, and light chain CDR3 having the amino acid sequence as set forth in SEQ ID NO: 20;

(6) an antibody comprising a light chain variable region comprising light chain CDR1 having the amino acid sequence as set forth in SEQ ID NO: 30, light chain CDR2 having the amino acid sequence as set forth in SEQ ID NO: 31, and light chain CDR3 having the amino acid sequence as set forth in SEQ ID NO: 32;

(7) an antibody comprising a light chain variable region comprising light chain CDR1 having the amino acid sequence as set forth in SEQ ID NO: 42, light chain CDR2 having the amino acid sequence as set forth in SEQ ID NO: 43, and light chain CDR3 having the amino acid sequence as set forth in SEQ ID NO: 44;

(8) an antibody comprising a light chain variable region comprising light chain CDR1 having the amino acid sequence as set forth in SEQ ID NO: 54, light chain CDR2 having the amino acid sequence as set forth in SEQ ID NO: 55, and light chain CDR3 having the amino acid sequence as set forth in SEQ ID NO: 56;

(9) an antibody comprising a heavy chain variable region comprising heavy chain CDR1 having the amino acid sequence as set forth in SEQ ID NO: 12, heavy chain CDR2 having the amino acid sequence as set forth in SEQ ID NO: 13, and heavy chain CDR3 having the amino acid sequence as set forth in SEQ ID NO: 14, and a light chain variable region comprising light chain CDR1 having the amino acid sequence as set forth in SEQ ID NO: 18, light chain CDR2 having the amino acid sequence as set forth in SEQ ID NO: 19, and light chain CDR3 having the amino acid sequence as set forth in SEQ ID NO: 20;

(10) an antibody comprising a heavy chain variable region comprising heavy chain CDR1 having the amino acid sequence as set forth in SEQ ID NO: 24, heavy chain CDR2 having the amino acid sequence as set forth in SEQ ID NO: 25, and heavy chain CDR3 having the amino acid sequence as set forth in SEQ ID NO: 26, and a light chain variable region comprising light chain CDR1 having the amino acid sequence as set forth in SEQ ID NO: 30, light chain CDR2 having the amino acid sequence as set forth in SEQ ID NO: 31, and light chain CDR3 having the amino acid sequence as set forth in SEQ ID NO: 32;

(11) an antibody comprising a heavy chain variable region comprising heavy chain CDR1 having the amino acid sequence as set forth in SEQ ID NO: 36, heavy chain CDR2 having the amino acid sequence as set forth in SEQ ID NO: 37, and heavy chain CDR3 having the amino acid sequence as set forth in SEQ ID NO: 38, and a light chain variable region comprising light chain CDR1 having the amino acid sequence as set forth in SEQ ID NO: 42, light chain CDR2 having the amino acid sequence as set forth in SEQ ID NO: 43, and light chain CDR3 having the amino acid sequence as set forth in SEQ ID NO: 44;

(12) an antibody comprising a heavy chain variable region comprising heavy chain CDR1 having the amino acid sequence as set forth in SEQ ID NO: 48, heavy chain CDR2 having the amino acid sequence as set forth in SEQ ID NO: 49, and heavy chain CDR3 having the amino acid sequence as set forth in SEQ ID NO: 50, and a light chain variable region comprising light chain CDR1 having the amino acid sequence as set forth in SEQ ID NO: 54, light chain CDR2 having the amino acid sequence as set forth in SEQ ID NO: 55, and light chain CDR3 having the amino acid sequence as set forth in SEQ ID NO: 56;

(13) an antibody comprising one or more amino acid substitutions, deletions, additions, and/or insertions in the antibody of any one of (1) to (12) and has an activity equivalent to that of any of the antibodies (1) to (12); and

(14) an antibody which binds to the same epitope as that in DLL3 protein to which any of the antibodies (1) to (12) bind.

In a further alternative aspect, the present invention provides a pharmaceutical composition comprising any of the antibodies described above as an active ingredient. Preferably, the pharmaceutical composition of the present invention is an anticancer agent. Particularly preferably, the anticancer agent targets lung cancer.

In a further alternative aspect, the present invention provides a method for diagnosing cancer, comprising the following steps:

(a) providing a sample isolated from a test subject; and
(b) detecting the expression level of DLL3 protein or DLL3 gene in the sample. Preferably, the diagnosis method of the present invention is intended for the diagnosis of lung cancer. The present invention also provides a diagnostic agent for cancer comprising any of the antibodies described above.

BRIEF DESCRIPTION OF DRAWINGS

FIG. 5 shows the antibody concentration dependence of an ADCC activity against target cells DLL3/BaF3 (a) and NCI-H1184 (b).

FIG. 7 shows the binding of a recombinant anti-DLL3 antibody to the DLL3 protein on cell surface.

DESCRIPTION OF EMBODIMENTS

DLL3

Figure 1:
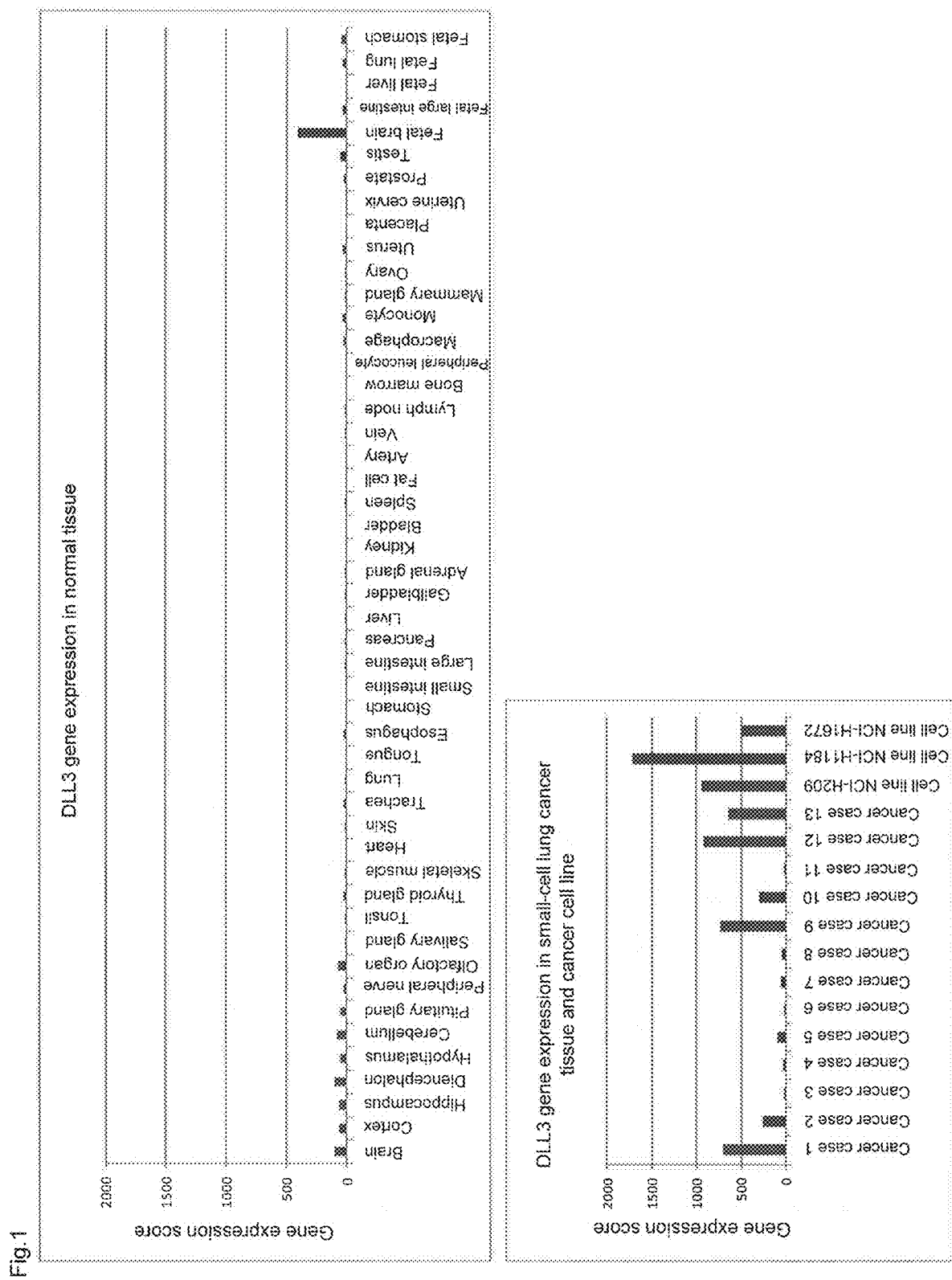
FIG. 1 shows increased DLL3 expression in small-cell lung cancer and the fetal brain.

The amino acid sequence of DLL3 (Delta-like 3) is known in the art. For example, the amino acid sequence of human DLL3 is as set forth in SEQ ID NO: 1 (NM_016941), and the amino acid sequence of mouse DLL3 is as set forth in SEQ ID NO: 2 (NM_007866).

The DLL3 protein used in the present invention may be a DLL3 protein having the sequence described above or may be a modified protein having a sequence derived from the sequence described above by the modification of one or more amino acids. Examples of the modified protein having a sequence derived from the sequence described above by the modification of one or more amino acids can include polypeptides having 70% or more, preferably 80% or more, more preferably 90% or more, even more preferably 95% or more homology to the amino acid sequence. Alternatively, partial peptides of these DLL3 proteins may be used.

The DLL3 protein used in the present invention is not limited by its origin and is preferably a human DLL3 protein.

Anti-DLL3 Antibody

The anti-DLL3 antibody used in the present invention needs only to bind to the DLL3 protein and is not particularly limited by its origin, type, shape, etc. Specifically, an antibody can be used, such as a non-human animal-derived antibody (e.g., a mouse, rat, or camel antibody), a human-derived antibody, a chimeric antibody, or a humanized antibody. The anti-DLL3 antibody used in the present invention may be a polyclonal or monoclonal antibody and is preferably a monoclonal antibody.

The anti-DLL3 antibody used in the present invention is preferably an anti-human DLL3 antibody. The anti-human DLL3 antibody may be an antibody which specifically binds to human DLL3 or may be an antibody which binds to human DLL3 as well as non-human animal-derived DLL3 (e.g., mouse DLL3).

The anti-DLL3 antibody used in the present invention can be obtained as a polyclonal or monoclonal antibody using means known in the art. The anti-DLL3 antibody used in the present invention is particularly preferably a mammal-derived monoclonal antibody. The mammal-derived monoclonal antibody encompasses, for example, those produced by hybridomas and those produced by hosts transformed with expression vectors containing an antibody gene by a genetic engineering approach.

The anti-DLL3 antibody of the present invention may be modified with various molecules such as polyethylene glycol (PEG). As described later, the anti-DLL3 antibody of the present invention may also be modified with a chemotherapeutic agent, a radioactive chemical, or the like, having a cytotoxic activity.

Examples of the antibody used in the present invention, which recognizes DLL3 and binds thereto, can include the following antibodies:

(1) an antibody (DL301) comprising a heavy chain variable region comprising heavy chain CDR1 having the amino acid sequence as set forth in SEQ ID NO: 12, heavy chain CDR2 having the amino acid sequence as set forth in SEQ ID NO: 13, and heavy chain CDR3 having the amino acid sequence as set forth in SEQ ID NO: 14;

(2) an antibody (DL306) comprising a heavy chain variable region comprising heavy chain CDR1 having the amino acid sequence as set forth in SEQ ID NO: 24, heavy chain CDR2 having the amino acid sequence as set forth in SEQ ID NO: 25, and heavy chain CDR3 having the amino acid sequence as set forth in SEQ ID NO: 26;

(3) an antibody (DL309) comprising a heavy chain variable region comprising heavy chain CDR1 having the amino acid sequence as set forth in SEQ ID NO: 36, heavy chain CDR2 having the amino acid sequence as set forth in SEQ ID NO: 37, and heavy chain CDR3 having the amino acid sequence as set forth in SEQ ID NO: 38;

(4) an antibody (DL312) comprising a heavy chain variable region comprising heavy chain CDR1 having the amino acid sequence as set forth in SEQ ID NO: 48, heavy chain CDR2 having the amino acid sequence as set forth in SEQ ID NO: 49, and heavy chain CDR3 having the amino acid sequence as set forth in SEQ ID NO: 50;

(5) an antibody (DL301) comprising a light chain variable region comprising light chain CDR1 having the amino acid sequence as set forth in SEQ ID NO: 18, light chain CDR2 having the amino acid sequence as set forth in SEQ ID NO: 19, and light chain CDR3 having the amino acid sequence as set forth in SEQ ID NO: 20;

(6) an antibody (DL306) comprising a light chain variable region comprising light chain CDR1 having the amino acid sequence as set forth in SEQ ID NO: 30, light chain CDR2 having the amino acid sequence as set forth in SEQ ID NO: 31, and light chain CDR3 having the amino acid sequence as set forth in SEQ ID NO: 32;

(7) an antibody (DL309) comprising a light chain variable region comprising light chain CDR1 having the amino acid sequence as set forth in SEQ ID NO: 42, light chain CDR2 having the amino acid sequence as set forth in SEQ ID NO: 43, and light chain CDR3 having the amino acid sequence as set forth in SEQ ID NO: 44;

(8) an antibody (DL312) comprising a light chain variable region comprising light chain CDR1 having the amino acid sequence as set forth in SEQ ID NO: 54, light chain CDR2 having the amino acid sequence as set forth in SEQ ID NO: 55, and light chain CDR3 having the amino acid sequence as set forth in SEQ ID NO: 56;

(9) an antibody (DL301) comprising a heavy chain variable region comprising heavy chain CDR1 having the amino acid sequence as set forth in SEQ ID NO: 12, heavy chain CDR2 having the amino acid sequence as set forth in SEQ ID NO: 13, and heavy chain CDR3 having the amino acid sequence as set forth in SEQ ID NO: 14, and a light chain variable region comprising light chain CDR1 having the amino acid sequence as set forth in SEQ ID NO: 18, light chain CDR2 having the amino acid sequence as set forth in SEQ ID NO: 19, and light chain CDR3 having the amino acid sequence as set forth in SEQ ID NO: 20;

(10) an antibody (DL306) comprising a heavy chain variable region comprising heavy chain CDR1 having the amino acid sequence as set forth in SEQ ID NO: 24, heavy chain CDR2 having the amino acid sequence as set forth in SEQ ID NO: 25, and heavy chain CDR3 having the amino acid sequence as set forth in SEQ ID NO: 26, and a light chain variable region comprising light chain CDR1 having the amino acid sequence as set forth in SEQ ID NO: 30, light chain CDR2 having the amino acid sequence as set forth in SEQ ID NO: 31, and light chain CDR3 having the amino acid sequence as set forth in SEQ ID NO: 32;

(11) an antibody (DL309) comprising a heavy chain variable region comprising heavy chain CDR1 having the amino acid sequence as set forth in SEQ ID NO: 36, heavy chain CDR2 having the amino acid sequence as set forth in SEQ ID NO: 37, and heavy chain CDR3 having the amino acid sequence as set forth in SEQ ID NO: 38, and a light chain variable region comprising light chain CDR1 having the amino acid sequence as set forth in SEQ ID NO: 42, light chain CDR2 having the amino acid sequence as set forth in SEQ ID NO: 43, and light chain CDR3 having the amino acid sequence as set forth in SEQ ID NO: 44;

(12) an antibody (DL312) comprising a heavy chain variable region comprising heavy chain CDR1 having the amino acid sequence as set forth in SEQ ID NO: 48, heavy chain CDR2 having the amino acid sequence as set forth in SEQ ID NO: 49, and heavy chain CDR3 having the amino acid sequence as set forth in SEQ ID NO: 50, and a light chain variable region comprising light chain CDR1 having the amino acid sequence as set forth in SEQ ID NO: 54, light chain CDR2 having the amino acid sequence as set forth in SEQ ID NO: 55, and light chain CDR3 having the amino acid sequence as set forth in SEQ ID NO: 56;

(13) an antibody that is derived from any of the antibodies (1) to (12) by the substitution, deletion, addition, and/or insertion of one or more amino acids and has an activity equivalent to that of any of the antibodies (1) to (12); and

(14) an antibody which binds to the same epitope as that in DLL3 protein to which any of the antibodies (1) to (12) bind.

The antibodies (1) to (12) may contain constant regions. The constant regions used are not particularly limited, and any constant region may be used. Preferable examples of the constant regions used in the present invention can include human-derived constant regions. For example, a human IgG1-derived, human IgG2-derived, human IgG3-derived, or human IgG4-derived constant region can be used as a heavy chain constant region. Also, for example, human κ chain-derived or human λ chain-derived constant region can be used as a light chain constant region. The constant regions used in the present invention may be constant regions having a native sequence or may be modified constant regions having a sequence derived from the native sequence by the modification of one or more amino acids.

The antibodies (1) to (12) may contain FRs. The FRs used are not particularly limited, and any FR may be used as long as the resulting antibody maintains its binding activity against human DLL3. Preferable examples of the FRs used in the present invention can include human antibody-derived FRs. Since the technique of FR replacement with the antigen binding activity of an antibody maintained is known in the art, those skilled in the art can appropriately select FRs. The FRs used in the present invention may be FRs having a native sequence or may be FRs having a sequence derived from the native sequence by the modification of one or more amino acids.

Examples of the heavy chain variable region comprising heavy chain CDR1 having the amino acid sequence as set forth in SEQ ID NO: 12, heavy chain CDR2 having the amino acid sequence as set forth in SEQ ID NO: 13, and heavy chain CDR3 having the amino acid sequence as set forth in SEQ ID NO: 14 can include a heavy chain variable region having the amino acid sequence as set forth in SEQ ID NO: 9. Also, examples of the heavy chain comprising the heavy chain variable region can include a heavy chain having the amino acid sequence of SEQ ID NO: 10 or 11.

Examples of the heavy chain variable region comprising heavy chain CDR1 having the amino acid sequence as set forth in SEQ ID NO: 24, heavy chain CDR2 having the amino acid sequence as set forth in SEQ ID NO: 25, and heavy chain CDR3 having the amino acid sequence as set forth in SEQ ID NO: 26 can include a heavy chain variable region having the amino acid sequence as set forth in SEQ ID NO: 21. Also, examples of the heavy chain comprising the heavy chain variable region can include a heavy chain having the amino acid sequence of SEQ ID NO: 22 or 23.

Examples of the heavy chain variable region comprising heavy chain CDR1 having the amino acid sequence as set forth in SEQ ID NO: 36, heavy chain CDR2 having the amino acid sequence as set forth in SEQ ID NO: 37, and heavy chain CDR3 having the amino acid sequence as set forth in SEQ ID NO: 38 can include a heavy chain variable region having the amino acid sequence as set forth in SEQ ID NO: 33. Also, examples of the heavy chain comprising the heavy chain variable region can include a heavy chain having the amino acid sequence of SEQ ID NO: 34 or 35.

Examples of the heavy chain variable region comprising heavy chain CDR1 having the amino acid sequence as set forth in SEQ ID NO: 48, heavy chain CDR2 having the amino acid sequence as set forth in SEQ ID NO: 49, and heavy chain CDR3 having the amino acid sequence as set forth in SEQ ID NO: 50 can include a heavy chain variable region having the amino acid sequence as set forth in SEQ ID NO: 45. Also, examples of the heavy chain comprising the heavy chain variable region can include a heavy chain having the amino acid sequence of SEQ ID NO: 46 or 47.

Examples of the light chain variable region comprising light chain CDR1 having the amino acid sequence as set forth in SEQ ID NO: 18, light chain CDR2 having the amino acid sequence as set forth in SEQ ID NO: 19, and light chain CDR3 having the amino acid sequence as set forth in SEQ ID NO: 20 can include a light chain variable region having the amino acid sequence as set forth in SEQ ID NO: 15. Also, examples of the light chain comprising the light chain variable region can include a light chain having the amino acid sequence of SEQ ID NO: 16 or 17.

Examples of the light chain variable region comprising light chain CDR1 having the amino acid sequence as set forth in SEQ ID NO: 30, light chain CDR2 having the amino acid sequence as set forth in SEQ ID NO: 31, and light chain CDR3 having the amino acid sequence as set forth in SEQ ID NO: 32 can include a light chain variable region having the amino acid sequence as set forth in SEQ ID NO: 27. Also, examples of the light chain comprising the light chain variable region can include a light chain having the amino acid sequence of SEQ ID NO: 28 or 29.

Examples of the light chain variable region comprising light chain CDR1 having the amino acid sequence as set forth in SEQ ID NO: 42, light chain CDR2 having the amino acid sequence as set forth in SEQ ID NO: 43, and light chain CDR3 having the amino acid sequence as set forth in SEQ ID NO: 44 can include a light chain variable region having the amino acid sequence as set forth in SEQ ID NO: 39. Also, examples of the light chain comprising the light chain variable region can include a light chain having the amino acid sequence of SEQ ID NO: 40 or 41.

Examples of the light chain variable region comprising light chain CDR1 having the amino acid sequence as set forth in SEQ ID NO: 54, light chain CDR2 having the amino acid sequence as set forth in SEQ ID NO: 55, and light chain CDR3 having the amino acid sequence as set forth in SEQ ID NO: 56 can include a light chain variable region having the amino acid sequence as set forth in SEQ ID NO: 51. Also, examples of the light chain comprising the light chain variable region can include a light chain having the amino acid sequence of SEQ ID NO: 52 or 53.

In the present invention, the phrase "having an activity equivalent to that of the antibody of the present invention" refers to having a DLL3 binding activity, an internalization activity, and/or a cytotoxic activity (ADCC activity, etc.) against DLL3-expressing cells equivalent thereto. In the present invention, the equivalent activity is not necessarily required to be an identical activity and may be, for example, 50% or more, preferably 70% or more, more preferably 90% or more activity compared with the activity of any of the antibodies (1) to (12). Examples of the upper limit of the activity can include, but not particularly limited to, 1000% or less, 500% or less, 300% or less, 150% or less, and 100% or less.

An antibody derived from the antibody of the present invention by the substitution, deletion, addition, and/or insertion of one or more amino acids is also incorporated in the scope of the present invention and may be prepared artificially or occur naturally. Examples of a method for introducing a mutation in the polypeptide include site-directed mutagenesis (Hashimoto-Gotoh, T. et al. (1995) Gene 152, 271-275, Zoller, M J, and Smith, M. (1983) Methods Enzymol. 100, 468-500, Kramer, W. et al. (1984) Nucleic Acids Res. 12, 9441-9456, Kramer W, and Fritz H J (1987) Methods. Enzymol. 154, 350-367, Kunkel, T A (1985) Proc Natl Acad Sci USA. 82, 488-492, Kunkel (1988) Methods Enzymol. 85, 2763-2766). This is one of methods well known by those skilled in the art for preparing a polypeptide functionally equivalent to a certain polypeptide. Those skilled in the art can appropriately introduce a mutation in the antibody of the present invention using such a method and thereby prepare an antibody functionally equivalent to the antibody. Moreover, amino acid mutations may occur in the natural world. Such an antibody that has an amino acid sequence derived from the amino acid sequence of the antibody of the present invention by the mutation of one or more amino acids and is functionally equivalent to the antibody is also encompassed by the antibody of the present invention.

The number of amino acids mutated in such a variant is usually within 50 amino acids, preferably within 30 amino acids, more preferably within 10 amino acids (e.g., within 5 amino acids).

For amino acid residues to be mutated, it is preferred that this mutation should be performed conservatively between amino acids having the same side chain property. For example, the following classification based on the properties of amino acid side chains has been established:
hydrophobic amino acids (A, I, L, M, F, P, W, Y, and V),
hydrophilic amino acids (R, D, N, C, E, Q, G, H, K, S, and T),
amino acids having an aliphatic side chain (G, A, V, L, I, and P),
amino acids having a hydroxy group-containing side chain (S, T, and Y),
amino acids having a sulfur atom-containing side chain (C and M),
amino acids having a side chain containing carboxylic acid and amide (D, N, E, and Q),
amino acids having a base-containing side chain (R, K, and H), and
amino acids having an aromatic group-containing side chain (H, F, Y, and W)
(all symbols within the parentheses represent single letter codes of amino acids).

A polypeptide having an amino acid sequence modified from a certain amino acid sequence by the deletion and/or addition of one or more amino acid residue(s) and/or substitution thereof by other amino acids is already known to maintain the biological activity of the original polypeptide (Mark, D. F. et al., Proc. Natl. Acad. Sci. USA (1984) 81, 5662-5666, Zoller, M. J. and Smith, M., Nucleic Acids Research (1982) 10, 6487-6500, Wang, A. et al., Science 224, 1431-1433, Dalbadie-McFarland, G. et al., Proc. Natl. Acad. Sci. USA (1982) 79, 6409-6413). Specifically, when amino acids in an amino acid sequence constituting a certain polypeptide are substituted by amino acids classified in the same group thereas, it is generally said that the polypeptide is likely to maintain its activity. In the present invention, the substitution between amino acids within the same amino acid group described above is referred to as conservative substitution.

The present invention also provides an antibody which binds to the same epitope as that to which any of the antibodies (1) to (12) bind. Specific examples of the antibodies (1) to (12) can include antibodies DL301, DL306, DL309, and DL312 described below in Examples. Specifically, the present invention also provides an antibody recognizing the same epitope as that recognized by any of these antibodies.

Whether or not an analyte antibody shares an epitope with a certain antibody can be confirmed based on their competition for the same epitope. The competition between the antibodies is detected by cross-blocking assay or the like. The cross-blocking assay is preferably, for example, competitive ELISA assay.

Specifically, the cross-blocking assay involves preincubating DLL3 proteins coated on the wells of a microtiter plate in the presence or absence of a candidate competing antibody and then adding thereto the anti-DLL3 antibody of the present invention. The amount of the anti-DLL3 antibody of the present invention bound to the DLL3 protein in each well indirectly correlates with the binding capability of the candidate competing antibody (analyte antibody) that competes therewith for binding to the same epitope. Specifically, the higher affinity of the analyte antibody for the same epitope results in the smaller amount of the anti-DLL3 antibody of the present invention bound to the DLL3 protein-coated well and instead, the larger amount of the analyte antibody bound to the DLL3 protein-coated well.

The amount of each antibody bound to the well can be determined easily by labeling the antibody in advance. For example, a biotinylated antibody can be assayed using an avidin-peroxidase conjugate and an appropriate substrate. The cross-blocking assay using enzyme (e.g., peroxidase) labeling is particularly called competitive ELISA assay. The antibody may be labeled with any of other detectable or measurable labeling materials. Specifically, for example, radiolabeling or fluorescent labeling is known in the art.

Furthermore, when the analyte antibody has constant regions derived from a species different from that of the anti-DLL3 antibody of the present invention, the amount of any antibody bound to the well can also be measured using a labeled antibody that recognizes any constant region. Alternatively, even antibodies differing in class, albeit derived from the same species, can be measured for their respective amounts bound to the well using antibodies that discriminate each class.

Provided that the candidate antibody can block the binding of the anti-DLL3 antibody by at least 20%, preferably at least 30%, more preferably at least 50%, even more preferably at least 80%, compared to the binding activity obtained in the control test performed in the absence of the competing antibody, this candidate antibody is determined as an antibody that binds to substantially the same epitope as that to which the anti-DLL3 antibody of the present invention binds or as an antibody that competes therewith for the binding to the same epitope.

Further examples of the antibody of the present invention can include an antibody recognizing a region from amino acids 27 to 175 in human DLL3 (SEQ ID NO: 1) and an antibody recognizing a region from amino acids 216 to 492 in human DLL3. Examples of another aspect of the antibody of the present invention can include an antibody that binds to human DLL3 but does not bind to a polypeptide (DLL3delta1-Fc) consisting of the amino acid sequence of SEQ ID NO: 6 or a polypeptide (DLL3delta2-Fc) consisting of the amino acid sequence of SEQ ID NO: 7, and an antibody that binds to human DLL3 and also binds to the polypeptide (DLL3delta1-Fc) consisting of the amino acid sequence of SEQ ID NO: 6 and the polypeptide (DLL3delta2-Fc) consisting of the amino acid sequence of SEQ ID NO: 7.

The antibody of the present invention has activities such as an ADCC activity and an internalization activity and as such, is useful as a pharmaceutical drug, particularly, an anticancer agent.

Genetically Recombinant Anti-DLL3 Antibody

The antibody to be administered to humans can be converted to a genetically recombinant antibody that has been engineered artificially, for example, for the purpose of reducing heteroantigenicity in humans. The genetically recombinant antibody encompasses, for example, chimeric antibodies and humanized antibodies. These engineered antibodies can be produced using a method known in the art.

(1) Chimeric Antibody

The chimeric antibodies refer to antibodies comprising variable and constant regions of different origins ligated with each other. For example, mouse-human heterogeneous chimeric antibodies are antibodies comprising the heavy and light chain variable regions of a mouse antibody and the heavy and light chain constant regions of a human antibody. Mouse antibody variable region-encoding DNAs are ligated with human antibody constant region-encoding DNAs, and the ligation products can be incorporated into expression vectors to prepare chimeric antibody-expressing recombinant vectors. Cells transformed with these vectors (recombinant cells) can be cultured for the expression of the DNA insert to obtain the chimeric antibodies produced during the culture.

Human antibody constant regions are used as the constant regions of the chimeric antibodies. For example, Cγ1, Cγ2, Cγ3, Cγ4, Cμ, Cδ, Cα1, Cα2, and CE can be used as heavy chain constant regions. Moreover, Cκ and Cλ can be used as light chain constant regions. The amino acid sequences of these constant regions and nucleotide sequences encoding them are known in the art. Moreover, one or more amino acids in the human antibody constant regions can be substituted, deleted, added, and/or inserted for improving the stability of the antibody itself or of its production.

(2) Humanized Antibody

In general, the chimeric antibodies comprise non-human animal-derived antibody variable regions and human antibody-derived constant regions. By contrast, the humanized antibodies comprise non-human animal-derived antibody complementarity-determining regions (CDRs), human antibody-derived framework regions (FRs), and human antibody-derived constant regions. The humanized antibodies are also called reshaped human antibodies. Specifically, for example, humanized antibodies comprising non-human animal (e.g., mouse) antibody CDRs grafted in human antibodies are known in the art. The humanized antibodies are useful as active ingredients for a therapeutic agent of the present invention, owing to their reduced antigenicity in the human body.

Each antibody variable region usually comprises 3 CDRs flanked by 4 FRs. The CDR regions substantially determine the binding specificity of the antibody. The CDRs have diverse amino acid sequences. On the other hand, amino acid sequences constituting the FRs often exhibit high homology among antibodies having different binding specificities. Therefore, in general, the binding specificity of a certain antibody can allegedly be transplanted to other antibodies through CDR grafting.

General gene recombination approaches are also known for obtaining the humanized antibodies. Specifically, for example, Overlap Extension PCR is known in the art as a method for grafting mouse antibody CDRs into human FRs. The Overlap Extension PCR employs primers for human antibody FR synthesis comprising an additional nucleotide sequence encoding each mouse antibody CDR to be grafted. The primers are prepared for each of the 4 FRs. In the mouse CDR grafting into the human FRs, in general, it is allegedly advantageous to select human FRs highly homologous to mouse FRs for maintaining the CDR functions. Specifically, it is generally preferred to use human FRs comprising amino acid sequences highly homologous to those of the FRs adjacent to the mouse CDRs to be grafted.

Moreover, the nucleotide sequences to be ligated are designed such that they are connected in frame. The human FR-encoding nucleotide sequences are individually synthesized using their respective primers. As a result, products are obtained, which comprise the mouse CDR-encoding DNA added to each FR-encoding sequence. The mouse CDR-encoding nucleotide sequence in each product is designed such that the nucleotide sequence overlaps with another. Subsequently, the overlapping CDR portions are annealed to each other for complementary strand synthesis reaction. Through this reaction, the human FR sequences are ligated via the mouse CDR sequences.

Finally, the full-length gene of the variable region comprising 3 CDRs and 4 FRs ligated is amplified with primers that respectively anneal to the 5' and 3' ends thereof and comprise an additional recognition sequence for an appropriate restriction enzyme. The DNA thus obtained and human antibody constant region-encoding DNA can be inserted into expression vectors such that they are fused in frame to prepare vectors for humanized antibody expression. Hosts are transformed with these vectors to establish recombinant cells, which are then cultured for the expression of the humanized antibody-encoding DNA to produce the humanized antibodies into the cultures of the cultured cells (see European Patent Publication No. EP 239400 and International Publication No. WO 96/02576).

The humanized antibodies thus prepared can be evaluated for their binding activities for the antigen by qualitative or quantitative assay. As a result, human antibody FRs can be selected preferably such that they allow CDRs to form a favorable antigen-binding site when ligated via the CDRs. If necessary, FR amino acid residue(s) may be substituted such that the CDRs of the humanized antibody form an appropriate antigen-binding site. For example, a mutation can be introduced in the amino acid sequence of FR by applying the PCR method used in the mouse CDR grafting into the human FRs.

Specifically, a mutation of a partial nucleotide sequence can be introduced in the primers annealing to the FR nucleotide sequence. The FR nucleotide sequence synthesized using such primers contains the mutation thus introduced. The variant antibodies having the substituted amino acid(s) can be evaluated for their binding activities for the antigen by the same assay as above to select variant FR sequences having the desired property (Sato, K. et al., Cancer Res, 1993, 53, 851-856).

(3) Polyvalent Antibody

The antibody of the present invention encompasses not only bivalent antibodies typified by IgG (IgG1, IgG2, IgG4, etc.) but also monovalent antibodies or polyvalent antibodies typified by IgM as long as these antibodies bind to the DLL3 protein. The polyvalent antibody of the present invention encompasses polyvalent antibodies having antigen-binding sites, all of which are the same as each other or some or all of which are different from each other.

(4) Low-Molecular Antibody

The antibody of the present invention is not limited to whole antibody molecules and may be a low-molecular antibody or a modified form thereof as long as the antibody binds to the DLL3 protein.

The low-molecular antibody encompasses an antibody fragment deficient in a portion of the whole antibody (e.g., whole IgG). Such partial deficiency of the antibody molecule is accepted as long as the resultant antibody fragment is capable of binding to the DLL3 antigen. It is preferred that the antibody fragment according to the present invention should contain one or both of heavy chain variable (VH) and light chain variable (VL) regions. It is also preferred that the antibody fragment according to the present invention should contain CDRs. The number of CDRs contained in the antibody fragment of the present invention is not particularly limited and is preferably at least 6 CDRs: heavy chain CDR1, CDR2, and CDR3 and light chain CDR1, CDR2, and CDR3.

The amino acid sequence of VH or VL can contain substitution, deletion, addition, and/or insertion. Furthermore, the antibody fragment of the present invention may be deficient in a portion of one or both of VH and VL as long as the resultant antibody fragment is capable of binding to the DLL3 antigen. Moreover, its variable region may be chimerized or humanized. Specific examples of the antibody fragment can include Fab, Fab', F(ab')2, and Fv. Moreover, specific examples of the low-molecular antibody can include Fab, Fab', F(ab')2, Fv, scFv (single chain Fv), Diabody, sc(Fv)2 (single chain (Fv)2), and scFv-Fc. In the present invention, the low-molecular antibody is preferably Diabody or sc(Fv)2. These antibody multimers (e.g., dimmers, trimers, tetramers, and polymers) are also encompassed by the low-molecular antibody of the present invention.

Such fragments of the antibody can be obtained by enzymatically treating the antibody to form antibody fragments. The digestive enzymes cleave the antibody fragment at a particular position to give antibody fragments having a particular structure. For example, papain, pepsin, or plasmin is known in the art as the enzyme for forming the antibody fragments. The papain digestion gives F(ab)2 or Fab, while the pepsin digestion gives F(ab')2 or Fab'. Alternatively, genes encoding these antibody fragments are constructed, and these genes can be introduced into expression vectors and then expressed in appropriate host cells (see e.g., Co, M. S. et al., J. Immunol. (1994) 152, 2968-2976, Better, M. & Horwitz, A. H. Methods in Enzymology (1989) 178, 476-496, Plueckthun, A. & Skerra, A. Methods in Enzymology (1989) 178, 497-515, Lamoyi, E., Methods in Enzymology (1986) 121, 652-663, Rousseaux, J. et al., Methods in Enzymology (1986) 121, 663-669, Bird, R. E. et al., TIBTECH (1991) 9, 132-137).

The use of a genetic engineering approach for the enzymatically obtained antibody fragments can delete an arbitrary portion of the antibody. The low-molecular antibody according to the present invention may lack an arbitrary region as long as the resulting antibody fragment has binding affinity for DLL3.

i) Diabody

The Diabody refers to a bivalent antibody fragment constructed by gene fusion (e.g., Holliger P et al., Proc. Natl. Acad. Sci. USA 90: 6444-6448 (1993), EP404,097, and WO 93/11161). The Diabody is a dimer comprising two polypeptide chains. Usually, each of the polypeptide chains constituting the dimer comprises heavy and light chain variable regions linked via a linker on the same chain. The linker in the Diabody is generally too short to allow paring between heavy and light chain variable regions on the same chain. Specifically, the number of amino acid residues constituting the linker is, for example, approximately 5 residues. Therefore, heavy and light chain variable regions encoded on the same polypeptide chain cannot together form a single chain variable region fragment. Instead, they form a dimer by pairing with another single chain variable region fragment. As a result, the Diabody has two antigen-binding sites.

ii) scFv

The scFv is obtained by linking heavy and light chain variable regions of the antibody. In the scFv, the heavy and light chain variable regions are linked via a linker, preferably, a peptide linker (Huston, J. S. et al., Proc. Natl. Acad. Sci. U.S.A, 1988, 85, 5879-5883). The heavy and light chain variable regions in the scFv can be derived from any of the antibodies described in the present specification. The peptide linker that links the variable regions is not particularly limited. For example, an arbitrary single chain peptide of approximately 3 to 25 residues can be used as the linker. Specifically, for example, a peptide linker described later can be used.

The variable regions of both the chains can be linked, for example, by PCR. First, of DNA sequences encoding the heavy chain or heavy chain variable region of the antibody and DNA sequences encoding the light chain or light chain variable region of the antibody, DNAs encoding the whole or desired partial amino acid sequence are used as templates for linking the variable regions by PCR.

The heavy chain variable region-encoding DNA and the light chain variable region-encoding DNA are separately amplified by PCR using a pair of primers having sequences corresponding to both terminal sequences of each DNA to be amplified. Subsequently, DNA encoding the peptide linker portion is prepared. The DNA encoding the peptide linker can also be synthesized using PCR. Nucleotide sequences that can be linked to the amplification product of each variable region separately synthesized are respectively added to the 5' sequences of primers used in this PCR. Subsequently, PCR reaction is performed using each DNA of [heavy chain variable region DNA]-[peptide linker DNA]-[light chain variable region DNA] and primers for assembly PCR.

The primers for assembly PCR comprise the combination of a primer annealing to the 5' sequence of the [heavy chain variable region DNA] and a primer annealing to the 3' sequence of the [light chain variable region DNA]. Specifically, the primers for assembly PCR are a primer set that is capable of amplifying DNA encoding the full-length sequence of the scFv to be synthesized. By contrast, the [peptide linker DNA] contains an additional nucleotide sequence that can be linked to each variable region DNA. As a result, these DNAs are linked and, further, finally prepared into a full-length scFv amplification product using the primers for assembly PCR. Once the scFv-encoding DNA is prepared, expression vectors containing this DNA and cells transformed with the expression vectors (recombinant cells) can be obtained according to a routine method. Moreover, the resultant recombinant cells can be cultured for the expression of the scFv-encoding DNA to obtain the scFv.

iii) scFv-Fc

The scFv-Fc is a low-molecular antibody comprising an Fc region fused to scFv (Cellular & Molecular Immunology 2006; 3: 439-443). The origin of the scFv used in the scFv-Fc is not particularly limited, and, for example, scFv derived from IgM can be used. Moreover, the origin of the Fc is not particularly limited, and, for example, Fc derived from human IgG (human IgG1, etc.) can be used. Thus, examples of a preferable aspect of the scFv-Fc can include scFv-Fc comprising an IgM antibody scFv fragment linked to human IgG1 CH2 (e.g., Cγ2) and CH3 (e.g., Cγ3) via the hinge region (Hγ) of human IgG1.

iv) sc(Fv)2

The sc(Fv)2 is a low-molecular antibody having a single chain comprising two heavy chain variable regions (VHs) and two light chain variable regions (VLs) linked via linkers or the like (Hudson et al., J Immunol. Methods 1999; 231: 177-189). The sc(Fv)2 can be prepared, for example, by linking scFvs via a linker. Three linkers are usually necessary for linking four antibody variable regions.

Moreover, the sc(Fv)2 is preferably an antibody wherein two VHs and two VLs are aligned as VH, VL, VH, and VL (i.e., [VH]-linker-[VL]-linker-[VH]-linker-[VL]) in this order starting at the N-terminus of the single chain polypeptide.

The order of two VHs and two VLs is not particularly limited to the arrangement described above and may be any order of arrangement. Examples thereof can also include the following arrangements:

[VL]-linker-[VH]-linker-[VH]-linker-[VL]

[VH]-linker-[VL]-linker-[VL]-linker-[VH]

[VH]-linker-[VH]-linker-[VL]-linker-[VL]

[VL]-linker-[VL]-linker-[VH]-linker-[VH]

[VL]-linker-[VH]-linker-[VL]-linker-[VH]

For example, an arbitrary peptide linker or synthetic compound linker (e.g., linkers disclosed in the reference Protein Engineering, 9 (3), 299-305, 1996) that can be introduced by genetic engineering can be used as the linker that links the antibody variable regions. A plurality of the same or different linkers may be used. In the present invention, the peptide linker is preferable. The length of the peptide linker is not particularly limited and can be selected appropriately by those skilled in the art according to the purpose. The number of amino acid residues constituting the peptide linker is usually 1 to 100 amino acids, preferably 3 to 50 amino acids, more preferably 5 to 30 amino acids, particularly preferably 12 to 18 amino acids (e.g., 15 amino acids).

The amino acid sequence constituting the peptide linker can be an arbitrary sequence as long as this sequence does not inhibit the binding effect of the scFv. For example, the following amino acid sequences can be used for the peptide linker:

```
Ser

Gly · Ser

Gly · Gly · Ser

Ser · Gly · Gly

Gly · Gly · Gly · Ser (SEQ ID NO: 61)

Ser · Gly · Gly · Gly (SEQ ID NO: 62)

Gly · Gly · Gly · Gly · Ser (SEQ ID NO: 63)

Ser · Gly · Gly · Gly · Gly (SEQ ID NO: 64)

Gly · Gly · Gly · Gly · Gly · Ser (SEQ ID NO: 65)

Ser · Gly · Gly · Gly · Gly · Gly (SEQ ID NO: 66)

Gly · Gly · Gly · Gly · Gly · Gly · Ser
(SEQ ID NO: 67)

Ser · Gly · Gly · Gly · Gly · Gly · Gly
(SEQ ID NO: 68)

(Gly · Gly · Gly · Gly · Ser)n (Ser · Gly · Gly · Gly · Gly)n
[n represents an integer of 1 or more].
```

The amino acid sequence of the peptide linker can be selected appropriately by those skilled in the art according to the purpose. For example, the integer n that determines the length of the peptide linker is usually 1 to 5, preferably 1 to 3, more preferably 1 or 2.

Accordingly, examples of a particularly preferable aspect of the sc(Fv)2 according to the present invention can include the following sc(Fv)2: [VH]-peptide linker (15 amino acids)-[VL]-peptide linker (15 amino acids)-[VH]-peptide linker (15 amino acids)-[VL].

Alternatively, the variable regions can also be linked using the chemically synthesized linker (chemical cross-linking agent). Cross-linking agents usually used in the cross-link of peptide compounds or the like can be used in the present invention. For example, chemical cross-linking agents as shown below are known in the art. These cross-linking agents are commercially available:

N-hydroxysuccinimide (NHS),
disuccinimidyl suberate (DSS),
bis(sulfosuccinimidyl) suberate (BS3),
dithiobis(succinimidyl propionate) (DSP),
dithiobis(sulfosuccinimidyl propionate) (DTSSP),
ethylene glycol bis(succinimidyl succinate) (EGS),
ethylene glycol bis(sulfosuccinimidyl succinate) (sulfo-EGS),
disuccinimidyl tartrate (DST), disulfosuccinimidyl tartrate (sulfo-DST),
bis[2-(succinimidoxycarbonyloxy)ethyl]sulfone (BSOCOES), and
bis[2-(sulfosuccinimidoxycarbonyloxy)ethyl]sulfone (sulfo-BSOCOES), etc.

Activity of Anti-DLL3 Antibody (1) Cytotoxic Activity

For the treatment of cell-proliferative disease such as cancer, it is preferred that the antibody should maintain its effector activity. Specifically, the preferable antibody according to the present invention has both of a binding affinity for DLL3 and effector functions. The effector functions of the antibody encompass an antibody-dependent cell-mediated cytotoxic (ADCC) activity and a complement-dependent cytotoxic (CDC) activity. The therapeutic antibody according to the present invention particularly preferably possesses an ADCC activity as effector functions.

The antibody of the present invention used for the therapeutic purpose is preferably an antibody having a cytotoxic activity.

Examples of the cytotoxic activity according to the present invention can include ADCC and CDC activities. In the present invention, the ADCC activity means the activity of damaging target cells through the binding of Fcγ receptor-bearing cells (immunocytes, etc.) via the Fcγ receptors to the Fc domains of antibodies specifically attached to the cell surface antigens of the target cells. On the other hand, the CDC activity means a cytotoxic activity mediated by the complement system.

Whether or not the anti-DLL3 antibody has an ADCC activity or has a CDC activity can be determined by a method known in the art (e.g., Current protocols in Immunology, Chapter 7. Immunologic studies in humans, Editor, John E, Coligan et al., John Wiley & Sons, Inc., (1993)). Specifically, effector cells, a complement solution, and target cells are first prepared.

i) Preparation of Effector Cells

The spleens are excised from CBA/N mice or the like, and spleen cells are separated therefrom in an RPMI1640 medium (manufactured by Invitrogen Corp.). The cells can be washed with this medium containing 10% fetal bovine serum (FBS, manufactured by HyClone Laboratories, Inc.) and then adjusted to a cell concentration of $5 \times 10^6$ cells/ml to prepare effector cells.

ii) Preparation of Complement Solution

Baby Rabbit Complement (manufactured by CEDARLANE Laboratories Ltd.) can be diluted 10-fold with a medium (manufactured by Invitrogen Corp.) containing 10% FBS to prepare a complement solution.

iii) Preparation of Target Cell

Cells expressing DLL3 proteins can be cultured at 37° C. for 1 hour, together with 0.2 mCi $^{51}$Cr-sodium chromate (manufactured by GE Healthcare Bio-Sciences Corp.), in a DMEM medium containing 10% FBS to radiolabel the target cells. Cells transformed with DLL3 protein-encoding genes, small-cell lung cancer cell lines, or the like can be used as the cells expressing DLL3 proteins. The cells thus radiolabeled can be washed three times with an RPMI1640 medium containing 10% FBS and adjusted to a cell concentration of $2 \times 10^5$ cells/ml to prepare the target cells.

The ADCC or CDC activity can be assayed by a method described below. For the ADCC activity assay, the target cells and the anti-DLL3 antibody (50 μl each) are added to a U-bottom 96-well plate (manufactured by Becton, Dickinson and Company) and reacted for 15 minutes on ice. Then, 100 μl of the effector cells is added to the plate, and the cells are cultured for 4 hours in a $CO_2$ incubator. The final concentration of the antibody is set to 0 or 10 μg/ml. After the culture, 100 μl of the supernatant is collected, and the radioactivity is measured using a gamma counter (COBRA II AUTO-GAMMA, MODEL D5005, manufactured by Packard Instrument Company). The cytotoxic activity (%) can be calculated based on the calculation formula $(A-C)/(B-C) \times 100$ using the obtained value. In the formula, A represents radioactivity (cpm) from each sample; B represents radioactivity (cpm) from a sample supplemented with 1% NP-40 (manufactured by Nacalai Tesque, Inc.); and C represents radioactivity (cpm) from a sample containing only the target cells.

On the other hand, for the CDC activity assay, the target cells and the anti-DLL3 antibody (50 μl each) are added to a flat-bottomed 96-well plate (manufactured by Becton, Dickinson and Company) and reacted for 15 minutes on ice. Then, 100 μl of the complement solution is added to the plate, and the cells are cultured for 4 hours in a $CO_2$ incubator. The final concentration of the antibody is set to 0 or 3 μg/ml. After the culture, 100 μl of the supernatant is collected, and the radioactivity is measured using a gamma counter. The cytotoxic activity can be calculated in the same way as in the ADCC activity assay.

By contrast, in the cytotoxic activity assay using antibody conjugates, the target cells and the anti-DLL3 antibody conjugates (50 μl each) are added to a flat-bottomed 96-well plate (manufactured by Becton, Dickinson and Company) and reacted for 15 minutes on ice. The cells are cultured for 1 to 4 hours in a $CO_2$ incubator. The final concentration of the antibody is set to 0 or 3 μg/ml. After the culture, 100 μl of the supernatant is collected, and the radioactivity is measured using a gamma counter. The cytotoxic activity can be calculated in the same way as in the ADCC activity assay.

(2) Conjugated Antibody

The antibody may be conjugated with a cytotoxic substance such as a chemotherapeutic agent, a toxic peptide, or a radioactive chemical. Such a modified antibody (hereinafter, referred to as an antibody conjugate) can be obtained by chemically modifying the obtained antibody. A method for the antibody modification has already been established in the art.

Examples of the chemotherapeutic agent whose cytotoxic activity functions through the conjugation to the anti-DLL3 antibody can include the following chemotherapeutic agents: azaribine, anastrozole, azacytidine, bleomycin, bortezomib, bryostatin-1, busulfan, camptothecin, 10-hydroxycamptothecin, carmustine, celebrex, chlorambucil, cisplatin, irinotecan, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin, ethinyl estradiol, estramustine, etoposide, etoposide glucuronide, floxuridine, fludarabine, flutamide, fluorouracil, fluoxymesterone, gemcitabine, hydroxyprogesterone caproate, hydroxyurea, idarubicin, ifosfamide, leucovorin, lomustine, mechlorethamine, medroxyprogesterone acetate, megestrol acetate, melphalan, mercaptopurine, methotrexate, mitoxantrone, mithramycin, mitomycin, mitotane, phenylbutyrate, prednisone, procarbazine, paclitaxel, pentostatin, semustine, streptozocin, tamoxifen, taxanes, taxol, testosterone propionate, thalidomide, thioguanine, thiotepa, teniposide, topotecan, uracil mustard, vinblastine, vinorelbine, vincristine.

The chemotherapeutic agent is preferably a low-molecular chemotherapeutic agent. The low-molecular chemotherapeutic agent is unlikely to interfere with the antibody functions even after its conjugation to the antibody. In the present invention, the low-molecular chemotherapeutic agent usually has a molecular weight of 100 to 2000, preferably 200 to 1000. All of the chemotherapeutic agents exemplified above are low-molecular chemotherapeutic agents. These chemotherapeutic agents according to the present invention encompass prodrugs that are converted in vivo to active chemotherapeutic agents. The prodrug activation may be enzymatic conversion or nonenzymatic conversion.

Moreover, the antibody may be modified with the toxic peptide. Examples of the toxic peptide can include the following: Diphtheria toxin A Chain (Langone J. J., et al., Methods in Enzymology, 93, 307-308, 1983), Pseudomonas Exotoxin (Nature Medicine, 2, 350-353, 1996), Ricin A Chain (Fulton R. J., et al., J. Biol. Chem., 261, 5314-5319, 1986; Sivam G., et al., Cancer Res., 47, 3169-3173, 1987; Cumber A. J. et al., J. Immunol. Methods, 135, 15-24, 1990; Wawrzynczak E. J., et al., Cancer Res., 50, 7519-7562, 1990; Gheeite V., et al., J. Immunol. Methods, 142, 223-230, 1991); Deglicosylated Ricin A Chain (Thorpe P. E., et al., Cancer Res., 47, 5924-5931, 1987); Abrin A Chain (Wawrzynczak E. J., et al., Br. J. Cancer, 66, 361-366, 1992; Wawrzynczak E. J., et al., Cancer Res., 50, 7519-7562, 1990; Sivam G., et al., Cancer Res., 47, 3169-3173, 1987; Thorpe P. E., et al., Cancer Res., 47, 5924-5931, 1987); Gelonin (Sivam G., et al., Cancer Res., 47, 3169-3173, 1987; Cumber A. J. et al., J. Immunol. Methods, 135, 15-24, 1990; WawrzynczakE. J., et al., Cancer Res., 50, 7519-7562, 1990; Bolognesi A., et al., Clin. exp. Immunol., 89, 341-346, 1992); PAP-s; Pokeweed anti-viral protein fromseeds (Bolognesi A., et al., Clin. exp. Immunol., 89, 341-346, 1992); Briodin (Bolognesi A., et al., Clin. exp. Immunol., 89, 341-346, 1992); Saporin (Bolognesi A., et al., Clin. exp. Immunol., 89, 341-346, 1992); Momordin (Cumber A. J., et al., J. Immunol. Methods, 135, 15-24, 1990; Wawrzynczak E. J., et al., Cancer Res., 50, 7519-7562, 1990; Bolognesi A., et al., Clin. exp. Immunol., 89, 341-346, 1992); Momorcochin (Bolognesi A., et al., Clin. exp. Immunol., 89, 341-346, 1992); Dianthin 32 (Bolognesi A., et al., Clin. exp. Immunol., 89, 341-346, 1992); Dianthin 30 (Stirpe F., Barbieri L., FEBS letter 195, 1-8, 1986); Modeccin (Stirpe F., Barbieri L., FEBS letter 195, 1-8, 1986); Viscumin (Stirpe F., Barbieri L., FEBS letter 195, 1-8, 1986); Volkesin (Stirpe F., Barbieri L., FEBS letter 195, 1-8, 1986); Dodecandrin (Stirpe F., Barbieri L., FEBS letter 195, 1-8, 1986); Tritin (Stirpe F., Barbieri L., FEBS letter 195, 1-8, 1986); Luffin (Stirpe F., Barbieri L., FEBS letter 195, 1-8, 1986); Trichokirin (Casellas P., et al., Eur. J. Biochem. 176, 581-588, 1988; Bolognesi A., et al., Clin. exp. Immunol., 89, 341-346, 1992).

In the present invention, the radioactive chemical refers to a chemical containing a radioisotope. The radioisotope is not particularly limited, and any radioisotope may be used. For example, $^{32}P$, $^{14}C$, $^{125}I$, $^{3}H$, $^{131}I$, $^{186}Re$, or $^{188}Re$ can be used.

In another aspect, one or two or more low-molecular chemotherapeutic agents and one or two or more toxic peptides can be used in combination in the antibody modification. The anti-DLL3 antibody can be conjugated to the low-molecular chemotherapeutic agent via a covalent or noncovalent bond. A method for preparing such a chemotherapeutic agent-conjugated antibody is known in the art.

A proteinous agent or toxin can be conjugated to the antibody by a genetic engineering approach. Specifically, for example, DNA encoding the toxic peptide and DNA encoding the anti-DLL3 antibody are fused in frame with each other, and this fused DNA can be incorporated into expression vectors to construct recombinant vectors. The vectors are introduced into appropriate host cells, and the resultant transformed cells are cultured. The DNA insert can be expressed by the cells to obtain toxic peptide-conjugated anti-DLL3 antibodies as fusion proteins. For obtaining antibody-fusion proteins, the proteinous agent or toxin is generally located on the C-terminal side of the antibody. A peptide linker may be allowed to intervene between the antibody and the proteinous agent or toxin.

(3) Bispecific Antibody

Furthermore, the antibody of the present invention may be a bispecific antibody. The bispecific antibody refers to an antibody having, in the same antibody molecule, variable regions that recognize different epitopes. In the present invention, the bispecific antibody can have antigen-binding sites that recognize different epitopes on the DLL3 molecule. Thus, two such bispecific antibody molecules can bind to one DLL3 molecule. As a result, stronger cytotoxic effect can be expected.

Alternatively, the bispecific antibody of the present invention may have antigen-binding sites, one of which recognizes DLL3 and the other of which recognizes a cytotoxic substance. The cytotoxic substance specifically encompasses, for example, a chemotherapeutic agent, a toxic peptide, and a radioactive chemical. Such a bispecific antibody binds to cells expressing DLL3, while it captures the cytotoxic substance. As a result, the cytotoxic substance can be allowed to directly act on the cells expressing DLL3. Specifically, the bispecific antibody that recognizes the cytotoxic substance can specifically damage tumor cells and inhibit the growth of the tumor cells.

Moreover, in the present invention, a bispecific antibody comprising a DLL3-binding site combined with an antigen-binding site that recognizes an antigen other than DLL3 may be used. The antigen-binding site that can be combined therewith in such a bispecific antibody recognizes, for example, an antigen that is specifically expressed on the surface of target cancer cells, as with DLL3, but is different from DLL3.

A method for producing the bispecific antibody is known in the art. For example, two antibodies differing in antigen recognized thereby can be bound to prepare the bispecific antibody. Each of the antibodies bound may be a ½ molecule having heavy and light chains or may be a ¼ molecule consisting of heavy chains. Alternatively, different monoclonal antibody-producing hybridomas may be fused to prepare fusion cells producing bispecific antibodies. Furthermore, the bispecific antibody can be prepared by a genetic engineering approach.

The antigen binding activity of the antibody can be determined using means known in the art (Antibodies A Laboratory Manual. Ed Harlow, David Lane, Cold Spring Harbor Laboratory, 1988). For example, ELISA (enzyme-linked immunosorbent assay), EIA (enzyme immunoassay), RIA (radioimmunoassay), or fluoroimmunoassay can be used.

(4) Modification of Sugar Chain

The antibody of the present invention may be an antibody having a modified sugar chain. It is known that the cytotoxic activities of antibodies can be enhanced by modifying their sugar chains. For example, glycosylated antibodies (WO 99/54342, etc.), antibodies deficient in fucose added to their sugar chains (WO 00/61739, WO 02/31140, etc.), and antibodies having a sugar chain having bisecting GlcNAc (WO 02/79255, etc.) are known in the art as the antibody having a modified sugar chain.

(5) Internalization Activity

Moreover, the antibody of the present invention may have an internalization activity. In the present invention, the "antibody having an internalization activity" means an antibody that is transported into cells (cytoplasms, vesicles, other organelles, etc.) through its binding to DLL3.

Whether or not the antibody has an internalization activity can be confirmed by a method generally known by those skilled in the art and can be confirmed by, for example, a method involving contacting labeling material-bound anti-DLL3 antibodies with DLL3-expressing cells and confirming whether or not the labeling material is incorporated into the cells, or a method involving contacting cytotoxic substance-conjugated anti-DLL3 antibodies with DLL3-expressing cells and confirming whether or not the death of the DLL3-expressing cells is induced.

More specifically, the internalization activity of the anti-DLL3 antibody can be assayed by, for example, a method described in Examples.

The antibody having an internalization activity can be conjugated with, for example, the cytotoxic substance and used as a pharmaceutical composition such as an anticancer agent described later.

Preparation of Anti-DLL3 Antibody

1. Preparation of Anti-DLL3 Antibody Using Monoclonal Antibody-Producing Hybridoma Monoclonal antibody-producing hybridomas can be prepared according to a technique known in the art as follows: first, animals are immunized with DLL3 proteins or partial peptides thereof (which will be described later) used as sensitizing antigens according to a usual immunization method. The obtained immunocytes are fused with parental cells known in the art by a usual cell fusion method to obtain hybridomas. These hybridomas are further screened for cells producing the antibody of interest by a usual screening method to select hybridomas producing the anti-DLL3 antibody. The desired anti-DLL3 monoclonal antibody is obtained from the selected hybridomas. Specifically, the anti-DLL3 monoclonal antibody is prepared as follows:

(1) Preparation of DLL3 Protein

First, DLL3 genes can be expressed to obtain DLL3 proteins used as sensitizing antigens for antibody obtainment. Specifically, the DLL3-encoding gene sequence is inserted into expression vectors known in the art, with which appropriate host cells are then transformed. Then, the human DLL3 proteins of interest are purified from the host cells or a culture supernatant thereof by a method known in the art. Purified natural DLL3 proteins or fusion proteins comprising the desired partial polypeptide of the DLL3 protein fused with a different polypeptide may be used as immunogens. For example, antibody Fc fragments, peptide tags, and so on can be used for producing the fusion proteins used as immunogens. Expression vectors for the fusion proteins can be prepared by fusing, in frame, two or more genes respectively encoding the desired polypeptide fragments and inserting this fusion gene into expression vectors. The method for preparing the fusion proteins is described in Molecular Cloning 2nd ed. (Sambrook, J. et al., Molecular Cloning 2nd ed., 9.47-9.58, Cold Spring Harbor Lab. Press, 1989).

The DLL3 proteins thus purified can be used as sensitizing antigens for the immunization of mammals. Partial peptides of DLL3 can also be used as sensitizing antigens. For example, the following peptides can be used as sensitizing antigens:

The region and size of the partial peptide of DLL3 used are not limited. The number of amino acids constituting the peptide serving as a sensitizing antigen is preferably at least 3 or more, for example, 5 or more or 6 or more. More specifically, peptides of 8 to 50 residues, preferably 10 to 30 residues can be used as sensitizing antigens.

(2) Immunization with DLL3 Protein

Mammals are immunized with the DLL3 proteins or partial peptides thereof as sensitizing antigens. The immunized mammals are not particularly limited. For obtaining the monoclonal antibody by the cell fusion method, it is preferred that the immunized animals should be selected in consideration of compatibility with the parental cells used in cell fusion. In general, rodents are preferable as the immunized animals. Specifically, mice, rats, hamsters, or rabbits can be used as the immunized animals. In addition, monkeys or the like may be used as the immunized animals.

These animals can be immunized with the sensitizing antigens according to a method known in the art. For example, a general method can involve immunizing the mammals with the sensitizing antigens by intraperitoneal or subcutaneous injection. Specifically, the sensitizing antigens are administered to the mammals several times at 4- to 21-day intervals. The sensitizing antigens are diluted with PBS (phosphate-buffered saline), saline, or the like at an appropriate dilution ratio and used in the immunization. Furthermore, the sensitizing antigens may be administered together with an adjuvant. For example, the antigens can be mixed with a Freund's complete adjuvant for emulsification to prepare sensitizing antigens. Moreover, an appropriate carrier can be used in the immunization with the sensitizing antigens. Particularly, when partial peptides having a small molecular weight are used as the sensitizing antigens, it is preferred that the sensitizing antigen peptides should be bound to carrier proteins such as albumin or keyhole limpet hemocyanin and used in the immunization.

(3) DNA Immunization

The monoclonal antibody can also be obtained by DNA immunization. The DNA immunization is an immunostimulation method involving: immunizing animals by the administration of vector DNA that has been constructed in a form capable of expressing antigenic protein-encoding genes in the immunized animals; and allowing the immunized animals to express the immunizing antigens in vivo. The DNA immunization can be expected to be superior to general immunization methods using the administration of protein antigens as follows:

it can provide immunostimulation with membrane protein (e.g., DLL3) structures maintained; and
it eliminates the need of purifying immunizing antigens.

For obtaining the monoclonal antibody of the present invention by the DNA immunization, first, animals are immunized by the administration of DLL3 protein expression vector DNA. DLL3-encoding DNA can be synthesized by a method known in the art such as PCR. The obtained DNA is inserted into appropriate expression vectors, with which animals are immunized by administration. For example, commercially available expression vectors such as pcDNA3.1 can be used as the expression vectors. Likewise, a method generally used can be used for administering the vectors to the animals. For example, gold particles with the expression vectors adsorbed onto can be inserted into cells using a gene gun to perform DNA immunization.

(4) Preparation of Hybridoma

A rise in the amount of the desired antibody is confirmed in the serum of the mammals thus immunized. Then, immunocytes are collected from the mammals and subjected to cell fusion. Particularly, spleen cells can be used as preferable immunocytes.

Mammalian myeloma cells are used in the cell fusion with the immunocytes. It is preferred that the myeloma cells should have an appropriate selection marker for screening. The selection marker refers to a character that can survive (or cannot survive) under particular culture conditions. For example, hypoxanthine-guanine phosphoribosyltransferase deficiency (hereinafter, abbreviated to HGPRT deficiency) or thymidine kinase deficiency (hereinafter, abbreviated to TK deficiency) is known in the art as the selection marker. Cells having the HGPRT or TK deficiency are sensitive to hypoxanthine-aminopterin-thymidine (hereinafter, abbreviated to HAT-sensitive). The HAT-sensitive cells are killed in a HAT selective medium because they cannot synthesize DNA. By contrast, these cells, when fused with normal cells, can grow even in the HAT selective medium because they can continue DNA synthesis by use of the salvage pathway of the normal cells.

The cells having the HGPRT or TK deficiency can be selected in a medium containing 6-thioguanine or 8-azaguanine (hereinafter, abbreviated to 8AG) for the HGPRT deficiency or 5'-bromodeoxyuridine for the TK deficiency. The normal cells are killed in such a medium because they incorporate these pyrimidine analogs into their DNAs. By contrast, the cells deficient in these enzymes can survive in the selective medium because they cannot incorporate the pyrimidine analogs therein. In addition, a selection marker called G418 resistance imparts, to cells, 2-deoxystreptamine antibiotic (gentamicin analog) resistance via a neomycin resistance gene. Various myeloma cells suitable for the cell fusion are known in the art. For example, the following myeloma cells can be used in the production of the monoclonal antibody according to the present invention:

P3 (P3x63Ag8. 653) (J. Immunol. (1979) 123, 1548-1550),
P3x63Ag8U. 1 (Current Topics in Microbiology and Immunology (1978) 81, 1-7),
NS-1 (Kohler. G. and Milstein, C. Eur. J. Immunol. (1976) 6, 511-519),
MPC-11 (Margulies. D. H. et al., Cell (1976) 8, 405-415),
SP2/0 (Shulman, M. et al., Nature (1978) 276, 269-270),
FO (de St. Groth, S. F. et al., J. Immunol. Methods (1980) 35, 1-21),
S194 (Trowbridge, I. S. J. Exp. Med. (1978) 148, 313-323),
R210 (Galfre, G. et al., Nature (1979) 277, 131-133) or the like.

Basically, the cell fusion of the immunocytes with the myeloma cells is performed according to a method known in the art, for example, the method of Kohler and Milstein et al. (Kohler. G. and Milstein, C., Methods Enzymol. (1981) 73, 3-46).

More specifically, the cell fusion can be performed, for example, in a usual nutrient culture medium in the presence of a cell fusion promoter. For example, polyethylene glycol (PEG) or hemagglutinating virus of Japan (HVJ) can be used as the fusion promoter. Furthermore, an auxiliary such as dimethyl sulfoxide can also be added thereto, if desired, for enhancing fusion efficiency.

The ratio between the immunocytes and the myeloma cells used can be set arbitrarily. For example, it is preferred that the amount of the immunocytes should be set to 1 to 10 times that of the myeloma cells. For example, an RPMI1640 or MEM culture medium suitable for the growth of the myeloma cell line as well as a usual culture medium used in this kind of cell culture can be used as the culture medium in the cell fusion. Furthermore, a solution supplemented with serum (e.g., fetal calf serum (FCS)) can be added to the culture medium.

For the cell fusion, the immunocytes and the myeloma cells are well mixed in the predetermined amounts in the culture medium and then mixed with a PEG solution preheated to approximately 37° C. to form the fusion cells (hybridomas) of interest. In the cell fusion method, for example, PEG with an average molecular weight on the order of 1000 to 6000 can usually be added at a concentration of 30 to 60% (w/v). Subsequently, the appropriate culture medium exemplified above is sequentially added to the hybridomas, and the mixture is centrifuged, followed by removal of the supernatant. This procedure is repeated to remove the cell fusion agents or the like unfavorable for hybridoma growth.

The hybridomas thus obtained can be selected by use of a selective culture medium appropriate for the selection marker of the myeloma cells used in the cell fusion. For example, the cells having the HGPRT or TK deficiency can be selected by culturing the hybridomas in a HAT culture medium (culture medium containing hypoxanthine, aminopterin, and thymidine). Specifically, when HAT-sensitive myeloma cells are used in the cell fusion, only cells successfully fused with normal cells can be grown selectively in the HAT culture medium. The culture using the HAT culture medium is continued for a time long enough to kill cells (non-fused cells) other than the hybridomas of interest. Specifically, the culture can generally be performed for a few days to a few weeks to select the hybridomas of interest. Subsequently, hybridomas producing the antibody of interest can be screened for and cloned as single clones by a usual limiting dilution method.

The screening of the antibody of interest and cloning as single clones thereof can be performed preferably by a screening method based on antigen-antibody reaction known in the art. For example, the antigens are bound to a carrier such as beads made of polystyrene or the like or a commercially available 96-well microtiter plate and reacted with the culture supernatant of the hybridomas. Subsequently, the carrier is washed and then reacted with enzyme-labeled secondary antibodies or the like. When the culture supernatant contains the antibody of interest reactive with the sensitizing antigens, the secondary antibodies bind to the carrier via this antibody. Finally, the secondary antibodies bound with the carrier can be detected to determine the presence of the antibody of interest in the culture supernatant. The hybridomas producing the desired antibody capable of binding to the antigen can be cloned by a limiting dilution method or the like. In this screening, the DLL3 proteins used in the immunization or DLL3 proteins substantially identical thereto can be used preferably as the antigens. For example, cell lines expressing DLL3, soluble DLL3, or the like can be used as the antigens.

A method described in International Publication No. WO 03/104453 may be used in the production of the antibody against human DLL3.

Moreover, in addition to the method for obtaining the hybridomas by immunizing non-human animals with the antigens, human lymphocytes may be sensitized with the antigens to obtain the antibody of interest.

Specifically, the human lymphocytes are first sensitized with the DLL3 proteins in vitro. Subsequently, the sensitized lymphocytes are fused with appropriate fusion partners. For example, human-derived myeloma cells capable of dividing throughout their lives can be used as the fusion partners (see Japanese Patent Publication No. 1-59878).

Furthermore, the anti-DLL3 human antibody can also be obtained by administering the DLL3 proteins as antigens to transgenic animals having all repertoires of human antibody genes or by immunizing the animals with DNA that has been constructed to express DLL3 in the animals. Antibody-producing cells from the immunized animals can be immortalized by treatment such as cell fusion with appropriate fusion partners or infection with Epstein-Barr virus. From the immortalized cells thus obtained, human antibodies against the DLL3 protein can be isolated (see International Publication Nos. WO 94/25585, WO 93/12227, WO 92/03918, and WO 94/02602). Furthermore, the immortalized cells can also be cloned as cells producing antibodies having the reaction specificity of interest. When transgenic animals are used as the immunized animals, the immune systems of the animals recognize human DLL3 as foreigners. Thus, the human antibodies against human DLL3 can be obtained easily.

(5) Obtainment of Monoclonal Antibody from Hybridoma

The monoclonal antibody-producing hybridomas thus prepared can be subcultured in a usual culture medium. Moreover, the hybridomas can also be stored over a long period in liquid nitrogen.

The hybridomas are cultured according to a usual method, and the monoclonal antibody of interest can be obtained from the culture supernatant thereof.

Alternatively, the hybridomas are administered to mammals compatible therewith and grown, and the monoclonal antibody can also be obtained in the form of ascitic fluids. The former method is suitable for obtaining highly pure antibodies.

2. Preparation of Anti-DLL3 Antibody by Genetic Engineering Approach (1) Cloning of Antibody Gene The antibody may be prepared by a genetic engineering approach using antibody genes cloned from antibody-producing cells. The cloned antibody genes can be incorporated into appropriate vectors and expressed as antibodies by the transformation of hosts. Methods for the antibody gene isolation, the introduction into vectors, and the transformation of host cells have already been established (see e.g., Vandamme, A. M. et al., Eur. J. Biochem. (1990) 192, 767-775).

For example, cDNAs encoding the variable regions of the anti-DLL3 antibody can be obtained from the anti-DLL3 antibody-producing hybridoma cells. For this purpose, usually, total RNAs are first extracted from the hybridomas. For example, the following methods can be used for mRNA extraction from the cells:

guanidine ultracentrifugation method (Chirgwin, J. M. et al., Biochemistry (1979) 18, 5294-5299), and AGPC method (Chomczynski, P. et al., Anal. Biochem. (1987) 162, 156-159).

The extracted mRNAs can be purified using mRNA Purification Kit (manufactured by GE Healthcare Bio-Sciences Corp.) or the like. Alternatively, a kit for directly extracting total mRNAs from cells is also commercially available, such as QuickPrep mRNA Purification Kit (manufactured by GE Healthcare Bio-Sciences Corp.). The total mRNAs may be obtained from the hybridomas using such a kit. From the obtained mRNAs, antibody variable region-encoding cDNAs can be synthesized using reverse transcriptase. In this procedure, arbitrary 15- to 30-base sequences selected from sequences common to the antibody genes can be used as primers. The cDNAs can be synthesized using AMV Reverse Transcriptase First-strand cDNA Synthesis Kit (manufactured by Seikagaku Corp.) or the like. Moreover, 5'-Ampli FINDER RACE Kit (manufactured by Clontech Laboratories, Inc.) and 5'-RACE PCR (Frohman, M. A. et al., Proc. Natl. Acad. Sci. USA (1988) 85, 8998-9002; and Belyaysky, A. et al., Nucleic Acids Res. (1989) 17, 2919-2932) can be used for the cDNA synthesis and amplification. Furthermore, appropriate restriction enzyme sites described later can be introduced into both ends of the cDNAs in the course of such cDNA synthesis.

From the obtained PCR products, the cDNA fragments of interest are purified and subsequently ligated with vector DNAs. The recombinant vectors thus prepared are introduced into *E. coli* or the like. After colony selection, the desired recombinant vectors can be prepared from *E. coli* that has formed the colony. Then, the cDNA can be sequenced by a method known in the art, for example, a dideoxynucleotide chain termination method.

Moreover, cDNA libraries may be used for obtaining the antibody variable region-encoding genes. First, cDNAs are synthesized with mRNAs extracted from the antibody-producing cells as templates to obtain cDNA libraries. A commercially available kit is conveniently used in the cDNA library synthesis. In actuality, mRNAs from only a small number of cells are obtained in very small amounts. Therefore, direct purification thereof results in low yields. Thus, carrier RNAs shown to be free from the antibody genes are usually added thereto, followed by mRNA purification. Alternatively, when RNAs can be extracted in given amounts from the antibody-producing cells, efficient extraction can be achieved without using carrier RNAs. The addition of the carrier RNAs may be unnecessary for RNA extraction from, for example, 10 or more or 30 or more, preferably 50 or more antibody-producing cells.

The antibody genes are amplified by PCR with the obtained cDNA libraries as templates. Primers for the PCR amplification of the antibody genes are known in the art. For example, primers for human antibody gene amplification can be designed based on the disclosure of the paper (J. Mol. Biol. (1991) 222, 581-597) or the like. These primers have a nucleotide sequence differing on an immunoglobulin subclass basis. Thus, when cDNA libraries whose subclass is unknown are used as templates, PCR is performed by selecting primers in consideration of every possibility.

Specifically, for example, for the purpose of obtaining human IgG-encoding genes, primers can be used, which are capable of amplifying each of genes encoding 71 to 74 heavy chains and κ and λ light chains. Primers annealing to a portion corresponding to the hinge region are generally used as 3' primers for amplifying IgG variable region genes. On the other hand, primers appropriate for each subclass can be used as 5' primers.

The PCR products obtained from the primers for gene amplification for these heavy and light chain subclasses are prepared as their respective independent libraries. The libraries thus synthesized can be used to reshape immunoglobulins comprising the heavy and light chains in combination. The antibody of interest can be screened for with the binding activities of the reshaped immunoglobulins for DLL3 as an index.

(2) Introduction of Antibody Gene into Host Cell

For producing the anti-DLL3 antibody, the cloned antibody genes can be incorporated into expression vectors such that these genes are expressed under the control of expression control regions. The expression control regions for antibody expression encompass, for example, enhancers and promoters. Subsequently, appropriate host cells can be transformed with these expression vectors to obtain recombinant cells expressing the anti-DLL3 antibody-encoding DNA.

For the antibody gene expression, the antibody heavy chain- and light chain-encoding DNAs can be incorporated separately in different expression vectors. The same host cell can be co-transfected with the heavy chain- and light chain-incorporated vectors and thereby allowed to express antibody molecules comprising the heavy and light chains. Alternatively, the heavy chain- and light chain-encoding DNAs may be incorporated in single expression vectors, with which host cells are transformed (see International Publication No. WO 94/11523).

Many combinations of hosts and expression vectors are known in the art for introducing the isolated antibody genes into appropriate hosts for antibody preparation. All of these expression systems can be applied to the present invention. When eukaryotic cells are used as the hosts, animal, plant, or fungus cells can be used. Specifically, examples of the animal cells that can be used in the present invention can include the following cells:

i) mammalian cells such as CHO, COS, myeloma, BHK (baby hamster kidney), Hela, Vero, HEK293, Ba/F3, HL-60, Jurkat, and SK-HEP1 cells;
ii) amphibian cells such as *Xenopus* oocytes; and
iii) insect cells such as: sf9, sf21, and Tn5 cells.

For the plant cells, antibody gene expression systems are known in the art, which involve cells derived from the genus *Nicotiana* (e.g., *Nicotiana tabacum*). Cultured callus cells can be used in the plant cell transformation.

Furthermore, the following cells can be used as the fungus cells:
cells derived from yeasts such as the genus *Saccharomyces* (e.g., *Saccharomyces cerevisiae*) and filamentous fungi of the genus *Pichia* (e.g., *Pichia pastoris*), and cell derived from the genus *Aspergillus* (e.g., *Aspergillus niger*).

Alternatively, antibody gene expression systems using prokaryotic cells are also known in the art. For example, when bacterial cells are used, bacterial cells derived from *E. coli*, *Bacillus subtilis*, or the like can be used in the present invention.

For the gene expression using mammalian cells, a useful promoter routinely used, the antibody gene to be expressed, and a poly A signal located 3'-downstream thereof can be ligated functionally. Examples of the promoter/enhancer can include a human cytomegalovirus immediate early promoter/enhancer.

In addition, for example, virus promoters/enhancers or mammalian cell-derived promoters/enhancers (e.g., human elongation factor 1α (HEF1α)) can be used in the antibody expression. Examples of the viruses whose promoter/enhancer can be used can specifically include retrovirus, polyomavirus, adenovirus, and simian virus 40 (SV40).

The SV40 promoter/enhancer can be used according to the method of Mulligan et al. (Nature (1979) 277, 108). Moreover, the HEF1α promoter/enhancer can be used easily in the gene expression of interest by the method of Mizushima et al. (Nucleic Acids Res. (1990) 18, 5322).

When antibodies are produced using animal cells, the signal sequence of the heavy or light chain gene of the antibody is preferably used as a signal sequence required for extracellular secretion. Moreover, the signal sequence of a secretory protein such as IL-3 or IL-6 may be used.

For the gene expression using *E. coli*, a useful promoter routinely used, a signal sequence for antibody secretion, and the antibody gene to be expressed can be ligated functionally. Examples of the promoter can include lacZ and araB promoters. The lacZ promoter can be used according to the method of Ward et al. (Nature (1989) 341, 544-546; and FASEBJ. (1992) 6, 2422-2427). Alternatively, the araB promoter can be used in the gene expression of interest by the method of Better et al. (Science (1988) 240, 1041-1043).

When antibodies are produced in *E. coli* periplasm, a pelB signal sequence (Lei, S. P. et al., J. Bacteriol. (1987) 169, 4379) may be used for antibody secretion. Then, the antibodies produced in the periplasm are separated and then refolded by use of protein denaturants such as urea and guanidine hydrochloride such that the resultant antibodies have the desired binding activity.

A replication origin derived from SV40, polyomavirus, adenovirus, bovine papillomavirus (BPV), or the like can be inserted in the expression vectors. Furthermore, a selection marker can be inserted in the expression vectors for increasing a gene copy number in the host cell systems. Specifically, selection markers can be used, such as aminoglycoside phosphotransferase (APH) gene, thymidine kinase (TK) gene, *E. coli* xanthine-guanine phosphoribosyltransferase (Ecogpt) gene, and dihydrofolate reductase (dhfr) gene.

(3) Obtainment of Antibody from Host Cell

The host cells are transformed with these expression vectors, and the transformed host cells are then cultured in vitro or in vivo to produce the antibody of interest. The culture of the host cells is performed according to a method known in the art. For example, a DMEM, MEM, RPMI1640, or IMDM culture medium can be used and may be used in combination with a solution supplemented with serum such as fetal calf serum (FCS).

The antibodies thus expressed and produced can be purified by using, alone or in appropriate combination, usual protein purification methods known in the art. For example, affinity or chromatography columns (e.g., protein A columns), filters, ultrafiltration, salting-out, and dialysis can be selected and combined appropriately to separate and purify the antibodies (Antibodies A Laboratory Manual. Ed Harlow, David Lane, Cold Spring Harbor Laboratory, 1988).

Thus, the present invention provides a gene encoding the antibody of the present invention. The present invention also provides a vector comprising the gene. The present invention further provides a host cell carrying the vector. The present invention further provides a method for producing an antibody encoded by the gene, comprising the step of culturing the host cell.

3. Antibody Production by Transgenic Animal

In addition to the host cells, transgenic animals can also be used in the recombinant antibody production. Specifically, the antibody of interest can be obtained from animals transfected with the genes encoding this antibody of interest. For example, the antibody genes can be inserted in frame into genes encoding proteins specifically produced in milk to construct fusion genes. For example, goat β casein can be used as the proteins secreted into milk. DNA fragments containing the fusion genes having the antibody gene insert are injected into goat embryos, which are in turn introduced into female goats. From milk produced by transgenic goats (or progeny thereof) brought forth by the goats that have received the embryos, the desired antibody can be obtained as a fusion protein with the milk protein. Moreover, in the transgenic goats, hormone can be used appropriately for increasing the amount of milk containing the desired antibody produced from the transgenic goats (Ebert, K. M. et al., Bio/Technology (1994) 12, 699-702).

Pharmaceutical Composition

Since DLL3 is highly expressed in small-cell lung cancer tissues, the anti-DLL3 antibody has a cancer cell-specific cytotoxic activity. Thus, the anti-DLL3 antibody is useful in the treatment of cancer expressing DLL3.

Specifically, the present invention provides a pharmaceutical composition comprising an antibody which binds to DLL3 protein as an active ingredient. In an embodiment, the pharmaceutical composition is a cell growth inhibitor, particularly, an anticancer agent. Preferably, the cell growth inhibitor and the anticancer agent of the present invention are administered to a subject having cancer or possibly having cancer.

The anti-DLL3 antibody used in the pharmaceutical composition (e.g., anticancer agent) of the present invention is not particularly limited, and, for example, any of the anti-DLL3 antibodies described above can be used.

In the present invention, the phrase "comprising the antibody which binds to DLL3 as an active ingredient" means comprising the anti-DLL3 antibody as a main active ingredient and does not limit the content of the anti-DLL3 antibody.

The pharmaceutical composition of the present invention may comprise a cytotoxic substance-conjugated anti-DLL3 antibody as an active ingredient. This pharmaceutical composition can be used as, for example, a cell growth inhibitor, particularly, an anticancer agent. Preferably, the cell growth inhibitor and the anticancer agent of the present invention are administered to a subject having cancer or possibly having cancer.

In the present invention, the phrase "comprising the cytotoxic substance-conjugated anti-DLL3 antibody as an active ingredient" means comprising the cytotoxic substance-conjugated anti-DLL3 antibody as a main active ingredient and does not limit the content of the cytotoxic substance-conjugated anti-DLL3 antibody.

When the disease targeted by the pharmaceutical composition of the present invention is cancer, the targeted cancer is not particularly limited and is preferably lung cancer, particularly, small-cell lung cancer. The cancer may be any of primary foci and metastatic foci.

The pharmaceutical composition of the present invention can be administered either orally or parenterally to a patient. Parenteral administration is preferable. Specific examples of such an administration method include injection, transnasal, pulmonary, and transdermal administrations. Examples of the injection administration include intravenous, intramuscular, intraperitoneal, and subcutaneous injections, through which the pharmaceutical composition of the present invention can be administered systemically or locally. Moreover, the administration method can be selected appropriately according to the age or symptoms of the patient. The dose of the pharmaceutical composition of the present invention can be selected from among a dose range of, for example, 0.0001 mg to 1000 mg per kg body weight per dosing. Alternatively, the dose can be selected from among a range of, for example, 0.001 to 100000 mg per body. However, the pharmaceutical composition of the present invention is not limited to these doses.

The pharmaceutical composition of the present invention can be formulated according to a standard method (e.g., Remington's Pharmaceutical Science, latest edition, Mark Publishing Company, Easton, U.S.A) and may additionally contain pharmaceutically acceptable carriers or additives. Examples thereof include, but not limited thereto, surfactants, excipients, coloring agents, flavoring agents, preservatives, stabilizers, buffers, suspending agents, tonicity agents, binders, disintegrants, lubricants, flow promoters, and corrigents. Other carriers routinely used can be used appropriately. Specific examples of the carriers can include light anhydrous silicic acid, lactose, crystalline cellulose, mannitol, starch, carmellose calcium, carmellose sodium, hydroxypropylcellulose, hydroxypropylmethylcellulose, polyvinyl acetal diethylaminoacetate, polyvinyl pyrrolidone, gelatin, middle chain fatty acid triglyceride, polyoxyethylene hydrogenated castor oil 60, white sugar, carboxymethylcellulose, corn starch, and inorganic salts.

Upon contact with DLL3-expressing cells, the anti-DLL3 antibody of the present invention can damage the DLL3-expressing cells or inhibit their growth. Such a method using the anti-DLL3 antibody is also incorporated in the scope of the present invention. The antibody used is not particularly limited, and, for example, any of the antibodies described above can be used. The cells to which the anti-DLL3 antibody binds are not particularly limited as long as the cells express DLL3. In the present invention, the DLL3-expressing cells are preferably cancer cells, more preferably lung cancer cells, particularly preferably small-cell lung cancer cells.

In the present invention, the "contact" is performed, for example, by adding the antibody to a culture medium of DLL3-expressing cells cultured in vitro. In the present invention, the "contact" is also performed by administering the anti-DLL3 antibody to non-human animals implanted with DLL3-expressing cells in their bodies or to animals endogenously having cancer cells expressing DLL3.

Methods shown below are preferably used for evaluating or determining cytotoxicity caused in the DLL3-expressing cells by the contact of the anti-DLL3 antibody. Examples of the methods for evaluating or determining the cytotoxic activity in vitro can include the ADCC or CDC activity assay described above. Whether or not the anti-DLL3 antibody has an ADCC activity or has a CDC activity can be determined by a method known in the art (e.g., Current protocols in Immunology, Chapter 7. Immunologic studies in humans, Editor, John E, Coligan et al., John Wiley & Sons, Inc., (1993)). In the activity assay, antibodies that have an isotype identical to that of the anti-DLL3 antibody and do not bind to the cells are used as control antibodies in the same way as in the anti-DLL3 antibody. When the anti-DLL3 antibody exhibits a stronger cytotoxic activity than that of the control antibodies, the anti-DLL3 antibody can be determined to have the activity.

The isotype of an antibody is defined based on the sequence of the heavy chain constant region in the amino acid sequence of this antibody. The antibody isotype is finally determined depending on class switching caused by genetic recombination on the chromosome during the maturation of antibody-producing B cells in vivo. Difference in isotype reflects difference between the physiological/pathological functions of antibodies. Specifically, it is known that, for example, the strength of the cytotoxic activity is influenced not only by antigen expression levels but by antibody isotypes. Thus, for the cytotoxic activity assay described above, it is preferred that the antibodies used as controls should have an isotype identical to that of the analyte antibody.

Moreover, for evaluating or determining the cytotoxic activity in vivo, for example, DLL3-expressing cancer cells are intradermally or subcutaneously transplanted to non-human test animals. Then, the analyte antibody is intravenously or intraperitoneally administered thereto on a daily basis or at a few day-intervals from the administration day or the next day. The cytotoxic activity can be determined by measuring tumor sizes over time. Control antibodies having an isotype identical thereto are administered in the same way in the in vitro evaluation. When the anti-DLL3 antibody-administered group has a significantly smaller tumor size than that of the control antibody-administered group, the anti-DLL3 antibody can be determined to have the cytotoxic activity. When mice are used as the non-human test animals, nude (nu/nu) mice can be used preferably, which are genetically deficient in thymus gland and thus lack the functions of T lymphocytes. The use of these mice can exclude the involvement of the endogenous T lymphocytes of the test animals in the evaluation/determination of the cytotoxic activity of administered antibodies.

Diagnostic Drug (Diagnosis Method)

The present invention also provides a method for diagnosing cancer, comprising detecting the DLL3 protein or a gene encoding the DLL3 protein. DLL3 expression has been confirmed to be remarkably increased in cancer tissues or cancer cell lines. Thus, DLL3 is useful as a marker for specific detection of cancer.

One specific example of the diagnosis method of the present invention can include a method for diagnosing cancer, comprising the following steps:

(a) providing a sample isolated from a test subject; and (b) detecting the expression level of DLL3 protein or DLL3 gene in the sample.

The method of the present invention may further comprise the step of (c) evaluating the possibility that the test subject has cancer, based on the expression level of the DLL3 protein or the DLL3 gene.

Detection of DLL3 Protein or Gene Encoding DLL3 Protein

In one aspect of the method of the present invention, cancer is diagnosed by detecting the DLL3 protein in a sample. It is preferred that the DLL3 protein detection should be performed using an antibody that recognizes the DLL3 protein.

In the present invention, the detection encompasses quantitative or qualitative detection. Examples of the qualitative detection can include the following assays:

assay to simply determine the presence or absence of the DLL3 protein, assay to determine the presence or absence of more than a predetermined amount of the DLL3 protein, and assay to compare the amount of the DLL3 protein with that contained in another sample (e.g., a control sample).

On the other hand, examples of the quantitative detection can include measurement of a DLL3 protein concentration and measurement of the amount of the DLL3 protein.

The test sample according to the present invention is not particularly limited as long as the sample is likely to contain the DLL3 protein. Specifically, samples collected from living bodies such as mammals are preferable. Samples collected from humans are more preferable. Specific examples of the test sample can include blood, interstitial fluid, plasma, extravascular fluid, cerebrospinal fluid, synovial fluid, pleural fluid, serum, lymph, saliva, urine, and tissues. The sample is preferably a sample obtained from the test sample, such as a preparation in which tissues or cells collected from a living body are fixed, or a cell culture medium.

The cancer diagnosed by the present invention may be any cancer without particular limitations. Specific examples thereof can include lung cancer, particularly, small-cell lung cancer. In the present invention, any of primary foci and metastatic foci of these cancers can be diagnosed.

In the present invention, when the protein is detected in the test sample, cancer is diagnosed with its level as an index. Specifically, when the amount of the DLL3 protein detected in the test sample is larger than that of a negative control or a healthy individual, the test subject is shown to have cancer or highly possibly have cancer in the future. Specifically, the present invention relates to a method for diagnosing cancer, comprising the following steps:

(1) detecting the expression level of DLL3 in a biological sample collected from a test subject, and (2) comparing the expression level of DLL3 detected in step (1) with that of a control, wherein when the expression level of DLL3 is higher than that of the control, the test subject is determined to have cancer.

In the present invention, the control refers to a reference sample for comparison and encompasses negative controls and biological samples of healthy individuals. The negative controls can be obtained by collecting biological samples of healthy individuals and mixing them, if necessary. The expression level of DLL3 in the control can be detected in parallel with the detection of the expression level of DLL3 in the biological sample of the test subject. Alternatively, the expression level of DLL3 in a large number of biological samples of healthy individuals can be detected in advance to statistically determine the standard expression level in the healthy individuals. Specifically, for example, mean±2× standard deviation (S.D.) or mean±3×standard deviation (S.D.) can also be used as the standard value. Statistically, the mean±2×standard deviation (S.D.) and the mean±3× standard deviation (S.D.) include values of 80% and 90% of the healthy individuals, respectively.

Alternatively, the expression level of DLL3 in the control can be set using an ROC curve. The ROC curve, or receiver operating characteristic curve, is a graph showing detection sensitivity in the ordinate and false positive rates (i.e., "1-specificity") in the abscissa. In the present invention, the ROC curve can be obtained by plotting changes in sensitivity and false positive rate at a series of varying reference values for determining the expression level of DLL3 in biological samples.

The "reference value" for obtaining the ROC curve is a numeric value temporarily used for statistical analysis. In general, the "reference value" for obtaining the ROC curve is serially varied within a range which can cover all selectable reference values. For example, the reference value can be varied between the minimal and maximal measured values of DLL3 in a population to be analyzed.

A standard value that can be expected to offer the desired detection sensitivity and precision can be selected based on the obtained ROC curve. The standard value statistically set based on the ROC curve or the like is also called a cut-off value. In a method for detecting cancer based on the cut-off value, step (2) described above comprises comparing the expression level of DLL3 detected in step (1), with the cut-off value. Then, when the expression level of DLL3 detected in step (1) is higher than the cut-off value, cancer is detected in the test subject.

In the present invention, the expression level of DLL3 can be determined by an arbitrary method. Specifically, the expression level of DLL3 can be determined by evaluating the amount of DLL3 mRNA, the amount of the DLL3 protein, or the biological activity of the DLL3 protein. The amount of the DLL3 mRNA or protein can be determined by a method as described in the present specification.

In the present invention, the test subject is particularly preferably a human. When a non-human animal is used as the test subject, the DLL3 protein to be detected is derived from this animal species.

A method for detecting the DLL3 protein contained in the test sample is not particularly limited and is preferably an immunological detection method using the anti-DLL3 antibody as exemplified below:

enzyme-linked immunosorbent assay (ELISA),
radioimmunoassay (RIA),
enzyme immunoassay (EIA),
fluoroimmunoassay (FIA),
luminescent immunoassay (LIA),
immunoprecipitation (IP),
turbidimetric immunoassay (TIA),
Western blotting (WB),
immunohistochemical (IHC) method,
single radial immunodiffusion (SRID),
dot blot, and
slot blot.

Among these approaches, the immunohistochemical (IHC) method is a preferable immunological assay method for diagnosing cancer, comprising the step of detecting DLL3 proteins in sections in which tissues or cells obtained from a patient having cancer are fixed. The immunological methods described above, such as the immunohistochemical (IHC) method, are generally known by those skilled in the art.

Since DLL3 is a membrane protein whose expression is enhanced in a cancer cell-specific manner, cancer cells or cancer tissues can be detected using the anti-DLL3 antibody. Cancer cells contained in cells or tissues collected from living bodies are detected by the immunohistological analysis.

In another preferable aspect, cancer tissues can also be detected in vivo using the anti-DLL3 antibody. This method specifically comprises the steps of: (1) administering, to a test subject, a labeling material (e.g., radioisotope)-labeled antibody which binds to DLL3 protein; and (2) detecting the accumulation of the labeling material. The antibody can be labeled detectably for tracing the antibody administered into the living body. For example, the antibody can be labeled with a fluorescent or luminescent material or a radioisotope, and its in vivo behavior can be traced. The antibody labeled with the fluorescent or luminescent material can be observed using an endoscope or peritoneoscope. The localization of the antibody can be imaged by tracing the radioactivity of the radioisotope. In the present invention, the in vivo localization of the anti-DLL3 antibody represents the presence of cancer cells.

A positron-emitting nuclide can be used as the radioisotope for labeling the antibody for in vivo cancer detection. For example, the antibody can be labeled with a positron-emitting nuclide such as 18F, 55Co, 64Cu, 66Ga, 68Ga, 76Br, 89Zr, and 124I. A method known in the art (Acta Oncol. 32, 825-830, 1993) can be used in the labeling of the anti-DLL3 antibody with these positron-emitting nuclides.

The anti-DLL3 antibody labeled with the positron-emitting nuclide is administered to humans or animals. Then, radiation emitted by the radionuclide is measured non-invasively using PET (positron emission tomograph) and converted to images by a computed tomographic approach. The PET apparatus is intended to noninvasively obtain data about in vivo drug behavior or the like. The PET can quantitatively image radiation intensity as signal intensity. By such use of the PET, antigen molecules highly expressed in particular cancer can be detected without collecting samples from patients. The anti-DLL3 antibody may be radiolabeled with a short-life nuclide using a positron-emitting nuclide such as 11C, 13N, 15O, 18F, and 45Ti, in addition to the nuclides described above.

Research and development have been pursued as to, for example, techniques of producing short-life nuclides using a medical cyclotron and the nuclides described above or producing short-life radiolabeling compounds. The anti-DLL3 antibody can be labeled with various radioisotopes by these techniques. The anti-DLL3 antibody administered to patients accumulates in primary foci and metastatic foci according to the specificity of the anti-DLL3 antibody for pathological tissues at each site. When the anti-DLL3 antibody is labeled with the positron-emitting nuclide, its radioactivity can be detected to detect the presence of the primary foci and the metastatic foci based on the localization of the radioactivity. An active value of gamma radiation or positron emission of 25 to 4000 keV can be used appropriately for the diagnostic use. Moreover, therapeutic effect can also be expected by selecting an appropriate nuclide and administering the selected nuclide in larger amounts. A nuclide that provides a value of gamma radiation or positron emission of 70 to 700 keV can be used for obtaining anticancer effect attributed to radiation.

Detection of Polynucleotide Encoding DLL3 Protein

In an alternative aspect of the method of the present invention, the expression of the DLL3 polynucleotide is detected. In the present invention, the detected polynucleotide is not particularly limited and is preferably mRNA. In the present invention, the detection encompasses quantitative or qualitative detection. Examples of the qualitative detection can include the following assay procedures:

assay to simply determine the presence or absence of the DLL3 mRNA, assay to determine the presence or absence of more than a predetermined amount of the DLL3 mRNA, and assay to compare the amount of the DLL3 mRNA with that contained in another sample (e.g., a control sample).

On the other hand, examples of the quantitative detection can include measurement of a DLL3 mRNA concentration and measurement of the amount of the DLL3 mRNA.

In the present invention, an arbitrary sample likely to contain the DLL3 mRNA can be used as the test sample. Samples collected from living bodies such as mammals are preferable. Samples collected from humans are more preferable. Specific examples of the test sample can include blood, interstitial fluid, plasma, extravascular fluid, cerebrospinal fluid, synovial fluid, pleural fluid, serum, lymph, saliva, urine, and tissues. The sample is preferably a sample obtained from the test sample, such as a preparation in which tissues or cells collected from a living body are fixed, or a cell culture medium. These samples are encompassed by the test sample of the present invention.

In situ hybridization is preferably used for the sample obtained from the test sample, such as a preparation in which tissues or cells collected from a living body are fixed, or a cell culture medium. The in situ hybridization has been evolved as an approach for confirming the presence or absence or distribution of particular DNA or RNA in cells or tissues, and the strength of its expression. This method employs the principles on which a probe nucleic acid having a nucleotide sequence complementary to an intracellular particular nucleic acid sequence has the property of specifically forming a complex. The probe is labeled in advance with a radioisotope (RI), an antigenic substance (hapten), or the like. As a result, the hybridization site can be distinguished through the detection of the label. Thus, the in situ hybridization is used in, for example, the detection of intracellular DNA or RNA, or the like. Preferably, RI can be used for the probe labeling. For example, fluorescence labeling with a nonradioactive substance such as biotin or hapten (e.g., digoxigenin) can be used more preferably. For example, a detection method by fluorescence in situ hybridization called FISH is particularly preferably used.

The cancer diagnosed in the present invention is not particularly limited. Specific examples thereof can include lung cancer, particularly, small-cell lung cancer. In the present invention, any of primary foci and metastatic foci of these cancers can be diagnosed.

In the present invention, an arbitrary animal species expressing the DLL3 gene can be used as the test subject. The test subject is particularly preferably a human. When a non-human animal species is used as the test subject, the DLL3 gene to be detected is derived from this animal species.

Hereinafter, a specific aspect of the detection method will be described. First, a sample is prepared from a test subject. Subsequently, DLL3 mRNA contained in the sample is detected. In the present invention, cDNA synthesized from the mRNA can also be detected. In the present invention, when DLL3 mRNA or DLL3-encoding cDNA is detected in the test sample, the test subject is diagnosed as possibly having cancer. For example, when the amount of the DLL3 mRNA or DLL3-encoding cDNA detected in the test sample is larger than that in negative controls or healthy individuals, the test subject is shown to have cancer or highly possible have cancer in the future.

A method for detecting the mRNA is known in the art. Specific examples of the method that can be used in the present invention include: nucleic acid hybridization using samples immobilized on a solid phase selected from gene chips, cDNA arrays, and membrane filters; RT-PCR; real-time PCR; subtraction method; differential display method; differential hybridization; and cross hybridization.

The detection method of the present invention may be automated using various automatic detectors. Such automation achieves detection of a large number of samples in a short time.

Kit for Cancer Diagnosis

The present invention also provides a diagnostic drug or a kit for cancer diagnosis, comprising a reagent for detecting DLL3 protein in a test sample. The diagnostic drug of the present invention comprises at least the anti-DLL3 antibody.

The reagent for cancer diagnosis of the present invention can be combined with other factors used in DLL3 detection to prepare a kit for cancer diagnosis. Specifically, the present invention relates to a kit for cancer diagnosis, which comprises: an antibody which binds to DLL3; and a reagent for detecting the binding of the antibody to DLL3 and may further comprise a control sample comprising a biological sample containing DLL3. A manual for instruction of assay procedures may further be included in the kit of the present invention.

EXAMPLES

Hereinafter, the present invention will be described more specifically with reference to Examples. However, the present invention is not intended to be limited to these Examples.

[Example 1] Increased Transcription of DLL3 (Delta-Like 3) in Small-Cell Lung Cancer The gene expression distribution of human DLL3 mRNA in clinical cancers, cancer cell lines, and various normal organs was analyzed using Human Exon 1.0 ST Array (Affymetrix, Inc.). In the expression analysis, the total RNAs used were derived from tumor sites in 13 cases of isolated small-cell lung cancer tissues, 3 types of small-cell lung cancer cell lines, and 49 types of normal tissues (purchased from Clontech Laboratories, Inc., Ambion, Inc., Stratagene Corp., Cell Applications, Inc., Panomics, Inc., CHEMICON, and BioChain Institute, Inc.). All of tumor sites in isolated clinical cancer tissues and cancer cell lines (purchased from ATCC) were subjected to total RNA extraction using Trizol (Invitrogen Corp.) according to the protocol included in the product. The experiment of gene expression analysis was conducted using 1 μg of each total RNA thus obtained according to GeneChip Whole Transcript (WT) Sense Target Labeling Assay Manual (Affymetrix, Inc.). Human Exon 1.0 ST Array Data was digitized using ExACT (Exon Array Computational Tool) software provided by Affymetrix, Inc.

13 core probe sets for DLL3 were present on Human Exon 1.0 ST Array. The mean of expression values was determined from these probe sets, and the gene expression level was compared among tissues. The expression data obtained from the normal tissues, the tumor sites in isolated small-cell lung cancer tissues, and the small-cell lung cancer cell lines is shown in FIG. 1.

It was found that human DLL3 gene expression was remarkably increased in the tumor sites in isolated small-cell lung cancer tissues and the small-cell lung cancer cell lines, compared with the normal tissues except for the fetal brain. These results promise the effectiveness of therapy using an antitumor agent molecularly targeting human DLL3, i.e., the possibility of reducing the size of tumor without damaging normal tissues.

[Example 2] cDNA Cloning and Preparation of Recombinant Cell

The human DLL3 cDNA (NM_016941) as set forth in SEQ ID NOs: 1 and 57 was amplified by PCR from a human fetal brain cDNA library and cloned into expression vectors pMCN for mammals. The pMCN vector achieves the expression of a foreign gene under the control of a mouse CMV promoter (GenBank: U68299). The pMCN vector has a Geneticin resistance gene. A CHO cell line DG44 (Invitrogen Corp.) was transformed with the human DLL3 expression vector. Drug-resistant cells were selected in the presence of Geneticin. Cloned cells stably expressing the human DLL3 protein were selected using commercially available anti-DLL3 antibodies (R&D Systems, Inc., MAB4315) to establish human DLL3/DG cells. Likewise, a mouse IL-3-dependent pro B cell line Ba/F3 was transformed the human DLL3 expression vector to establish human DLL3/BaF3 cells.

The mouse DLL3 cDNA (NM_007866) as set forth in SEQ ID NOs: 2 and 58 was amplified by PCR from a mouse fetal cDNA library and cloned into expression vectors pMCN for mammals. A cell line Ba/F3 was transformed with the mouse DLL3 expression vector. Drug-resistant cells were selected in the presence of Geneticin. Cells expressing the mouse DLL3 protein were selected using commercially available antibodies (R&D Systems, Inc., MAB4315) to establish mouse DLL3/BaF3 cells.

The human DLL1 cDNA (NM_005618) as set forth in SEQ ID NOs: 3 and 59 was amplified by PCR from a human spleen cDNA library and cloned into expression vectors pMCN for mammals. A cell line Ba/F3 was transformed with the human DLL1 expression vector. Drug-resistant cells were selected in the presence of Geneticin. Cells expressing the human DLL1 protein were selected using commercially available antibodies (R&D Systems, Inc., MAB1818) to establish human DLL1/BaF3 cells.

The human Notch1 cDNA (NM_017617) as set forth in SEQ ID NOs: 4 and 60 was amplified by PCR from a breast cancer cell line DU4475 cDNA library and cloned into expression vectors pMCN for mammals. A cell line DG44 was transformed with the human Notch1 expression vector. Drug-resistant cells were selected in the presence of Geneticin. Cells expressing the human Notch1 protein were selected using commercially available antibodies (GeneTex Inc., GTX23294) to establish human Notch1/DG44 cells.

Cell lines producing a soluble DLL3 protein or its N-terminal deletion variant protein were prepared for the purpose of obtaining immunogens for anti-DLL3 antibody obtainment and determining epitopes for the obtained antibodies. The human DLL3 extracellular sequence is composed of a Notch receptor-binding motif DSL domain (Nos. 176-215 in the amino acid sequence) and six EGF-like domains (1: 216-249, 2: 274-310, 3: 312-351, 4: 353-389, 5: 391-427, and 6: 429-465).

cDNA encoding a chimeric molecule human DLL3-Fc (SEQ ID NO: 5) consisting of a human DLL3 extracellular region (27-492 in the amino acid sequence of SEQ ID NO: 1) and mouse IgG2a antibody constant region sequences was prepared and cloned into expression vectors pMCN for mammals. A cell line DG44 was transformed with the human DLL3-Fc expression vector. Drug-resistant cells were selected in the presence of Geneticin. Clones highly expressing the human DLL3-Fc protein were selected by ELISA using anti-mouse antibodies to establish human DLL3-Fc-producing DG44 cells.

cDNA encoding a chimeric molecule human DLL3delta1-Fc (SEQ ID NO: 6) consisting of a partial sequence of the human DLL3 extracellular region (176-492 in the amino acid sequence of SEQ ID NO: 1) and mouse IgG2a antibody constant region sequences was prepared and cloned into expression vectors pMCN for mammals. A cell line DG44 was transformed with the human DLL3delta1-Fc expression vector. Drug-resistant cells were selected in the presence of Geneticin. Clones highly expressing the human DLL3delta1delta1-Fc protein were selected by ELISA using anti-mouse antibodies to establish human DLL3delta1-Fc-producing DG44 cells.

cDNA encoding a chimeric molecule human DLL3delta2-Fc (SEQ ID NO: 7) consisting of a partial sequence of the human DLL3 extracellular region (216-492 in the amino acid sequence of SEQ ID NO: 1) and mouse IgG2a antibody constant region sequences was prepared and cloned into expression vectors pMCN for mammals. A cell line DG44 was transformed with the human DLL3delta2-Fc expression vector. Drug-resistant cells were selected in the presence of Geneticin. Clones highly expressing the human DLL3delta1delta2-Fc protein were selected by ELISA using anti-mouse antibodies to establish human DLL3delta2-Fc-producing DG44 cells.

cDNA encoding a chimeric molecule mouse DLL3-Fc (SEQ ID NO: 8) consisting of a mouse DLL3 extracellular region (33-490 in the amino acid sequence of SEQ ID NO: 2) and mouse IgG2a antibody constant region sequences was prepared and cloned into expression vectors pMCN for mammals. A cell line DG44 was transformed with the mouse DLL3-Fc expression vector. Drug-resistant cells were selected in the presence of Geneticin. Clones highly expressing the mouse DLL3-Fc protein were selected by ELISA using an anti-mouse antibody to establish mouse DLL3-Fc-producing DG44 cells.

Each protein of interest was purified from the culture supernatant of the Fc fusion protein-producing cell line by Protein G affinity column chromatography and gel filtration chromatography. The concentration of the purified protein was determined by DC protein assay (Bio-Rad Laboratories, Inc.) with the IgG known for its concentration as a standard.

[Example 3] Obtainment of Anti-DLL3 Antibody and Analysis of Epitope and Antibody Internalization Six- to seven-week-old Balb/c (Charles River Laboratories Japan, Inc.) and MRL/MpJJmsSlc-lpr/lpr (Japan SLC, Inc.) mice were immunized. For the initial challenge, by prepared into an emulsion using a Freund's complete adjuvant (Becton, Dickinson and Company), the antigenic proteins were subcutaneously administered thereto at a dose of 0.1 mg human DLL3-Fc/head. Two weeks later, an antigen emulsion prepared using a Freund's incomplete adjuvant was subcutaneously administered thereto at a dose of 0.05 mg/head a total of 3 to 6 times on a once-a-week basis. 0.05 mg of the antigenic proteins was intravenously administered to each mouse individual confirmed to have a rise in antibody titer in its serum. Three days later, their spleen cells were extracted and mixed with mouse myeloma cells P3-X63Ag8U1 (ATCC) at a cell count ratio of approximately 3:1. These cells were fused by the polyethylene glycol (PEG) method. After removal of PEG by centrifugation, the cells were suspended in an RPMI1640 medium containing 1×HAT media supplement (Sigma-Aldrich Corp.), 0.5×BM-Condimed H1 Hybridoma cloning supplement (Roche Diagnostics GmbH), and 10% fetal bovine serum to adjust the cell concentration. Then, the cells were seeded to each well of a 96-well plate. Hybridoma colony formation was confirmed, and the presence or absence of anti-DLL3 antibodies contained in the culture supernatant was then analyzed by ELISA using a plate coated with human DLL3-Fc. Hybridoma cells contained in positive wells were cloned by the limiting dilution method to establish hybridoma lines producing the anti-DLL3 antibodies. The monoclonal antibodies were isotyped using IsoStrip (Roche Diagnostics GmbH).

Each IgG monoclonal antibody was purified from the culture supernatants of the established hybridomas by Protein G affinity column chromatography and desalting treatment. The concentration of the purified antibody was determined by DC protein assay.

Figure 2:
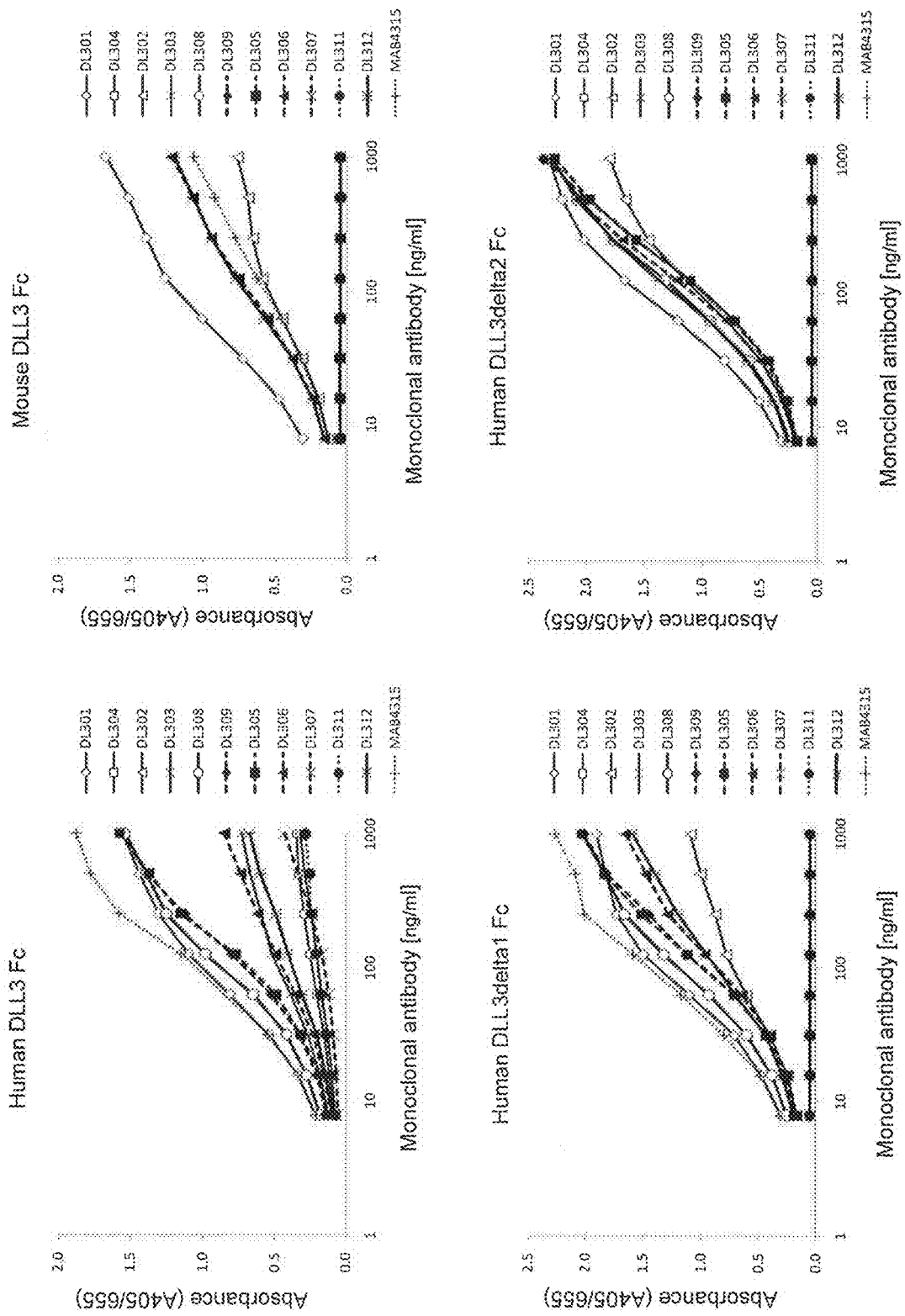
FIG. 2 shows the binding of an anti-DLL3 monoclonal antibody to a soluble DLL3 protein.
Figure 9:
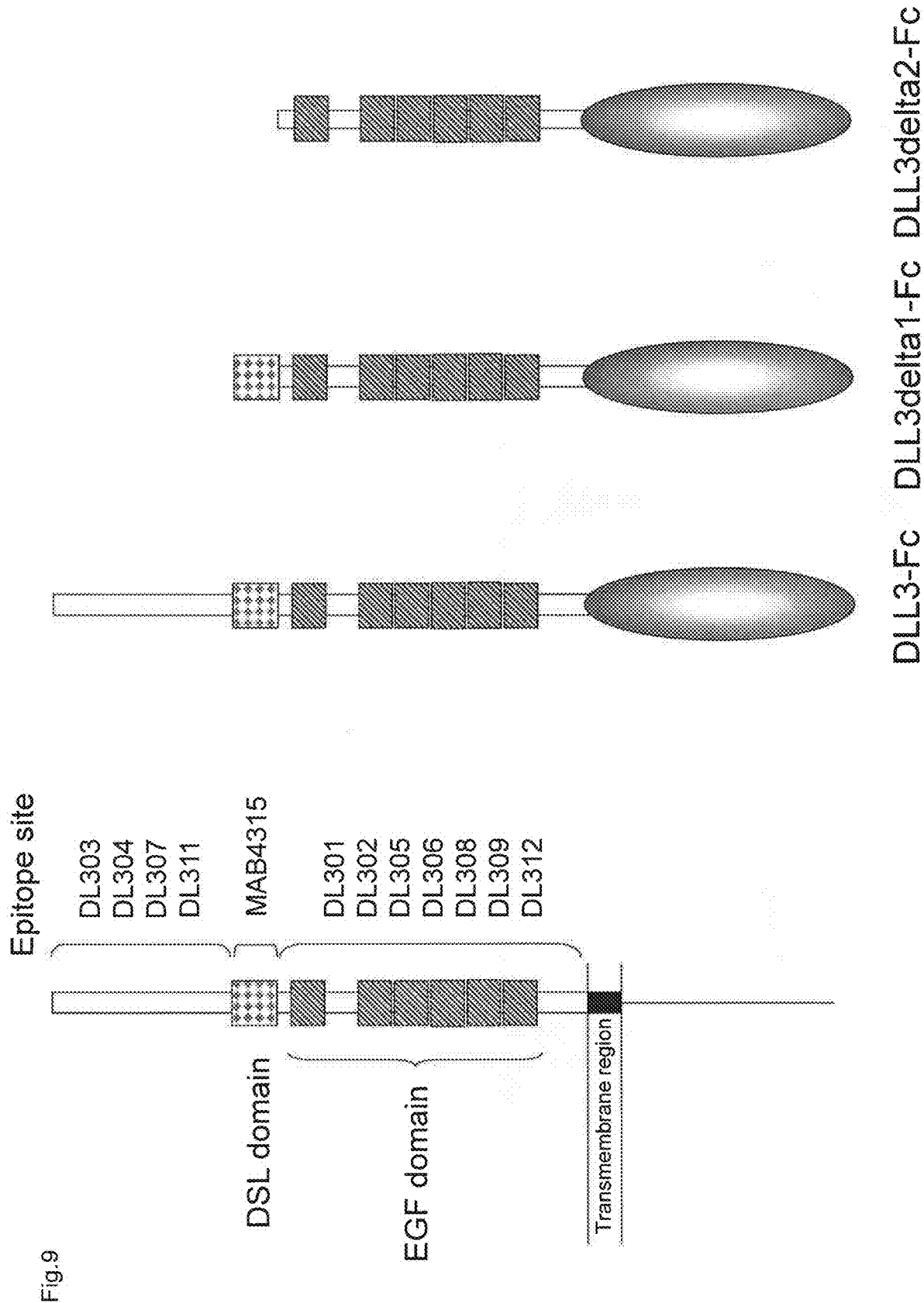
FIG. 9 shows the schematic structure of full-length and soluble DLL3 proteins and a site recognized by an anti-DLL3 antibody.

Human DLL3-Fc, mouse DLL3-Fc, human DLL3delta1-Fc, and human DLL3delta2-Fc were separately immobilized on a Nunc immunoplate (439454). Subsequently, the unreacted surface of the plate was blocked with a solution containing bovine serum albumin. After washing, each diluted antibody solution adjusted to an appropriate concentration was added thereto and incubated at room temperature for 1 hour. The reaction solution was removed from the plate. After washing with TBS containing Tween 20, alkaline phosphatase-labeled anti-mouse IgK antibodies were added to the plate and incubated for 1 hour. After washing of the plate, an alkaline phosphatase substrate Sigma 104 was added thereto and incubated at room temperature. After the incubation, the absorbance was measured at a wavelength of 405 nm and a reference wavelength of 655 nm. The results are shown in FIG. 2. All the purified antibodies bound to human DLL3-Fc in a dose-dependent manner. The monoclonal antibodies DL301, DL302, DL306, and DL312 and the commercially available antibody MAB4315 bound to mouse DLL3-Fc. The commercially available antibody MAB4315 bound to human DLL3delta1-Fc, but did not bind to human DLL3delta2-Fc, demonstrating that its epitope was located in the DSL domain. The DL303, DL304, DL307, and DL311 antibodies bound to neither human DLL3delta1-Fc nor human DLL3delta2-Fc. Thus, predicted epitopes for these antibodies are located between residues 27 and 175 in the amino acid sequence of SEQ ID NO: 1. DL301, DL302, DL305, DL306, DL308, DL309, and DL312 bound to both human DLL3delta1-Fc and human DLL3delta2-Fc, demonstrating that epitopes for these antibodies were located in residues 216-492 in the amino acid sequence of SEQ ID NO: 1. The schematic structure of the full-length DLL3 protein and the soluble DLL3-Fc fusion protein and a site recognized by each anti-DLL3 antibody are shown in FIG. 9.

Figure 3:
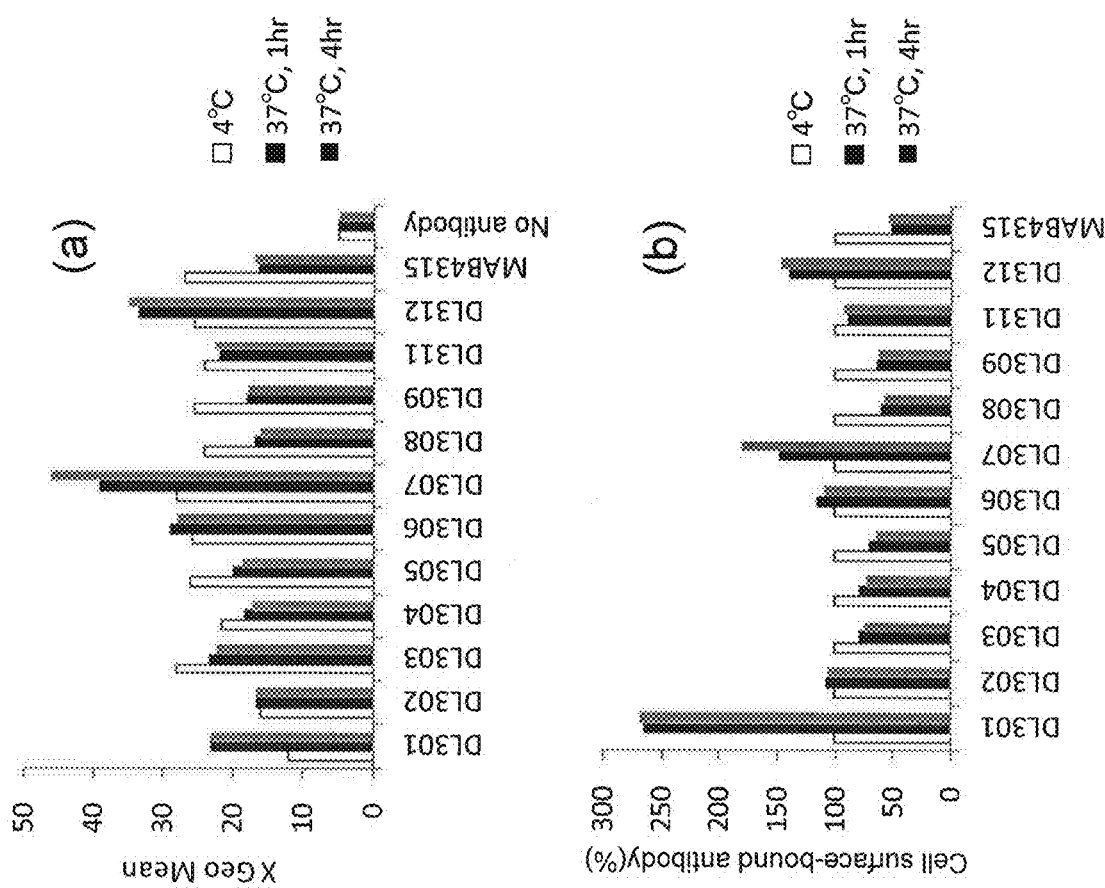
FIG. 3 shows the binding of an antibody to the DLL3 protein on a cell membrane and the turnover of the cell-bound antibody.

The binding of each monoclonal antibody to human DLL3 expressed on a cell membrane and the behavior of a human DLL3-monoclonal antibody complex on the cell membrane were analyzed by flow cytometry. Human DLL3/BaF3 cells were suspended in a FACS buffer (PBS containing 1% fetal bovine serum and 0.05% sodium azide). The cell suspension of 1×10⁶ cells/ml was reacted with the monoclonal antibody (final concentration: 5 µg/ml) at 4° C. for 30 minutes. After centrifugation and supernatant removal, the cells were washed once with a FACS buffer. FITC-labeled anti-mouse IgG (H+L) antibodies (Beckman Coulter, Inc.) were added thereto and incubated at 4° C. for 30 minutes. Unreacted FITC antibodies were removed by centrifugation. Then, the cells were resuspended and analyzed using a flow cytometer FACSCalibur (Becton, Dickinson and Company). For the purpose of analyzing the movement or disappearance of the DLL3-antibody complex from the cell membrane, human DLL3/BaF3 cells were suspended in an RPMI1640 culture medium containing 10% fetal bovine serum (FBS) and mouse IL3. The cell suspension of 1×10⁶ cells/ml was mixed with the monoclonal antibody (final concentration: 5 µg/ml) and reacted at 37° C. for 1 hour or 4 hours in a CO2 incubator. After the reaction, the amount of the antibody bound onto the cell membrane was analyzed by flow cytometry in the same way as above. The geometric mean of fluorescence intensity values (X Geo Mean) in a cell histogram plot was determined using the analytical software CELLQuest Pro included in FACSCalibur. All the isolated anti-DLL3 monoclonal antibodies bound to DLL3 on the cells (FIG. 3(*a*)). The reaction of the antibody with the cells at 4° C. inhibits membrane fluidity such as the cellular uptake of the DLL3-antibody complex from the cell membrane. The reaction of the antibody with the cells at 37° C. may cause the cellular uptake of the DLL3-antibody complex and shading (release from the cell membrane) resulting from protease digestion or the like. The amount of each monoclonal antibody bound onto the cell membrane as a result of incubation at 37° C. for 1 hour or 4 hours is shown in FIG. 3(*b*) as a relative value compared with that at 4° C. As a result of incubation at 37° C., the amount of the antibody DL303, DL304, DL305, DL308, DL309, or MAB4315 on the surface of the cell membrane was decreased. These results suggest the internalization or shading of the DLL3-antibody complex. By contrast, as a result of incubation at 37° C., the amount of the antibody DL301, DL306, DL307, DL311, or DL312 on the surface of the cell membrane was hardly changed or was increased, on the contrary. The latter result demonstrated that these antibodies were able to stably reside in the form of a DLL3 complex on the cell membrane.

The number of the DLL3 protein on cell surface was determined using a QIFIKIT (DAKO, F0479) for the quantitative determination of cell surface antigen by flow cytometry. The analysis was conducted with the anti-DLL3 antibody DL303 (final concentration: 5 µg/ml) as a primary antibody according to the protocol included therein. The numbers of the antigen on the surfaces of the human DLL3/BaF3, NCI-H1184 (ATCC), NCI-H1436 (ATCC), and Y79 (Riken Cell Bank) cells were approximately 9000, 7000, 6000, and 3000, respectively.

[Example 4] Induction of ADCC Activity by Anti-DLL3 Antibody and Growth Inhibition Mediated by Antibody-Toxin Complex Each anti-DLL3 antibody was examined for its antibody-dependent cell-mediated cytotoxicity (ADCC)-inducing activity against DLL3-expressing cells labeled with calcein. DLL3-expressing human DLL3/BaF3 and small-cell lung cancer NCI-H1184 (ATCC) cell lines were separately cultured for 90 minutes in the presence of 20 µg/ml Calcein-AM (Dojindo, 349-07201), then centrifuged, and washed to prepare calcein-labeled target cells. The target cells were seeded at 1×10⁴ cells/well to a 96-well plate (Coster 3799). Subsequently, the antibody adjusted to an appropriate final concentration was added thereto and incubated at room temperature for 15 minutes. Effector cells were added thereto at 5×10⁴ cells/well. The reaction plate was incubated at 37° C. in a CO2 incubator. The effector cells used were NK92 cells expressing a mouse FcγR3-human FcγR3 chimeric molecule (WO 2008/093688). After 4-hour incubation, the plate was centrifuged, and 100 µl of the culture supernatant was collected from each well. The fluorescence intensity was measured using ARVO SX (Wallac).

The ADCC-inducing activity was calculated according to the following formula:

$$ADCC\ [\%] = (A-C)/(B-C) \times 100,$$

wherein

Figure 4:
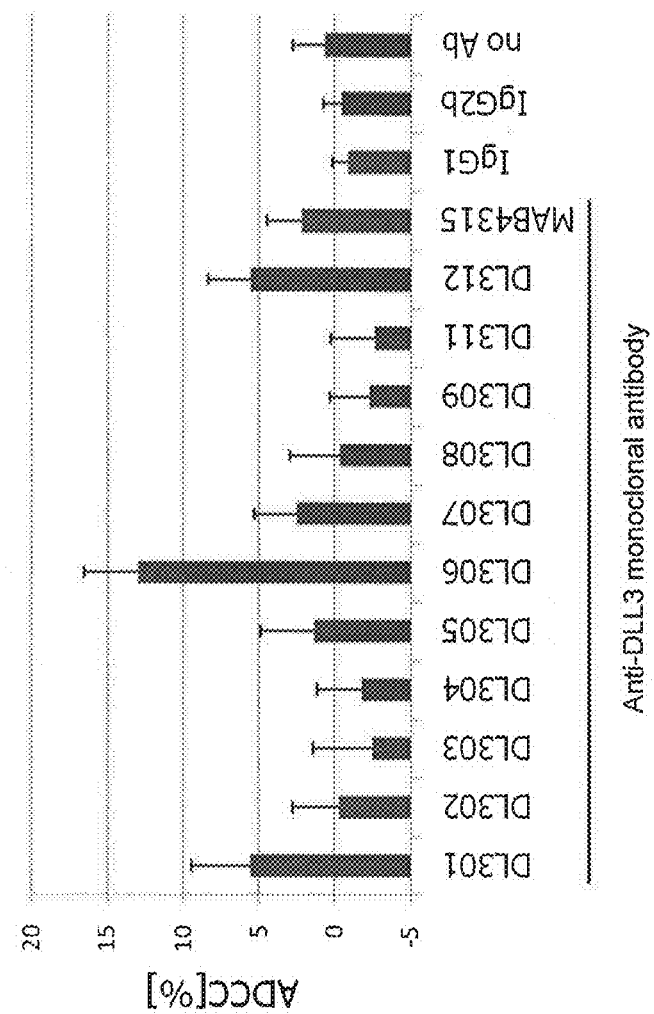
FIG. 4 shows the induction of ADCC by an anti-DLL3 antibody (concentration: 2.5 µg/ml).

A represents fluorescence intensity in each well; B represents the mean of fluorescence intensity in the supernatant of cells lysed with Nonidet P-40 with the final concentration of 1%; and C represents the mean of fluorescence intensity in a well supplemented with only a medium. The mean and standard deviation were calculated from three measurements under each experimental condition. FIG. 4 shows the ADCC-inducing activity of the antibody added at the final concentration of 2.5 µg/ml against the DLL3/BaF3 cells. No ADCC activity was confirmed control antibodies IgG1 and IgG2b, whereas the ADCC-inducing activity was confirmed in DL301, DL306, and DL312. No distinct ADCC-inducing activity was confirmed in the commercially available monoclonal antibody MAB4315. FIG. 5 shows that the DL301, DL306, and D312 antibodies induce ADCC against DLL3/BaF3 and NCI-H1184 in a dose-dependent manner.

Figure 6:
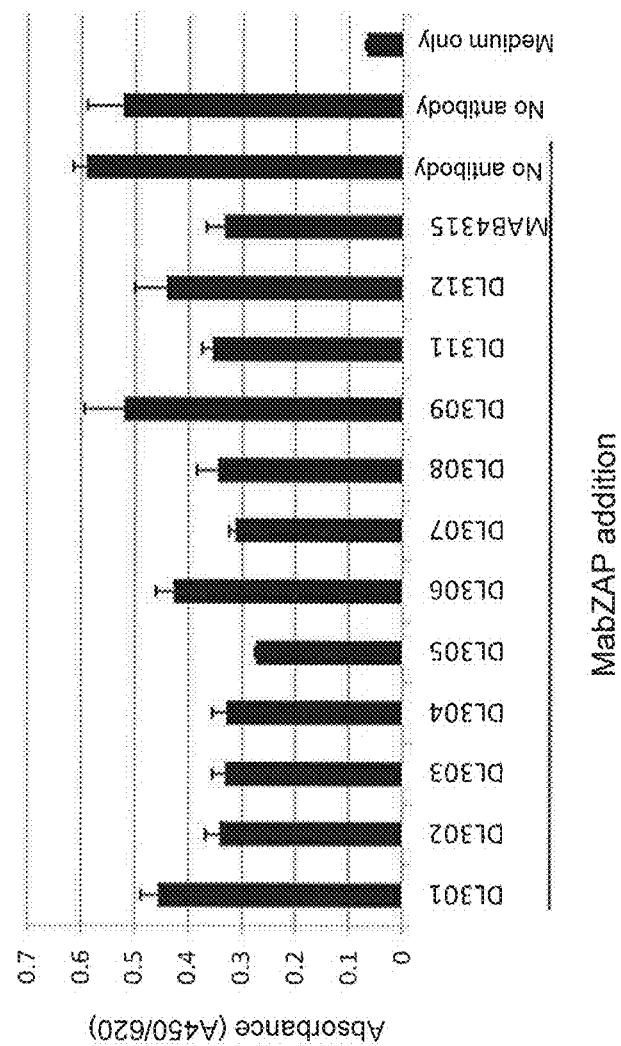
FIG. 6 shows the inhibition of cell growth by the uptake of an anti-DLL3 antibody and an anti-mouse secondary antibody Mab-ZAP labeled with toxin.

Each anti-DLL3 monoclonal antibody was evaluated for its cellular uptake using a toxin-labeled anti-mouse secondary antibody Mab-ZAP (Advanced Targeting Systems). DLL3/BaF3 cells were seeded at 5×10³ cells/well to a 96-well plate. Subsequently, the anti-DLL3 mouse monoclonal antibody and Mab-ZAP (final concentration: 1 µg/ml) were added thereto and incubated at 37° C. in a CO2 incubator. Four days later, Cell Count Reagent SF (Nacalai Tesque, Inc.) was added thereto. The absorbance was measured at 450 nm and at a control wavelength of 620 nm using a microplate reader to determine cell growth (FIG. 6). The addition of the anti-DLL3 monoclonal antibody and Mab-ZAP to the cells inhibited cell growth. The DL301, DL306, and DL312 antibodies confirmed to have an ADCC-inducing activity remained in large amounts on DLL3-expressing cells after being mixed with the cells and cultured at 37° C., and exhibited low growth inhibitory effect brought about by the cellular uptake of the Mab-ZAP complex.

[Example 5] Cloning of Antibody Variable Region and Preparation of Recombinant Antibody A Smart 5'-RACE cDNA library (Clontech Laboratories, Inc.) was prepared from the total RNAs of hybridomas producing each anti-DLL3 antibody. The total RNA preparation was performed using RNeasy Mini column (Qiagen). The cDNA library preparation followed the instruction of the manufacturer. Sequences encoding antibody variable regions (VH and VL) were amplified by PCR using primers complementary to sequences encoding antibody constant regions. The fragments thus amplified by PCR were cloned into pCR2.1TOPO and sequenced. Chimeric antibody expression vectors containing the obtained VH- and VL-encoding sequences and human IgG1 constant region-encoding sequences were constructed. The light chain- and heavy chain-encoding sequences were both incorporated in one expression vector for mammalian cells and transcribed under the control of a mouse CMV promoter. Table 1 shows SEQ ID NOs of the identified antibody variable region sequences and their CDR sequences, full-length mouse antibody sequences, and chimeric antibody sequences.

body to the immobilized protein was analyzed. For detecting antigen-bound chimeric antibodies, the chimeric antibody was added thereto, and alkaline phosphatase-labeled anti-human antibodies (Biosource, AHI0305) and an alkaline phosphatase substrate Sigma 104 were then added in this order. The absorbance was determined. The DL301, DL309,

TABLE 1

| | | CDR1 | CDR2 | CDR3 | Variable region sequence |
|---|---|---|---|---|---|
| DL301 | Heavy chain | NYLIE (SEQ ID NO: 12) | VMNPGSGGTHYSEKFRG (SEQ ID NO: 13) | SDYDYVTYAMDY (SEQ ID NO: 14) | (SEQ ID NO: 9) |
| | Light chain | KASQDINSYLI (SEQ ID NO: 18) | RTNRLVD (SEQ ID NO: 19) | LQYDEFPFT (SEQ ID NO: 20) | (SEQ ID NO: 15) |
| DL306 | Heavy chain | DYYMK (SEQ ID NO: 24) | DINPNNGDTFYNQKFKG (SEQ ID NO: 25) | DGNYAYFDY (SEQ ID NO: 26) | (SEQ ID NO: 21) |
| | Light chain | RASKSVSTSGYSYMH (SEQ ID NO: 30) | LASNLES (SEQ ID NO: 31) | QHSRHLPWT (SEQ ID NO: 32) | (SEQ ID NO: 27) |
| DL309 | Heavy chain | NYYIE (SEQ ID NO: 36) | EILPGSGSTTYNEKFKG (SEQ ID NO: 37) | WGAREPGFPY (SEQ ID NO: 38) | (SEQ ID NO: 33) |
| | Light chain | KASQNVGTNVA (SEQ ID NO: 42) | SASYRYS (SEQ ID NO: 43) | QQYNNYPLT (SEQ ID NO: 44) | (SEQ ID NO: 39) |
| DL312 | Heavy chain | DYYMN (SEQ ID NO: 48) | LIRNKANGYTTEYNASVKG (SEQ ID NO: 49) | DSDGYYEYYFDY (SEQ ID NO: 50) | (SEQ ID NO: 45) |
| | Light chain | RASQEISDYLS (SEQ ID NO: 54) | AASTLDS (SEQ ID NO: 55) | LQYASYPYT (SEQ ID NO: 56) | (SEQ ID NO: 51) |

| | | Mouse antibody sequence | Chimeric antibody sequence |
|---|---|---|---|
| DL301 | Heavy chain | (SEQ ID NO: 10) | (SEQ ID NO: 11) |
| | Light chain | (SEQ ID NO: 16) | (SEQ ID NO: 17) |
| DL306 | Heavy chain | (SEQ ID NO: 22) | (SEQ ID NO: 23) |
| | Light chain | (SEQ ID NO: 28) | (SEQ ID NO: 29) |
| DL309 | Heavy chain | (SEQ ID NO: 34) | (SEQ ID NO: 35) |
| | Light chain | (SEQ ID NO: 40) | (SEQ ID NO: 41) |
| DL312 | Heavy chain | (SEQ ID NO: 46) | (SEQ ID NO: 47) |
| | Light chain | (SEQ ID NO: 52) | (SEQ ID NO: 53) |

COS-7 cells were transfected with each chimeric antibody expression vector and allowed to transiently express the chimeric antibody. The chimeric antibody in the culture supernatant of COS-7 was confirmed to bind to the human DLL3 protein by flow cytometry and ELISA. The chimeric antibody concentration in the culture supernatant of COS-7 was calculated by sandwich ELISA. In this concentration calculation, a human chimeric antibody known for its concentration was used as a standard. The chimeric antibody (final concentration: 1 µg/ml) was added to human DLL3/BaF3 cells suspended in a FACS buffer (PBS containing 1% fetal bovine serum). After incubation at 4° C. for 30 minutes and washing, the cells were reacted with FITC-labeled anti-human antibodies (Beckman Coulter, Inc.), and the binding of the chimeric antibody was analyzed using a flow cytometer FACSCalibur. As shown in FIG. 7, the chimeric antibodies DL301, DL309, and DL312 bound to human DLL3/BaF3. None of the chimeric antibodies bound to Ba/F3 cells, which were a parental line of the forced expressing cells. Human DLL3-Fc was immobilized on a Nunc immunoplate, and the binding of each chimeric antiand DL312 chimeric antibodies bound to human DLL3-Fc in a dose-dependent manner (FIG. 8(a)).

[Example 6] Grouping of Epitope by Competitive ELISA

Figure 8:
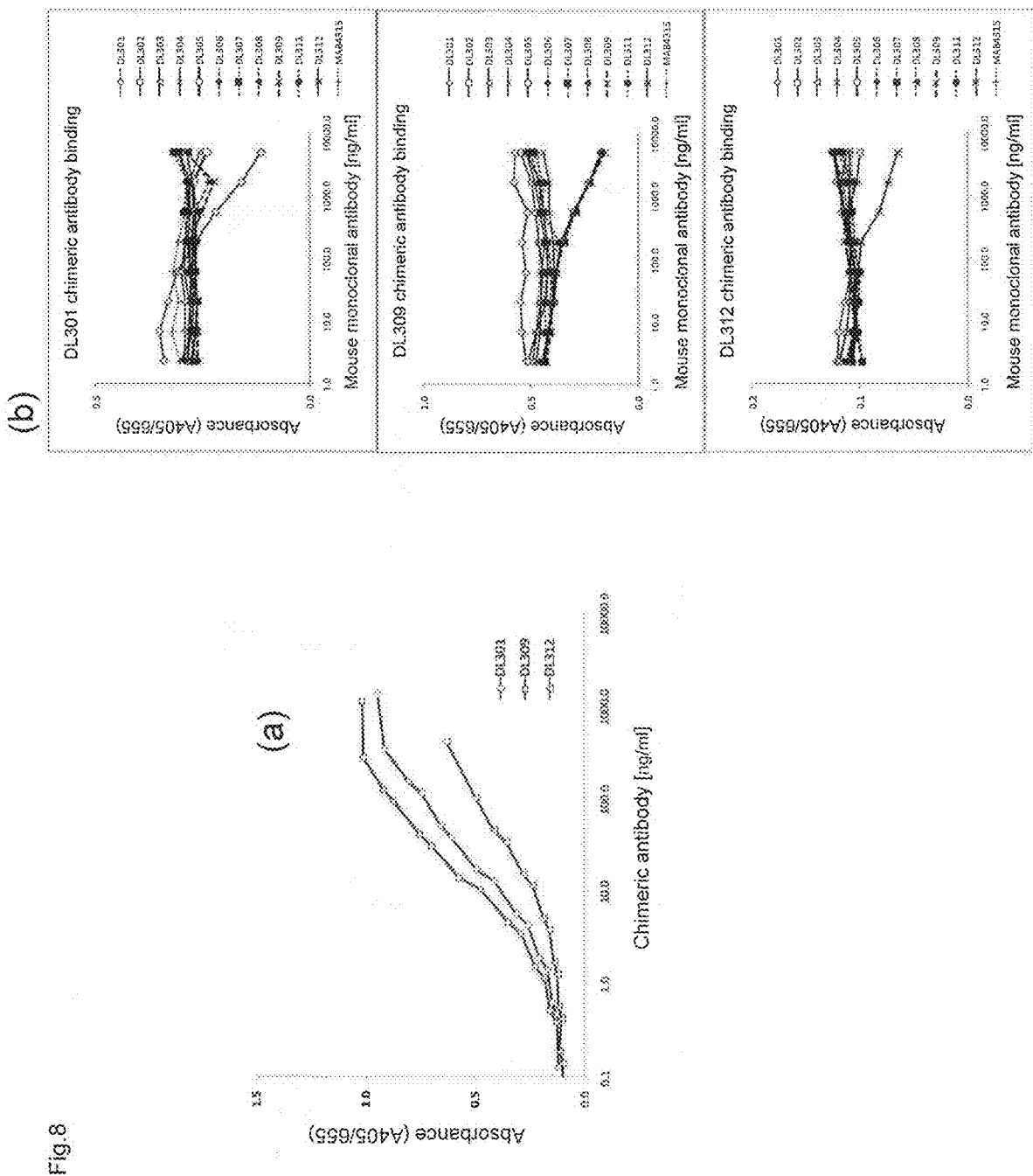
FIG. 8 shows the binding of a recombinant anti-DLL3 human chimeric antibody to a soluble DLL3 protein and the binding competition of an anti-DLL3 chimeric antibody with a mouse antibody against a soluble DLL3 protein.

The competition of a chimeric antibody and a mouse antibody for binding to the antigen molecule was analyzed by ELISA (FIG. 8(b)). Human DLL3-Fc was added at 10 ng/well to a Nunc immunoplate and immobilized thereon. A mixture (final concentration: 50 ng/ml) of the chimeric antibody and the appropriately diluted mouse antibody was added to the DLL3-Fc protein-immobilized plate. The plate was incubated at room temperature for 1 hour and then washed. Alkaline phosphatase-labeled anti-human antibodies were added thereto and incubated. After the incubation, Sigma 104 was added thereto, and the absorbance was measured. The binding of the chimeric antibody to the antigen molecule competed with that of the original mouse monoclonal antibody thereto. The antibodies other than the DL301 mouse antibody did not inhibit the binding of the DL301 chimeric antibody to the antigen. The antibodies other than the DL312 mouse antibody did not inhibit the binding of the DL312 chimeric antibody to the antigen. These results demonstrated that DL301 and DL312 bound to their respective unique epitopes. The DL305, DL308, and DL309 mouse antibodies inhibited the binding of the DL309 chimeric antibody to the antigen at almost the same level, suggesting that an epitope was the same among these 3 antibodies. The DL306 mouse antibody confirmed to have an ADCC-inducing activity did not inhibit the binding of the DL301, DL309, or DL312 chimeric antibody to the antigen. These results demonstrated that DL306 recognized an epitope independent of that for DL301, DL309, or DL312.

Figure 10:
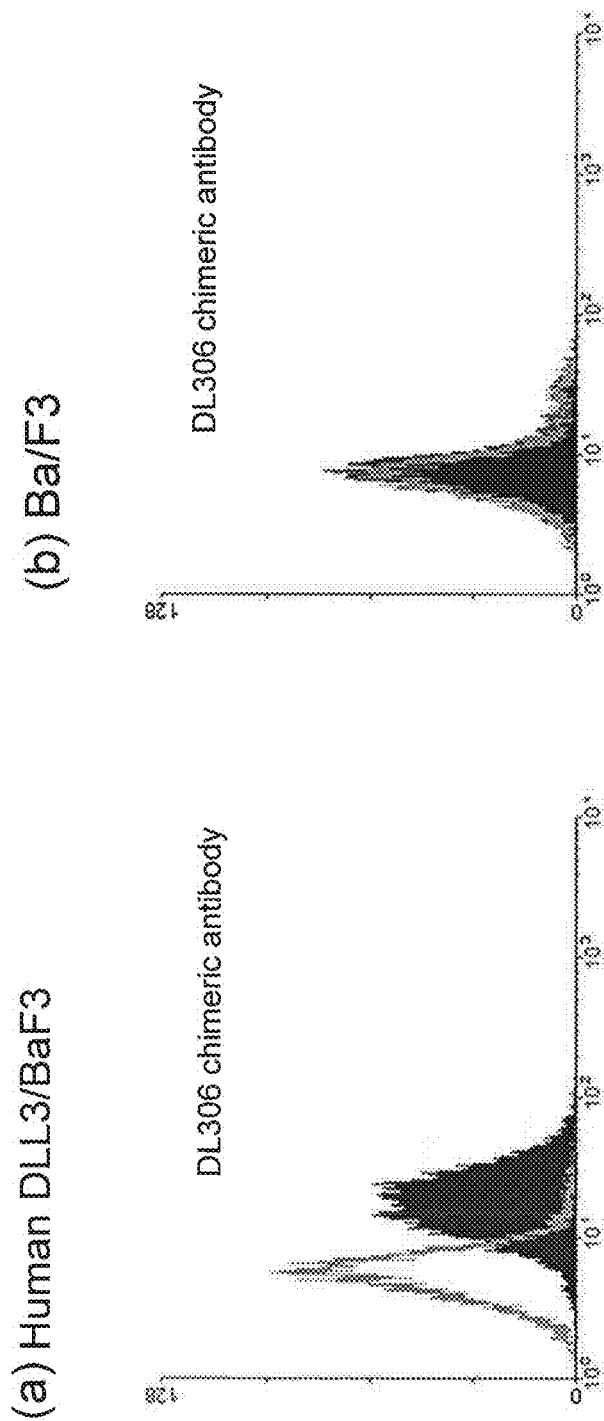
FIG. 10 shows the binding of a recombinant anti-DLL3 human chimeric antibody DL306 to the DLL3 protein on cell surface.

[Example 7] Establishment of Cell Line Expressing Recombinant Anti-DLL3 Antibody and Purification of Recombinant Antibody COS-7 cells were transfected with the DL306 chimeric antibody expression vector and allowed to transiently express the chimeric antibody. The chimeric antibody in the culture supernatant of COS-7 was confirmed to bind to the human DLL3 protein by flow cytometry. The chimeric antibody concentration in the culture supernatant of COS-7 was calculated by sandwich ELISA. In this concentration calculation, a human chimeric antibody known for its concentration was used as a standard. The chimeric antibody (final concentration: 1 µg/ml) was added to human DLL3/BaF3 cells suspended in a FACS buffer (PBS containing 1% fetal bovine serum). After incubation at 4° C. for 30 minutes and washing, the cells were reacted with FITC-labeled anti-human antibodies (Beckman Coulter, Inc.), and the binding of the chimeric antibody was analyzed using a flow cytometer FACSCalibur. As shown in FIG. 10, the chimeric antibody DL306 bound to human DLL3/BaF3 and did not bind to Ba/F3 cells, which were a parental line.

A cell line DG44 was transformed with the DL301, DL306, DL309, or DL312 human chimeric antibody expression vector. Drug-resistant cells were selected in the presence of Geneticin. Clones highly expressing the human chimeric antibody were selected by ELISA using anti-human antibodies to establish human chimeric antibody-producing DG44 cells.

Each protein of interest was purified from the culture supernatant of the human chimeric antibody-producing cell line by rProtein A affinity column chromatography and gel filtration chromatography. The concentration of the purified protein was determined by DC protein assay (Bio-Rad Laboratories, Inc.) with the IgG known for its concentration as a standard.

Mouse IgG2a antibody expression vector containing the VH- and VL-encoding sequences of DL301, DL306, or DL312 and mouse IgG2a constant region-encoding sequences were constructed. The light chain- and heavy chain-encoding sequences were both incorporated in one expression vector for mammalian cells and transcribed under the control of a mouse CMV promoter. A CHO cell line deficient in fucose transporter (WO2005/017155) was transformed with the mouse IgG2a antibody expression vector. Drug-resistant cells were selected in the presence of Geneticin. Clones highly expressing the mouse IgG2a antibody were selected by ELISA using anti-mouse IgG2a antibodies to establish mouse low-fucose IgG2a antibody-producing CHO cells. Each protein of interest was purified from the culture supernatant of the mouse low-fucose IgG2a antibody-producing cell line by Protein G affinity column chromatography and gel filtration chromatography. The concentration of the purified protein was determined by DC protein assay with the IgG known for its concentration as a standard.

TABLE 2

| | | |
|---|---|---|
| DL301 | Heavy chain | (SEQ ID NO: 69) |
| | Light chain | (SEQ ID NO: 16) |
| DL306 | Heavy chain | (SEQ ID NO: 70) |
| | Light chain | (SEQ ID NO: 28) |
| DL312 | Heavy chain | (SEQ ID NO: 71) |
| | Light chain | (SEQ ID NO: 52) |

[Example 8] Induction of ADCC Activity by Recombinant Anti-DLL3 Antibody

Human chimeric and mouse IgG2a recombinant anti-DLL3 antibodies were examined for their antibody-dependent cell-mediated cytotoxicity (ADCC)-inducing activities against DLL3-expressing cells labeled with calcein. DLL3-expressing human DLL3/BaF3 and small-cell lung cancer NCI-H1184 (ATCC) cell lines were separately cultured for 90 minutes in the presence of 20 µg/ml Calcein-AM (Dojindo, 349-07201), then centrifuged, and washed to prepare calcein-labeled target cells. The target cells were seeded at $1\times10^4$ cells/well to a 96-well plate (Coster 3799). Subsequently, the antibody adjusted to an appropriate final concentration was added thereto and incubated at room temperature for 15 minutes. Effector cells were added thereto at $5\times10^4$ cells/well. The reaction plate was incubated at 37° C. in a CO2 incubator. The effector cells used for the recombinant mouse low-fucose IgG2a antibody were NK92 cells expressing a mouse FcγR4-human FcγR3 chimeric molecule (WO 2008/093688). The effector cells used for the human chimeric recombinant antibody were NK92 cells expressing a human FcγR3 molecule. After 4-hour incubation, the plate was centrifuged, and 100 µl of the culture supernatant was collected from each well. The fluorescence intensity was measured using ARVO SX. The ADCC-inducing activity was calculated by the method described in Example 4.

Figure 11:
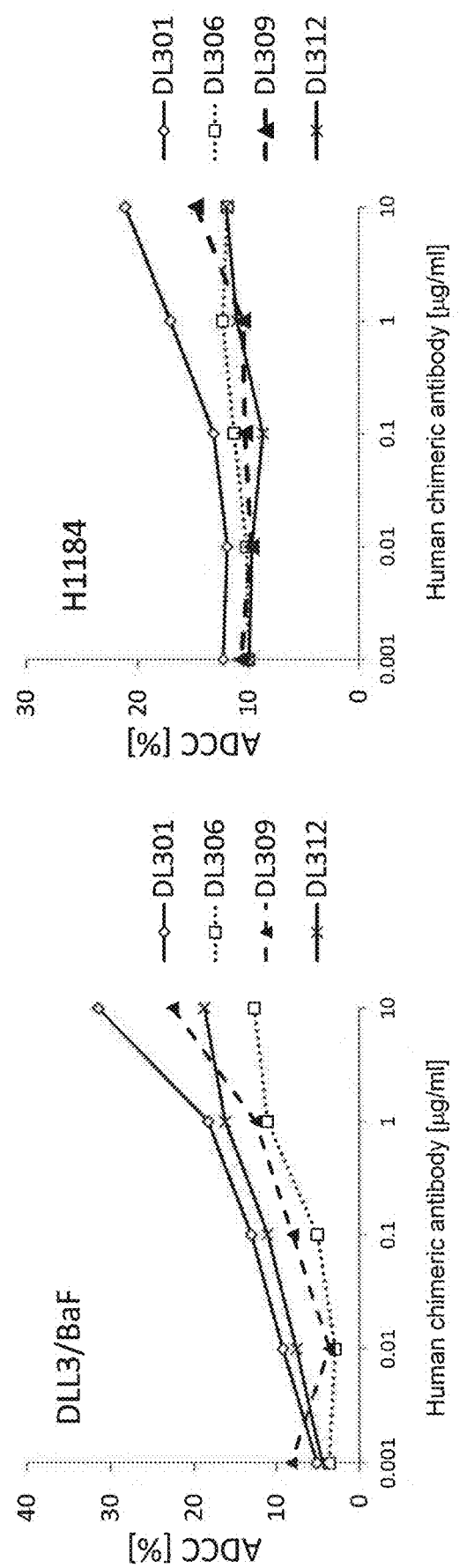
FIG. 11 shows the antibody concentration dependence of the ADCC activity of an anti-DLL3 human chimeric antibody against target cells DLL3/BaF3 and NCI-H1184.

FIG. 11 shows that the recombinant human chimeric antibodies DL301, DL306, DL309, and D312 induce ADCC against DLL3/BaF3 and NCI-H1184 in a dose-dependent manner.

Figure 12:
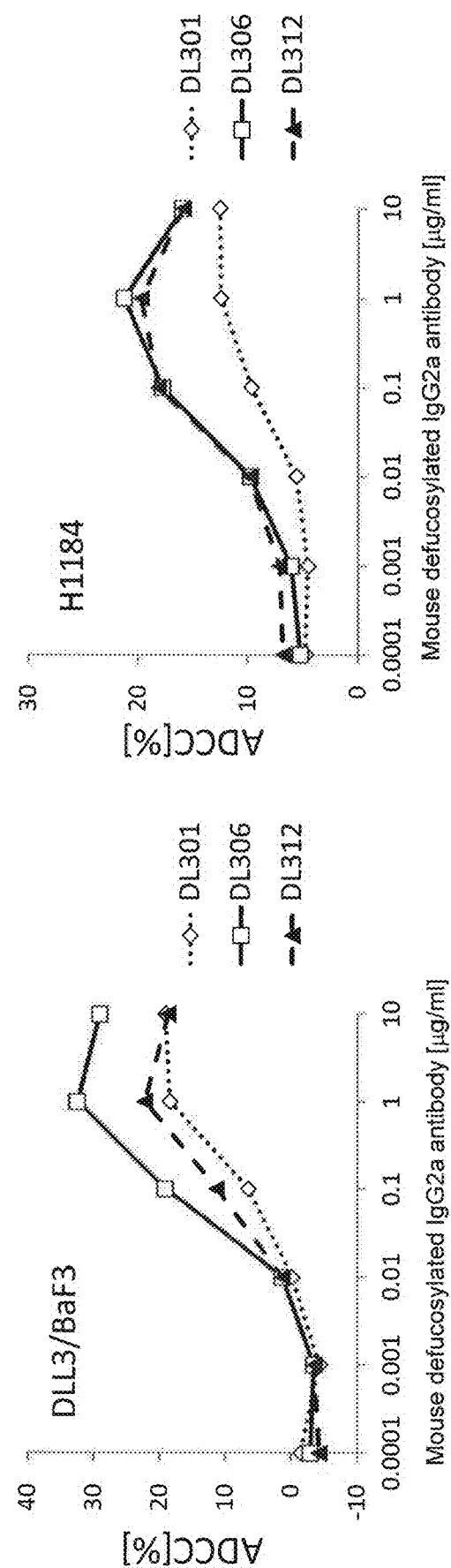
FIG. 12 shows the antibody concentration dependence of the ADCC activity of an anti-DLL3 mouse low-fucose antibody against target cells DLL3/BaF3 and NCI-H1184.

FIG. 12 shows that the recombinant mouse low-fucose IgG2a antibodies DL301, DL306, and D312 induce ADCC against DLL3/BaF3 and NCI-H1184 in a dose-dependent manner.

All publications, patents, and patent applications cited herein are incorporated herein by reference in their entirety.

The invention claimed is:

1. An antibody that binds to DLL3 having the amino acid sequence of SEQ ID NO: 1, wherein said antibody binds to a region between amino acids 216 to 492 of SEQ ID NO: 1, wherein the antibody has an internalizing activity and is either conjugated to, or is capable of being conjugated to, one or more cytotoxic substances, and wherein the anti-DLL3 antibody is an antibody comprising a heavy chain variable region comprising heavy chain CDR1 having the amino acid sequence as set forth in SEQ ID NO: 36, heavy chain CDR2 having the amino acid sequence as set forth in SEQ ID NO: 37, and heavy chain CDR3 having the amino acid sequence as set forth in SEQ ID NO: 38, and a light chain variable region comprising light chain CDR1 having the amino acid sequence as set forth in SEQ ID NO: 42, light chain CDR2 having the amino acid sequence as set forth in SEQ ID NO: 43, and light chain CDR3 having the amino acid sequence as set forth in SEQ ID NO: 44.

2. The antibody according to claim 1, wherein the antibody is a chimeric or humanized antibody.

3. The antibody according to claim 1, wherein the antibody is conjugated to one or more cytotoxic substances.

4. A method of inducing death of a cell expressing DLL3 having the amino acid sequence set forth in SEQ ID NO: 1, comprising contacting the cell with the antibody of claim 3.

5. The method according to claim 4, wherein the antibody is a chimeric or humanized antibody.

6. A method of suppressing growth of a cell expressing DLL3 as set forth in SEQ ID NO: 1, comprising contacting the cell with the antibody of claim 3.

7. The method according to claim 6, wherein the antibody is a chimeric or humanized antibody.

8. A method of treating cancer, comprising administering the antibody of claim 3 to a subject in need of such treatment.

9. The method according to claim 8, wherein the antibody is a chimeric or humanized antibody.

10. The method according to claim 8, wherein the cancer is a lung cancer.

11. The method according to claim 10, wherein the lung cancer is a small-cell lung cancer.

12. A method of identifying or selecting an anti-DLL3 antibody having internalizing activity that can bind to a region between amino acids 216 to 492 of SEQ ID NO: 1, wherein said method comprises identifying or selecting, from a plurality of antibodies, an antibody which binds to the same epitope in the DLL3 protein to which the antibody of claim 1 binds, or which competes with the antibody of claim 1 for binding to the DLL3 protein.

13. A method of identifying or selecting an anti-DLL3 antibody having internalizing activity that can bind to a region between amino acids 216 to 492 of SEQ ID NO: 1, wherein said method comprises identifying or selecting, from a plurality of antibodies, an antibody which binds to the same epitope in the DLL3 protein to which the antibody of claim 1 binds.

14. A method of identifying or selecting an anti-DLL3 antibody having internalizing activity that can bind to a region between amino acids 216 to 492 of SEQ ID NO: 1, wherein said method comprises identifying or selecting, from a plurality of antibodies, an antibody which competes with the antibody of claim 1 for binding to the DLL3 protein.

15. A method of identifying or selecting an anti-DLL3 antibody having internalizing activity that can bind to a region between amino acids 216 to 492 of SEQ ID NO: 1, wherein said method comprises identifying or selecting, from a plurality of antibodies, an antibody which binds to a region between amino acids 216 to 492 of SEQ ID NO: 1.

16. The method according to claim 15, wherein the antibody that is identified or selected binds to the same epitope in the DLL3 protein as an antibody comprising a heavy chain variable region comprising heavy chain CDR1 having the amino acid sequence as set forth in SEQ ID NO: 36, heavy chain CDR2 having the amino acid sequence as set forth in SEQ ID NO: 37, and heavy chain CDR3 having the amino acid sequence as set forth in SEQ ID NO: 38, and a light chain variable region comprising light chain CDR1 having the amino acid sequence as set forth in SEQ ID NO: 42, light chain CDR2 having the amino acid sequence as set forth in SEQ ID NO: 43, and light chain CDR3 having the amino acid sequence as set forth in SEQ ID NO: 44.

17. The method according to claim 15, wherein the antibody that is identified or selected competes for binding to the DLL3 protein with an antibody comprising a heavy chain variable region comprising heavy chain CDR1 having the amino acid sequence as set forth in SEQ ID NO: 36, heavy chain CDR2 having the amino acid sequence as set forth in SEQ ID NO: 37, and heavy chain CDR3 having the amino acid sequence as set forth in SEQ ID NO: 38, and a light chain variable region comprising light chain CDR1 having the amino acid sequence as set forth in SEQ ID NO: 42, light chain CDR2 having the amino acid sequence as set forth in SEQ ID NO: 43, and light chain CDR3 having the amino acid sequence as set forth in SEQ ID NO: 44.

* * * * *

SEQUENCE LISTING

<160> NUMBER OF SEQ ID NOS: 71

<210> SEQ ID NO 1
<211> LENGTH: 618

<212> TYPE: PRT
<213> ORGANISM: homo sapiens

<400> SEQUENCE: 1

```
Met Val Ser Pro Arg Met Ser Gly Leu Leu Ser Gln Thr Val Ile Leu
1               5                   10                  15

Ala Leu Ile Phe Leu Pro Gln Thr Arg Pro Ala Gly Val Phe Glu Leu
            20                  25                  30

Gln Ile His Ser Phe Gly Pro Gly Pro Gly Ala Pro Arg Ser
            35                  40                  45

Pro Cys Ser Ala Arg Leu Pro Cys Arg Leu Phe Phe Arg Val Cys Leu
        50                  55                  60

Lys Pro Gly Leu Ser Glu Glu Ala Ala Glu Ser Pro Cys Ala Leu Gly
65                  70                  75                  80

Ala Ala Leu Ser Ala Arg Gly Pro Val Tyr Thr Glu Gln Pro Gly Ala
                85                  90                  95

Pro Ala Pro Asp Leu Pro Leu Pro Asp Gly Leu Leu Gln Val Pro Phe
            100                 105                 110

Arg Asp Ala Trp Pro Gly Thr Phe Ser Phe Ile Ile Glu Thr Trp Arg
        115                 120                 125

Glu Glu Leu Gly Asp Gln Ile Gly Gly Pro Ala Trp Ser Leu Leu Ala
130                 135                 140

Arg Val Ala Gly Arg Arg Leu Ala Ala Gly Gly Pro Trp Ala Arg
145                 150                 155                 160

Asp Ile Gln Arg Ala Gly Ala Trp Glu Leu Arg Phe Ser Tyr Arg Ala
                165                 170                 175

Arg Cys Glu Pro Pro Ala Val Gly Thr Ala Cys Thr Arg Leu Cys Arg
            180                 185                 190

Pro Arg Ser Ala Pro Ser Arg Cys Gly Pro Gly Leu Arg Pro Cys Ala
        195                 200                 205

Pro Leu Glu Asp Glu Cys Glu Ala Pro Leu Val Cys Arg Ala Gly Cys
    210                 215                 220

Ser Pro Glu His Gly Phe Cys Glu Gln Pro Gly Glu Cys Arg Cys Leu
225                 230                 235                 240

Glu Gly Trp Thr Gly Pro Leu Cys Thr Val Pro Val Ser Thr Ser Ser
                245                 250                 255

Cys Leu Ser Pro Arg Gly Pro Ser Ser Ala Thr Thr Gly Cys Leu Val
            260                 265                 270

Pro Gly Pro Gly Pro Cys Asp Gly Asn Pro Cys Ala Asn Gly Gly Ser
        275                 280                 285

Cys Ser Glu Thr Pro Arg Ser Phe Glu Cys Thr Cys Pro Arg Gly Phe
    290                 295                 300

Tyr Gly Leu Arg Cys Glu Val Ser Gly Val Thr Cys Ala Asp Gly Pro
305                 310                 315                 320

Cys Phe Asn Gly Gly Leu Cys Val Gly Ala Asp Pro Asp Ser Ala
                325                 330                 335

Tyr Ile Cys His Cys Pro Pro Gly Phe Gln Gly Ser Asn Cys Glu Lys
            340                 345                 350

Arg Val Asp Arg Cys Ser Leu Gln Pro Cys Arg Asn Gly Gly Leu Cys
        355                 360                 365

Leu Asp Leu Gly His Ala Leu Arg Cys Arg Cys Arg Ala Gly Phe Ala
    370                 375                 380

Gly Pro Arg Cys Glu His Asp Leu Asp Asp Cys Ala Gly Arg Ala Cys
385                 390                 395                 400
```

```
Ala Asn Gly Gly Thr Cys Val Glu Gly Gly Ala His Arg Cys Ser
            405                 410                 415

Cys Ala Leu Gly Phe Gly Arg Asp Cys Arg Glu Arg Ala Asp Pro
        420                 425                 430

Cys Ala Ala Arg Pro Cys Ala His Gly Gly Arg Cys Tyr Ala His Phe
            435                 440                 445

Ser Gly Leu Val Cys Ala Cys Ala Pro Gly Tyr Met Gly Ala Arg Cys
    450                 455                 460

Glu Phe Pro Val His Pro Asp Gly Ala Ser Ala Leu Pro Ala Ala Pro
465                 470                 475                 480

Pro Gly Leu Arg Pro Gly Asp Pro Gln Arg Tyr Leu Pro Pro Ala
                485                 490                 495

Leu Gly Leu Leu Val Ala Ala Gly Val Ala Gly Ala Ala Leu Leu Leu
                500                 505                 510

Val His Val Arg Arg Gly His Ser Gln Asp Ala Gly Ser Arg Leu
                515                 520                 525

Leu Ala Gly Thr Pro Glu Pro Ser Val His Ala Leu Pro Asp Ala Leu
    530                 535                 540

Asn Asn Leu Arg Thr Gln Glu Gly Ser Gly Asp Gly Pro Ser Ser Ser
545                 550                 555                 560

Val Asp Trp Asn Arg Pro Glu Asp Val Asp Pro Gln Gly Ile Tyr Val
                565                 570                 575

Ile Ser Ala Pro Ser Ile Tyr Ala Arg Glu Val Ala Thr Pro Leu Phe
                580                 585                 590

Pro Pro Leu His Thr Gly Arg Ala Gly Gln Arg Gln His Leu Leu Phe
                595                 600                 605

Pro Tyr Pro Ser Ser Ile Leu Ser Val Lys
    610                 615

<210> SEQ ID NO 2
<211> LENGTH: 585
<212> TYPE: PRT
<213> ORGANISM: Mus musculus

<400> SEQUENCE: 2

Met Val Ser Leu Gln Val Ser Pro Leu Ser Gln Thr Leu Ile Leu Ala
1               5                   10                  15

Phe Leu Leu Pro Gln Ala Leu Pro Ala Gly Val Phe Glu Leu Gln Ile
                20                  25                  30

His Ser Phe Gly Pro Gly Pro Gly Leu Gly Thr Pro Arg Ser Pro Cys
            35                  40                  45

Asn Ala Arg Gly Pro Cys Arg Leu Phe Phe Arg Val Cys Leu Lys Pro
        50                  55                  60

Gly Val Ser Gln Glu Ala Thr Glu Ser Leu Cys Ala Leu Gly Ala Ala
65                  70                  75                  80

Leu Ser Thr Ser Val Pro Val Tyr Thr Glu His Pro Gly Glu Ser Ala
                85                  90                  95

Ala Ala Leu Pro Leu Pro Asp Gly Leu Val Arg Val Pro Phe Arg Asp
            100                 105                 110

Ala Trp Pro Gly Thr Phe Ser Leu Val Ile Glu Thr Trp Arg Glu Gln
        115                 120                 125

Leu Gly Glu His Ala Gly Gly Pro Ala Trp Asn Leu Leu Ala Arg Val
    130                 135                 140

Val Gly Arg Arg Arg Leu Ala Ala Gly Gly Pro Trp Ala Arg Asp Val
```

```
                145                 150                 155                 160
        Gln Arg Thr Gly Thr Trp Glu Leu His Phe Ser Tyr Arg Ala Arg Cys
                        165                 170                 175
        Glu Pro Pro Ala Val Gly Ala Ala Cys Ala Arg Leu Cys Arg Ser Arg
                        180                 185                 190
        Ser Ala Pro Ser Arg Cys Gly Pro Gly Leu Arg Pro Cys Thr Pro Phe
                        195                 200                 205
        Pro Asp Glu Cys Glu Ala Pro Ser Val Cys Arg Pro Gly Cys Ser Pro
            210                 215                 220
        Glu His Gly Tyr Cys Glu Glu Pro Asp Glu Cys Arg Cys Leu Glu Gly
        225                 230                 235                 240
        Trp Thr Gly Pro Leu Cys Thr Val Pro Val Ser Thr Ser Ser Cys Leu
                        245                 250                 255
        Asn Ser Arg Val Pro Gly Pro Ala Ser Thr Gly Cys Leu Leu Pro Gly
                        260                 265                 270
        Pro Gly Pro Cys Asp Gly Asn Pro Cys Ala Asn Gly Gly Ser Cys Ser
                        275                 280                 285
        Glu Thr Ser Gly Ser Phe Glu Cys Ala Cys Pro Arg Gly Phe Tyr Gly
            290                 295                 300
        Leu Arg Cys Glu Val Ser Gly Val Thr Cys Ala Asp Gly Pro Cys Phe
        305                 310                 315                 320
        Asn Gly Gly Leu Cys Val Gly Gly Glu Asp Pro Asp Ser Ala Tyr Val
                        325                 330                 335
        Cys His Cys Pro Pro Gly Phe Gln Gly Ser Asn Cys Glu Lys Arg Val
                        340                 345                 350
        Asp Arg Cys Ser Leu Gln Pro Cys Gln Asn Gly Gly Leu Cys Leu Asp
                        355                 360                 365
        Leu Gly His Ala Leu Arg Cys Arg Cys Arg Ala Gly Phe Ala Gly Pro
            370                 375                 380
        Arg Cys Glu His Asp Leu Asp Asp Cys Ala Gly Arg Ala Cys Ala Asn
        385                 390                 395                 400
        Gly Gly Thr Cys Val Glu Gly Gly Gly Ser Arg Arg Cys Ser Cys Ala
                        405                 410                 415
        Leu Gly Phe Gly Gly Arg Asp Cys Arg Glu Arg Ala Asp Pro Cys Ala
                        420                 425                 430
        Ser Arg Pro Cys Ala His Gly Gly Arg Cys Tyr Ala His Phe Ser Gly
                        435                 440                 445
        Leu Val Cys Ala Cys Ala Pro Gly Tyr Met Gly Val Arg Cys Glu Phe
            450                 455                 460
        Ala Val Arg Pro Asp Gly Ala Asp Ala Val Pro Ala Ala Pro Arg Gly
        465                 470                 475                 480
        Leu Arg Gln Ala Asp Pro Gln Arg Phe Leu Leu Pro Pro Ala Leu Gly
                        485                 490                 495
        Leu Leu Val Ala Ala Gly Leu Ala Gly Ala Ala Leu Leu Val Ile His
                        500                 505                 510
        Val Arg Arg Arg Gly Pro Gly Gln Asp Thr Gly Thr Arg Leu Leu Ser
                        515                 520                 525
        Gly Thr Arg Glu Pro Ser Val His Thr Leu Pro Asp Ala Leu Asn Asn
            530                 535                 540
        Leu Arg Leu Gln Asp Gly Ala Gly Asp Gly Pro Ser Ser Ser Ala Asp
        545                 550                 555                 560
        Trp Asn His Pro Glu Asp Gly Asp Ser Arg Ser Ile Tyr Val Ile Pro
                        565                 570                 575
```

```
Ala Pro Ser Ile Tyr Ala Arg Glu Ala
        580                 585

<210> SEQ ID NO 3
<211> LENGTH: 723
<212> TYPE: PRT
<213> ORGANISM: homo sapiens

<400> SEQUENCE: 3

Met Gly Ser Arg Cys Ala Leu Ala Leu Ala Val Leu Ser Ala Leu Leu
 1               5                  10                  15

Cys Gln Val Trp Ser Ser Gly Val Phe Glu Leu Lys Leu Gln Glu Phe
            20                  25                  30

Val Asn Lys Lys Gly Leu Leu Gly Asn Arg Asn Cys Cys Arg Gly Gly
        35                  40                  45

Ala Gly Pro Pro Pro Cys Ala Cys Arg Thr Phe Phe Arg Val Cys Leu
    50                  55                  60

Lys His Tyr Gln Ala Ser Val Ser Pro Glu Pro Pro Cys Thr Tyr Gly
65                  70                  75                  80

Ser Ala Val Thr Pro Val Leu Gly Val Asp Ser Phe Ser Leu Pro Asp
                85                  90                  95

Gly Gly Gly Ala Asp Ser Ala Phe Ser Asn Pro Ile Arg Phe Pro Phe
            100                 105                 110

Gly Phe Thr Trp Pro Gly Thr Phe Ser Leu Ile Ile Glu Ala Leu His
        115                 120                 125

Thr Asp Ser Pro Asp Asp Leu Ala Thr Glu Asn Pro Glu Arg Leu Ile
130                 135                 140

Ser Arg Leu Ala Thr Gln Arg His Leu Thr Val Gly Glu Glu Trp Ser
145                 150                 155                 160

Gln Asp Leu His Ser Ser Gly Arg Thr Asp Leu Lys Tyr Ser Tyr Arg
                165                 170                 175

Phe Val Cys Asp Glu His Tyr Tyr Gly Glu Gly Cys Ser Val Phe Cys
            180                 185                 190

Arg Pro Arg Asp Asp Ala Phe Gly His Phe Thr Cys Gly Glu Arg Gly
        195                 200                 205

Glu Lys Val Cys Asn Pro Gly Trp Lys Gly Pro Tyr Cys Thr Glu Pro
    210                 215                 220

Ile Cys Leu Pro Gly Cys Asp Glu Gln His Gly Phe Cys Asp Lys Pro
225                 230                 235                 240

Gly Glu Cys Lys Cys Arg Val Gly Trp Gln Gly Arg Tyr Cys Asp Glu
                245                 250                 255

Cys Ile Arg Tyr Pro Gly Cys Leu His Gly Thr Cys Gln Gln Pro Trp
            260                 265                 270

Gln Cys Asn Cys Gln Glu Gly Trp Gly Gly Leu Phe Cys Asn Gln Asp
        275                 280                 285

Leu Asn Tyr Cys Thr His His Lys Pro Cys Lys Asn Gly Ala Thr Cys
    290                 295                 300

Thr Asn Thr Gly Gln Gly Ser Tyr Thr Cys Ser Cys Arg Pro Gly Tyr
305                 310                 315                 320

Thr Gly Ala Thr Cys Glu Leu Gly Ile Asp Glu Cys Asp Pro Ser Pro
                325                 330                 335

Cys Lys Asn Gly Gly Ser Cys Thr Asp Leu Glu Asn Ser Tyr Ser Cys
            340                 345                 350

Thr Cys Pro Pro Gly Phe Tyr Gly Lys Ile Cys Glu Leu Ser Ala Met
```

```
                    355                 360                 365
Thr Cys Ala Asp Gly Pro Cys Phe Asn Gly Gly Arg Cys Ser Asp Ser
            370                 375                 380

Pro Asp Gly Gly Tyr Ser Cys Arg Cys Pro Val Gly Tyr Ser Gly Phe
385                 390                 395                 400

Asn Cys Glu Lys Lys Ile Asp Tyr Cys Ser Ser Pro Cys Ser Asn
                405                 410                 415

Gly Ala Lys Cys Val Asp Leu Gly Asp Ala Tyr Leu Cys Arg Cys Gln
            420                 425                 430

Ala Gly Phe Ser Gly Arg His Cys Asp Asp Asn Val Asp Asp Cys Ala
            435                 440                 445

Ser Ser Pro Cys Ala Asn Gly Gly Thr Cys Arg Asp Gly Val Asn Asp
    450                 455                 460

Phe Ser Cys Thr Cys Pro Pro Gly Tyr Thr Gly Arg Asn Cys Ser Ala
465                 470                 475                 480

Pro Val Ser Arg Cys Glu His Ala Pro Cys His Asn Gly Ala Thr Cys
                485                 490                 495

His Glu Arg Gly His Arg Tyr Val Cys Glu Cys Ala Arg Gly Tyr Gly
            500                 505                 510

Gly Pro Asn Cys Gln Phe Leu Leu Pro Glu Leu Pro Pro Gly Pro Ala
            515                 520                 525

Val Val Asp Leu Thr Glu Lys Leu Glu Gly Gln Gly Gly Pro Phe Pro
            530                 535                 540

Trp Val Ala Val Cys Ala Gly Val Ile Leu Val Leu Met Leu Leu Leu
545                 550                 555                 560

Gly Cys Ala Ala Val Val Val Cys Val Arg Leu Arg Leu Gln Lys His
                565                 570                 575

Arg Pro Pro Ala Asp Pro Cys Arg Gly Glu Thr Glu Thr Met Asn Asn
            580                 585                 590

Leu Ala Asn Cys Gln Arg Glu Lys Asp Ile Ser Val Ser Ile Ile Gly
            595                 600                 605

Ala Thr Gln Ile Lys Asn Thr Asn Lys Lys Ala Asp Phe His Gly Asp
            610                 615                 620

His Ser Ala Asp Lys Asn Gly Phe Lys Ala Arg Tyr Pro Ala Val Asp
625                 630                 635                 640

Tyr Asn Leu Val Gln Asp Leu Lys Gly Asp Asp Thr Ala Val Arg Asp
                645                 650                 655

Ala His Ser Lys Arg Asp Thr Lys Cys Gln Pro Gln Gly Ser Ser Gly
            660                 665                 670

Glu Glu Lys Gly Thr Pro Thr Thr Leu Arg Gly Gly Glu Ala Ser Glu
        675                 680                 685

Arg Lys Arg Pro Asp Ser Gly Cys Ser Thr Ser Lys Asp Thr Lys Tyr
            690                 695                 700

Gln Ser Val Tyr Val Ile Ser Glu Glu Lys Asp Glu Cys Val Ile Ala
705                 710                 715                 720

Thr Glu Val

<210> SEQ ID NO 4
<211> LENGTH: 2555
<212> TYPE: PRT
<213> ORGANISM: homo sapiens

<400> SEQUENCE: 4

Met Pro Pro Leu Leu Ala Pro Leu Leu Cys Leu Ala Leu Leu Pro Ala
```

-continued

```
1               5                   10                  15
Leu Ala Ala Arg Gly Pro Arg Cys Ser Gln Pro Gly Glu Thr Cys Leu
                20                  25                  30
Asn Gly Gly Lys Cys Glu Ala Ala Asn Gly Thr Glu Ala Cys Val Cys
                35                  40                  45
Gly Gly Ala Phe Val Gly Pro Arg Cys Gln Asp Pro Asn Pro Cys Leu
        50                  55                  60
Ser Thr Pro Cys Lys Asn Ala Gly Thr Cys His Val Val Asp Arg Arg
65                  70                  75                  80
Gly Val Ala Asp Tyr Ala Cys Ser Cys Ala Leu Gly Phe Ser Gly Pro
                85                  90                  95
Leu Cys Leu Thr Pro Leu Asp Asn Ala Cys Leu Thr Asn Pro Cys Arg
                100                 105                 110
Asn Gly Gly Thr Cys Asp Leu Leu Thr Leu Thr Glu Tyr Lys Cys Arg
                115                 120                 125
Cys Pro Pro Gly Trp Ser Gly Lys Ser Cys Gln Gln Ala Asp Pro Cys
        130                 135                 140
Ala Ser Asn Pro Cys Ala Asn Gly Gly Gln Cys Leu Pro Phe Glu Ala
145                 150                 155                 160
Ser Tyr Ile Cys His Cys Pro Pro Ser Phe His Gly Pro Thr Cys Arg
                165                 170                 175
Gln Asp Val Asn Glu Cys Gly Gln Lys Pro Gly Leu Cys Arg His Gly
                180                 185                 190
Gly Thr Cys His Asn Glu Val Gly Ser Tyr Arg Cys Val Cys Arg Ala
                195                 200                 205
Thr His Thr Gly Pro Asn Cys Glu Arg Pro Tyr Val Pro Cys Ser Pro
        210                 215                 220
Ser Pro Cys Gln Asn Gly Gly Thr Cys Arg Pro Thr Gly Asp Val Thr
225                 230                 235                 240
His Glu Cys Ala Cys Leu Pro Gly Phe Thr Gly Gln Asn Cys Glu Glu
                245                 250                 255
Asn Ile Asp Asp Cys Pro Gly Asn Asn Cys Lys Asn Gly Gly Ala Cys
                260                 265                 270
Val Asp Gly Val Asn Thr Tyr Asn Cys Arg Cys Pro Pro Glu Trp Thr
                275                 280                 285
Gly Gln Tyr Cys Thr Glu Asp Val Asp Glu Cys Gln Leu Met Pro Asn
        290                 295                 300
Ala Cys Gln Asn Gly Gly Thr Cys His Asn Thr His Gly Gly Tyr Asn
305                 310                 315                 320
Cys Val Cys Val Asn Gly Trp Thr Gly Glu Asp Cys Ser Glu Asn Ile
                325                 330                 335
Asp Asp Cys Ala Ser Ala Ala Cys Phe His Gly Ala Thr Cys His Asp
                340                 345                 350
Arg Val Ala Ser Phe Tyr Cys Glu Cys Pro His Gly Arg Thr Gly Leu
                355                 360                 365
Leu Cys His Leu Asn Asp Ala Cys Ile Ser Asn Pro Cys Asn Glu Gly
        370                 375                 380
Ser Asn Cys Asp Thr Asn Pro Val Asn Gly Lys Ala Ile Cys Thr Cys
385                 390                 395                 400
Pro Ser Gly Tyr Thr Gly Pro Ala Cys Ser Gln Asp Val Asp Glu Cys
                405                 410                 415
Ser Leu Gly Ala Asn Pro Cys Glu His Ala Gly Lys Cys Ile Asn Thr
                420                 425                 430
```

```
Leu Gly Ser Phe Glu Cys Gln Cys Leu Gln Gly Tyr Thr Gly Pro Arg
        435                 440                 445

Cys Glu Ile Asp Val Asn Glu Cys Val Ser Asn Pro Cys Gln Asn Asp
        450                 455                 460

Ala Thr Cys Leu Asp Gln Ile Gly Glu Phe Gln Cys Ile Cys Met Pro
465                 470                 475                 480

Gly Tyr Glu Gly Val His Cys Glu Val Asn Thr Asp Glu Cys Ala Ser
                485                 490                 495

Ser Pro Cys Leu His Asn Gly Arg Cys Leu Asp Lys Ile Asn Glu Phe
            500                 505                 510

Gln Cys Glu Cys Pro Thr Gly Phe Thr Gly His Leu Cys Gln Tyr Asp
        515                 520                 525

Val Asp Glu Cys Ala Ser Thr Pro Cys Lys Asn Gly Ala Lys Cys Leu
        530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Arg
            580                 585                 590

Pro Gly Tyr Thr Gly His His Cys Glu Thr Asn Ile Asn Glu Cys Ser
        595                 600                 605

Ser Gln Pro Cys Arg His Gly Gly Thr Cys Gln Asp Arg Asp Asn Ala
        610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
                645                 650                 655

Asp Lys Ile Asp Gly Tyr Glu Cys Ala Cys Glu Pro Gly Tyr Thr Gly
            660                 665                 670

Ser Met Cys Asn Ile Asn Ile Asp Glu Cys Ala Gly Asn Pro Cys His
        675                 680                 685

Asn Gly Gly Thr Cys Glu Asp Gly Ile Asn Gly Phe Thr Cys Arg Cys
        690                 695                 700

Pro Glu Gly Tyr His Asp Pro Thr Cys Leu Ser Glu Val Asn Glu Cys
705                 710                 715                 720

Asn Ser Asn Pro Cys Val His Gly Ala Cys Arg Asp Ser Leu Asn Gly
                725                 730                 735

Tyr Lys Cys Asp Cys Asp Pro Gly Trp Ser Gly Thr Asn Cys Asp Ile
            740                 745                 750

Asn Asn Asn Glu Cys Glu Ser Asn Pro Cys Val Asn Gly Gly Thr Cys
        755                 760                 765

Lys Asp Met Thr Ser Gly Tyr Val Cys Thr Cys Arg Glu Gly Phe Ser
        770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Leu Leu Pro Tyr Thr Gly Ala Thr Cys Glu Val Val Leu Ala Pro
            820                 825                 830

Cys Ala Pro Ser Pro Cys Arg Asn Gly Gly Glu Cys Arg Gln Ser Glu
        835                 840                 845
```

```
Asp Tyr Glu Ser Phe Ser Cys Val Cys Pro Thr Gly Trp Gln Gly Gln
850                 855                 860

Thr Cys Glu Val Asp Ile Asn Glu Cys Val Leu Ser Pro Cys Arg His
865                 870                 875                 880

Gly Ala Ser Cys Gln Asn Thr His Gly Gly Tyr Arg Cys His Cys Gln
                885                 890                 895

Ala Gly Tyr Ser Gly Arg Asn Cys Glu Thr Asp Ile Asp Asp Cys Arg
                900                 905                 910

Pro Asn Pro Cys His Asn Gly Gly Ser Cys Thr Asp Gly Ile Asn Thr
            915                 920                 925

Ala Phe Cys Asp Cys Leu Pro Gly Phe Arg Gly Thr Phe Cys Glu Glu
        930                 935                 940

Asp Ile Asn Glu Cys Ala Ser Asp Pro Cys Arg Asn Gly Ala Asn Cys
945                 950                 955                 960

Thr Asp Cys Val Asp Ser Tyr Thr Cys Thr Cys Pro Ala Gly Phe Ser
            965                 970                 975

Gly Ile His Cys Glu Asn Asn Thr Pro Asp Cys Thr Glu Ser Ser Cys
            980                 985                 990

Phe Asn Gly Gly Thr Cys Val Asp Gly Ile Asn Ser Phe Thr Cys Leu
        995                 1000                1005

Cys Pro Pro Gly Phe Thr Gly Ser Tyr Cys Gln His Asp Val Asn
    1010                1015                1020

Glu Cys Asp Ser Gln Pro Cys Leu His Gly Gly Thr Cys Gln Asp
    1025                1030                1035

Gly Cys Gly Ser Tyr Arg Cys Thr Cys Pro Gln Gly Tyr Thr Gly
    1040                1045                1050

Pro Asn Cys Gln Asn Leu Val His Trp Cys Asp Ser Ser Pro Cys
    1055                1060                1065

Lys Asn Gly Gly Lys Cys Trp Gln Thr His Thr Gln Tyr Arg Cys
    1070                1075                1080

Glu Cys Pro Ser Gly Trp Thr Gly Leu Tyr Cys Asp Val Pro Ser
    1085                1090                1095

Val Ser Cys Glu Val Ala Ala Gln Arg Gln Gly Val Asp Val Ala
    1100                1105                1110

Arg Leu Cys Gln His Gly Gly Leu Cys Val Asp Ala Gly Asn Thr
    1115                1120                1125

His His Cys Arg Cys Gln Ala Gly Tyr Thr Gly Ser Tyr Cys Glu
    1130                1135                1140

Asp Leu Val Asp Glu Cys Ser Pro Ser Pro Cys Gln Asn Gly Ala
    1145                1150                1155

Thr Cys Thr Asp Tyr Leu Gly Gly Tyr Ser Cys Lys Cys Val Ala
    1160                1165                1170

Gly Tyr His Gly Val Asn Cys Ser Glu Glu Ile Asp Glu Cys Leu
    1175                1180                1185

Ser His Pro Cys Gln Asn Gly Gly Thr Cys Leu Asp Leu Pro Asn
    1190                1195                1200

Thr Tyr Lys Cys Ser Cys Pro Arg Gly Thr Gln Gly Val His Cys
    1205                1210                1215

Glu Ile Asn Val Asp Asp Cys Asn Pro Pro Val Asp Pro Val Ser
    1220                1225                1230

Arg Ser Pro Lys Cys Phe Asn Asn Gly Thr Cys Val Asp Gln Val
    1235                1240                1245

Gly Gly Tyr Ser Cys Thr Cys Pro Pro Gly Phe Val Gly Glu Arg
```

|     |     |     |     |     |     |     |     |     |     |
|-----|-----|-----|-----|-----|-----|-----|-----|-----|-----|
|     | 1250 |     |     | 1255 |     |     | 1260 |     |     |
| Cys | Glu | Gly | Asp | Val | Asn | Glu | Cys | Leu | Ser | Asn | Pro | Cys | Asp | Ala |
|     | 1265 |     |     | 1270 |     |     | 1275 |     |     |
| Arg | Gly | Thr | Gln | Asn | Cys | Val | Gln | Arg | Val | Asn | Asp | Phe | His | Cys |
|     | 1280 |     |     | 1285 |     |     | 1290 |     |     |
| Glu | Cys | Arg | Ala | Gly | His | Thr | Gly | Arg | Arg | Cys | Glu | Ser | Val | Ile |
|     | 1295 |     |     | 1300 |     |     | 1305 |     |     |
| Asn | Gly | Cys | Lys | Gly | Lys | Pro | Cys | Lys | Asn | Gly | Gly | Thr | Cys | Ala |
|     | 1310 |     |     | 1315 |     |     | 1320 |     |     |
| Val | Ala | Ser | Asn | Thr | Ala | Arg | Gly | Phe | Ile | Cys | Lys | Cys | Pro | Ala |
|     | 1325 |     |     | 1330 |     |     | 1335 |     |     |
| Gly | Phe | Glu | Gly | Ala | Thr | Cys | Glu | Asn | Asp | Ala | Arg | Thr | Cys | Gly |
|     | 1340 |     |     | 1345 |     |     | 1350 |     |     |
| Ser | Leu | Arg | Cys | Leu | Asn | Gly | Gly | Thr | Cys | Ile | Ser | Gly | Pro | Arg |
|     | 1355 |     |     | 1360 |     |     | 1365 |     |     |
| Ser | Pro | Thr | Cys | Leu | Cys | Leu | Gly | Pro | Phe | Thr | Gly | Pro | Glu | Cys |
|     | 1370 |     |     | 1375 |     |     | 1380 |     |     |
| Gln | Phe | Pro | Ala | Ser | Ser | Pro | Cys | Leu | Gly | Gly | Asn | Pro | Cys | Tyr |
|     | 1385 |     |     | 1390 |     |     | 1395 |     |     |
| Asn | Gln | Gly | Thr | Cys | Glu | Pro | Thr | Ser | Glu | Ser | Pro | Phe | Tyr | Arg |
|     | 1400 |     |     | 1405 |     |     | 1410 |     |     |
| Cys | Leu | Cys | Pro | Ala | Lys | Phe | Asn | Gly | Leu | Leu | Cys | His | Ile | Leu |
|     | 1415 |     |     | 1420 |     |     | 1425 |     |     |
| Asp | Tyr | Ser | Phe | Gly | Gly | Gly | Ala | Gly | Arg | Asp | Ile | Pro | Pro | Pro |
|     | 1430 |     |     | 1435 |     |     | 1440 |     |     |
| Leu | Ile | Glu | Glu | Ala | Cys | Glu | Leu | Pro | Glu | Cys | Gln | Glu | Asp | Ala |
|     | 1445 |     |     | 1450 |     |     | 1455 |     |     |
| Gly | Asn | Lys | Val | Cys | Ser | Leu | Gln | Cys | Asn | Asn | His | Ala | Cys | Gly |
|     | 1460 |     |     | 1465 |     |     | 1470 |     |     |
| Trp | Asp | Gly | Gly | Asp | Cys | Ser | Leu | Asn | Phe | Asn | Asp | Pro | Trp | Lys |
|     | 1475 |     |     | 1480 |     |     | 1485 |     |     |
| Asn | Cys | Thr | Gln | Ser | Leu | Gln | Cys | Trp | Lys | Tyr | Phe | Ser | Asp | Gly |
|     | 1490 |     |     | 1495 |     |     | 1500 |     |     |
| His | Cys | Asp | Ser | Gln | Cys | Asn | Ser | Ala | Gly | Cys | Leu | Phe | Asp | Gly |
|     | 1505 |     |     | 1510 |     |     | 1515 |     |     |
| Phe | Asp | Cys | Gln | Arg | Ala | Glu | Gly | Gln | Cys | Asn | Pro | Leu | Tyr | Asp |
|     | 1520 |     |     | 1525 |     |     | 1530 |     |     |
| Gln | Tyr | Cys | Lys | Asp | His | Phe | Ser | Asp | Gly | His | Cys | Asp | Gln | Gly |
|     | 1535 |     |     | 1540 |     |     | 1545 |     |     |
| Cys | Asn | Ser | Ala | Glu | Cys | Glu | Trp | Asp | Gly | Leu | Asp | Cys | Ala | Glu |
|     | 1550 |     |     | 1555 |     |     | 1560 |     |     |
| His | Val | Pro | Glu | Arg | Leu | Ala | Ala | Gly | Thr | Leu | Val | Val | Val | Val |
|     | 1565 |     |     | 1570 |     |     | 1575 |     |     |
| Leu | Met | Pro | Pro | Glu | Gln | Leu | Arg | Asn | Ser | Ser | Phe | His | Phe | Leu |
|     | 1580 |     |     | 1585 |     |     | 1590 |     |     |
| Arg | Glu | Leu | Ser | Arg | Val | Leu | His | Thr | Asn | Val | Val | Phe | Lys | Arg |
|     | 1595 |     |     | 1600 |     |     | 1605 |     |     |
| Asp | Ala | His | Gly | Gln | Gln | Met | Ile | Phe | Pro | Tyr | Tyr | Gly | Arg | Glu |
|     | 1610 |     |     | 1615 |     |     | 1620 |     |     |
| Glu | Glu | Leu | Arg | Lys | His | Pro | Ile | Lys | Arg | Ala | Ala | Glu | Gly | Trp |
|     | 1625 |     |     | 1630 |     |     | 1635 |     |     |
| Ala | Ala | Pro | Asp | Ala | Leu | Leu | Gly | Gln | Val | Lys | Ala | Ser | Leu | Leu |
|     | 1640 |     |     | 1645 |     |     | 1650 |     |     |

```
Pro Gly Gly Ser Glu Gly Gly Arg Arg Arg Glu Leu Asp Pro
    1655            1660            1665

Met Asp Val Arg Gly Ser Ile Val Tyr Leu Glu Ile Asp Asn Arg
    1670            1675            1680

Gln Cys Val Gln Ala Ser Ser Gln Cys Phe Gln Ser Ala Thr Asp
    1685            1690            1695

Val Ala Ala Phe Leu Gly Ala Leu Ala Ser Leu Gly Ser Leu Asn
    1700            1705            1710

Ile Pro Tyr Lys Ile Glu Ala Val Gln Ser Glu Thr Val Glu Pro
    1715            1720            1725

Pro Pro Pro Ala Gln Leu His Phe Met Tyr Val Ala Ala Ala Ala
    1730            1735            1740

Phe Val Leu Leu Phe Phe Val Gly Cys Gly Val Leu Leu Ser Arg
    1745            1750            1755

Lys Arg Arg Arg Gln His Gly Gln Leu Trp Phe Pro Glu Gly Phe
    1760            1765            1770

Lys Val Ser Glu Ala Ser Lys Lys Arg Arg Glu Pro Leu Gly
    1775            1780            1785

Glu Asp Ser Val Gly Leu Lys Pro Leu Lys Asn Ala Ser Asp Gly
    1790            1795            1800

Ala Leu Met Asp Asp Asn Gln Asn Glu Trp Gly Asp Glu Asp Leu
    1805            1810            1815

Glu Thr Lys Lys Phe Arg Phe Glu Glu Pro Val Val Leu Pro Asp
    1820            1825            1830

Leu Asp Asp Gln Thr Asp His Arg Gln Trp Thr Gln Gln His Leu
    1835            1840            1845

Asp Ala Ala Asp Leu Arg Met Ser Ala Met Ala Pro Thr Pro Pro
    1850            1855            1860

Gln Gly Glu Val Asp Ala Asp Cys Met Asp Val Asn Val Arg Gly
    1865            1870            1875

Pro Asp Gly Phe Thr Pro Leu Met Ile Ala Ser Cys Ser Gly Gly
    1880            1885            1890

Gly Leu Glu Thr Gly Asn Ser Glu Glu Glu Glu Asp Ala Pro Ala
    1895            1900            1905

Val Ile Ser Asp Phe Ile Tyr Gln Gly Ala Ser Leu His Asn Gln
    1910            1915            1920

Thr Asp Arg Thr Gly Glu Thr Ala Leu His Leu Ala Ala Arg Tyr
    1925            1930            1935

Ser Arg Ser Asp Ala Ala Lys Arg Leu Leu Glu Ala Ser Ala Asp
    1940            1945            1950

Ala Asn Ile Gln Asp Asn Met Gly Arg Thr Pro Leu His Ala Ala
    1955            1960            1965

Val Ser Ala Asp Ala Gln Gly Val Phe Gln Ile Leu Ile Arg Asn
    1970            1975            1980

Arg Ala Thr Asp Leu Asp Ala Arg Met His Asp Gly Thr Thr Pro
    1985            1990            1995

Leu Ile Leu Ala Ala Arg Leu Ala Val Glu Gly Met Leu Glu Asp
    2000            2005            2010

Leu Ile Asn Ser His Ala Asp Val Asn Ala Val Asp Asp Leu Gly
    2015            2020            2025

Lys Ser Ala Leu His Trp Ala Ala Val Asn Asn Val Asp Ala
    2030            2035            2040
```

```
Ala Val  Val Leu Leu Lys Asn  Gly Ala Asn Lys Asp  Met Gln Asn
    2045             2050             2055

Asn Arg  Glu Glu Thr Pro Leu  Phe Leu Ala Ala Arg  Glu Gly Ser
    2060             2065             2070

Tyr Glu  Thr Ala Lys Val Leu  Leu Asp His Phe Ala  Asn Arg Asp
    2075             2080             2085

Ile Thr  Asp His Met Asp Arg  Leu Pro Arg Asp Ile  Ala Gln Glu
    2090             2095             2100

Arg Met  His His Asp Ile Val  Arg Leu Leu Asp Glu  Tyr Asn Leu
    2105             2110             2115

Val Arg  Ser Pro Gln Leu His  Gly Ala Pro Leu Gly  Gly Thr Pro
    2120             2125             2130

Thr Leu  Ser Pro Pro Leu Cys  Ser Pro Asn Gly Tyr  Leu Gly Ser
    2135             2140             2145

Leu Lys  Pro Gly Val Gln Gly  Lys Lys Val Arg Lys  Pro Ser Ser
    2150             2155             2160

Lys Gly  Leu Ala Cys Gly Ser  Lys Glu Ala Lys Asp  Leu Lys Ala
    2165             2170             2175

Arg Arg  Lys Lys Ser Gln Asp  Gly Lys Gly Cys Leu  Leu Asp Ser
    2180             2185             2190

Ser Gly  Met Leu Ser Pro Val  Asp Ser Leu Glu Ser  Pro His Gly
    2195             2200             2205

Tyr Leu  Ser Asp Val Ala Ser  Pro Pro Leu Leu Pro  Ser Pro Phe
    2210             2215             2220

Gln Gln  Ser Pro Ser Val Pro  Leu Asn His Leu Pro  Gly Met Pro
    2225             2230             2235

Asp Thr  His Leu Gly Ile Gly  His Leu Asn Val Ala  Ala Lys Pro
    2240             2245             2250

Glu Met  Ala Ala Leu Gly Gly  Gly Gly Arg Leu Ala  Phe Glu Thr
    2255             2260             2265

Gly Pro  Pro Arg Leu Ser His  Leu Pro Val Ala Ser  Gly Thr Ser
    2270             2275             2280

Thr Val  Leu Gly Ser Ser Ser  Gly Gly Ala Leu Asn  Phe Thr Val
    2285             2290             2295

Gly Gly  Ser Thr Ser Leu Asn  Gly Gln Cys Glu Trp  Leu Ser Arg
    2300             2305             2310

Leu Gln  Ser Gly Met Val Pro  Asn Gln Tyr Asn Pro  Leu Arg Gly
    2315             2320             2325

Ser Val  Ala Pro Gly Pro Leu  Ser Thr Gln Ala Pro  Ser Leu Gln
    2330             2335             2340

His Gly  Met Val Gly Pro Leu  His Ser Ser Leu Ala  Ala Ser Ala
    2345             2350             2355

Leu Ser  Gln Met Met Ser Tyr  Gln Gly Leu Pro Ser  Thr Arg Leu
    2360             2365             2370

Ala Thr  Gln Pro His Leu Val  Gln Thr Gln Gln Val  Gln Pro Gln
    2375             2380             2385

Asn Leu  Gln Met Gln Gln Gln  Asn Leu Gln Pro Ala  Asn Ile Gln
    2390             2395             2400

Gln Gln  Gln Ser Leu Gln Pro  Pro Pro Pro Pro Gln  Pro His
    2405             2410             2415

Leu Gly  Val Ser Ser Ala Ala  Ser Gly His Leu Gly  Arg Ser Phe
    2420             2425             2430

Leu Ser  Gly Glu Pro Ser Gln  Ala Asp Val Gln Pro  Leu Gly Pro
```

```
                    2435                2440                2445

Ser Ser Leu Ala Val His Thr Ile Leu Pro Gln Glu Ser Pro Ala
    2450                2455                2460

Leu Pro Thr Ser Leu Pro Ser Ser Leu Val Pro Val Thr Ala
2465                2470                2475

Ala Gln Phe Leu Thr Pro Pro Ser Gln His Ser Tyr Ser Ser Pro
    2480                2485                2490

Val Asp Asn Thr Pro Ser His Gln Leu Gln Val Pro Glu His Pro
    2495                2500                2505

Phe Leu Thr Pro Ser Pro Glu Ser Pro Asp Gln Trp Ser Ser Ser
    2510                2515                2520

Ser Pro His Ser Asn Val Ser Asp Trp Ser Glu Gly Val Ser Ser
    2525                2530                2535

Pro Pro Thr Ser Met Gln Ser Gln Ile Ala Arg Ile Pro Glu Ala
    2540                2545                2550

Phe Lys
    2555

<210> SEQ ID NO 5
<211> LENGTH: 724
<212> TYPE: PRT
<213> ORGANISM: Artificial Sequence
<220> FEATURE:
<223> OTHER INFORMATION: human-mouse chimeric sequence

<400> SEQUENCE: 5

Met Val Ser Pro Arg Met Ser Gly Leu Leu Ser Gln Thr Val Ile Leu
1               5                   10                  15

Ala Leu Ile Phe Leu Pro Gln Thr Arg Pro Ala Gly Val Phe Glu Leu
            20                  25                  30

Gln Ile His Ser Phe Gly Pro Gly Pro Gly Ala Pro Arg Ser
        35                  40                  45

Pro Cys Ser Ala Arg Leu Pro Cys Arg Leu Phe Arg Val Cys Leu
    50                  55                  60

Lys Pro Gly Leu Ser Glu Glu Ala Ala Glu Ser Pro Cys Ala Leu Gly
65                  70                  75                  80

Ala Ala Leu Ser Ala Arg Gly Pro Val Tyr Thr Glu Gln Pro Gly Ala
                85                  90                  95

Pro Ala Pro Asp Leu Pro Leu Pro Asp Gly Leu Leu Gln Val Pro Phe
            100                 105                 110

Arg Asp Ala Trp Pro Gly Thr Phe Ser Phe Ile Ile Glu Thr Trp Arg
        115                 120                 125

Glu Glu Leu Gly Asp Gln Ile Gly Gly Pro Ala Trp Ser Leu Leu Ala
    130                 135                 140

Arg Val Ala Gly Arg Arg Leu Ala Ala Gly Gly Pro Trp Ala Arg
145                 150                 155                 160

Asp Ile Gln Arg Ala Gly Ala Trp Glu Leu Arg Phe Ser Tyr Arg Ala
                165                 170                 175

Arg Cys Glu Pro Pro Ala Val Gly Thr Ala Cys Thr Arg Leu Cys Arg
            180                 185                 190

Pro Arg Ser Ala Pro Ser Arg Cys Gly Pro Gly Leu Arg Pro Cys Ala
        195                 200                 205

Pro Leu Glu Asp Glu Cys Glu Ala Pro Leu Val Cys Arg Ala Gly Cys
    210                 215                 220

Ser Pro Glu His Gly Phe Cys Glu Gln Pro Gly Glu Cys Arg Cys Leu
```

-continued

```
            225                 230                 235                 240
Glu Gly Trp Thr Gly Pro Leu Cys Thr Val Pro Val Ser Thr Ser Ser
                245                 250                 255

Cys Leu Ser Pro Arg Gly Pro Ser Ser Ala Thr Thr Gly Cys Leu Val
                260                 265                 270

Pro Gly Pro Gly Pro Cys Asp Gly Asn Pro Cys Ala Asn Gly Gly Ser
                275                 280                 285

Cys Ser Glu Thr Pro Arg Ser Phe Glu Cys Thr Cys Pro Arg Gly Phe
290                 295                 300

Tyr Gly Leu Arg Cys Glu Val Ser Gly Val Thr Cys Ala Asp Gly Pro
305                 310                 315                 320

Cys Phe Asn Gly Gly Leu Cys Val Gly Gly Ala Asp Pro Asp Ser Ala
                325                 330                 335

Tyr Ile Cys His Cys Pro Pro Gly Phe Gln Gly Ser Asn Cys Glu Lys
                340                 345                 350

Arg Val Asp Arg Cys Ser Leu Gln Pro Cys Arg Asn Gly Gly Leu Cys
                355                 360                 365

Leu Asp Leu Gly His Ala Leu Arg Cys Arg Cys Arg Ala Gly Phe Ala
    370                 375                 380

Gly Pro Arg Cys Glu His Asp Leu Asp Asp Cys Ala Gly Arg Ala Cys
385                 390                 395                 400

Ala Asn Gly Gly Thr Cys Val Glu Gly Gly Gly Ala His Arg Cys Ser
                405                 410                 415

Cys Ala Leu Gly Phe Gly Gly Arg Asp Cys Arg Glu Arg Ala Asp Pro
                420                 425                 430

Cys Ala Ala Arg Pro Cys Ala His Gly Gly Arg Cys Tyr Ala His Phe
                435                 440                 445

Ser Gly Leu Val Cys Ala Cys Ala Pro Gly Tyr Met Gly Ala Arg Cys
        450                 455                 460

Glu Phe Pro Val His Pro Asp Gly Ala Ser Ala Leu Pro Ala Ala Pro
465                 470                 475                 480

Pro Gly Leu Arg Pro Gly Asp Pro Gln Arg Tyr Leu Ala Arg Gly Pro
                485                 490                 495

Thr Ile Lys Pro Cys Pro Pro Cys Lys Cys Pro Ala Pro Asn Leu Leu
                500                 505                 510

Gly Gly Pro Ser Val Phe Ile Phe Pro Pro Lys Ile Lys Asp Val Leu
                515                 520                 525

Met Ile Ser Leu Ser Pro Ile Val Thr Cys Val Val Val Asp Val Ser
        530                 535                 540

Glu Asp Asp Pro Asp Val Gln Ile Ser Trp Phe Val Asn Asn Val Glu
545                 550                 555                 560

Val His Thr Ala Gln Thr Gln Thr His Arg Glu Asp Tyr Asn Ser Thr
                565                 570                 575

Leu Arg Val Val Ser Ala Leu Pro Ile Gln His Gln Asp Trp Met Ser
                580                 585                 590

Gly Lys Glu Phe Lys Cys Lys Val Asn Asn Lys Asp Leu Pro Ala Pro
                595                 600                 605

Ile Glu Arg Thr Ile Ser Lys Pro Lys Gly Ser Val Arg Ala Pro Gln
            610                 615                 620

Val Tyr Val Leu Pro Pro Pro Glu Glu Glu Met Thr Lys Lys Gln Val
625                 630                 635                 640

Thr Leu Thr Cys Met Val Thr Asp Phe Met Pro Glu Asp Ile Tyr Val
                645                 650                 655
```

```
Glu Trp Thr Asn Asn Gly Lys Thr Glu Leu Asn Tyr Lys Asn Thr Glu
            660                 665                 670

Pro Val Leu Asp Ser Asp Gly Ser Tyr Phe Met Tyr Ser Lys Leu Arg
            675                 680                 685

Val Glu Lys Lys Asn Trp Val Glu Arg Asn Ser Tyr Ser Cys Ser Val
            690                 695                 700

Val His Glu Gly Leu His Asn His His Thr Thr Lys Ser Phe Ser Arg
705                 710                 715                 720

Thr Pro Gly Lys

<210> SEQ ID NO 6
<211> LENGTH: 575
<212> TYPE: PRT
<213> ORGANISM: Artificial Sequence
<220> FEATURE:
<223> OTHER INFORMATION: human-mouse chimeric sequence

<400> SEQUENCE: 6

Met Val Leu Ala Ser Ser Thr Thr Ser Ile His Thr Met Leu Leu Leu
1               5                   10                  15

Leu Leu Met Leu Ala Gln Pro Ala Met Ala Ala Arg Cys Glu Pro Pro
            20                  25                  30

Ala Val Gly Thr Ala Cys Thr Arg Leu Cys Arg Pro Arg Ser Ala Pro
            35                  40                  45

Ser Arg Cys Gly Pro Gly Leu Arg Pro Cys Ala Pro Leu Glu Asp Glu
            50                  55                  60

Cys Glu Ala Pro Leu Val Cys Arg Ala Gly Cys Ser Pro Glu His Gly
65                  70                  75                  80

Phe Cys Glu Gln Pro Gly Glu Cys Arg Cys Leu Glu Gly Trp Thr Gly
            85                  90                  95

Pro Leu Cys Thr Val Pro Val Ser Thr Ser Ser Cys Leu Ser Pro Arg
            100                 105                 110

Gly Pro Ser Ser Ala Thr Thr Gly Cys Leu Val Pro Gly Pro Gly Pro
            115                 120                 125

Cys Asp Gly Asn Pro Cys Ala Asn Gly Gly Ser Cys Ser Glu Thr Pro
            130                 135                 140

Arg Ser Phe Glu Cys Thr Cys Pro Arg Gly Phe Tyr Gly Leu Arg Cys
145                 150                 155                 160

Glu Val Ser Gly Val Thr Cys Ala Asp Gly Pro Cys Phe Asn Gly Gly
            165                 170                 175

Leu Cys Val Gly Gly Ala Asp Pro Asp Ser Ala Tyr Ile Cys His Cys
            180                 185                 190

Pro Pro Gly Phe Gln Gly Ser Asn Cys Glu Lys Arg Val Asp Arg Cys
            195                 200                 205

Ser Leu Gln Pro Cys Arg Asn Gly Gly Leu Cys Leu Asp Leu Gly His
            210                 215                 220

Ala Leu Arg Cys Arg Cys Arg Ala Gly Phe Ala Gly Pro Arg Cys Glu
225                 230                 235                 240

His Asp Leu Asp Asp Cys Ala Gly Arg Ala Cys Ala Asn Gly Gly Thr
            245                 250                 255

Cys Val Glu Gly Gly Gly Ala His Arg Cys Ser Cys Ala Leu Gly Phe
            260                 265                 270

Gly Gly Arg Asp Cys Arg Glu Arg Ala Asp Pro Cys Ala Ala Arg Pro
            275                 280                 285
```

```
Cys Ala His Gly Gly Arg Cys Tyr Ala His Phe Ser Gly Leu Val Cys
            290                 295                 300

Ala Cys Ala Pro Gly Tyr Met Gly Ala Arg Cys Glu Phe Pro Val His
305                 310                 315                 320

Pro Asp Gly Ala Ser Ala Leu Pro Ala Ala Pro Pro Gly Leu Arg Pro
                325                 330                 335

Gly Asp Pro Gln Arg Tyr Leu Ala Arg Gly Pro Thr Ile Lys Pro Cys
                340                 345                 350

Pro Pro Cys Lys Cys Pro Ala Pro Asn Leu Leu Gly Gly Pro Ser Val
            355                 360                 365

Phe Ile Phe Pro Pro Lys Ile Lys Asp Val Leu Met Ile Ser Leu Ser
370                 375                 380

Pro Ile Val Thr Cys Val Val Asp Val Ser Glu Asp Asp Pro Asp
385                 390                 395                 400

Val Gln Ile Ser Trp Phe Val Asn Asn Val Glu Val His Thr Ala Gln
                405                 410                 415

Thr Gln Thr His Arg Glu Asp Tyr Asn Ser Thr Leu Arg Val Val Ser
                420                 425                 430

Ala Leu Pro Ile Gln His Gln Asp Trp Met Ser Gly Lys Glu Phe Lys
            435                 440                 445

Cys Lys Val Asn Asn Lys Asp Leu Pro Ala Pro Ile Glu Arg Thr Ile
450                 455                 460

Ser Lys Pro Lys Gly Ser Val Arg Ala Pro Gln Val Tyr Val Leu Pro
465                 470                 475                 480

Pro Pro Glu Glu Glu Met Thr Lys Lys Gln Val Thr Leu Thr Cys Met
                485                 490                 495

Val Thr Asp Phe Met Pro Glu Asp Ile Tyr Val Glu Trp Thr Asn Asn
                500                 505                 510

Gly Lys Thr Glu Leu Asn Tyr Lys Asn Thr Glu Pro Val Leu Asp Ser
            515                 520                 525

Asp Gly Ser Tyr Phe Met Tyr Ser Lys Leu Arg Val Glu Lys Lys Asn
            530                 535                 540

Trp Val Glu Arg Asn Ser Tyr Ser Cys Ser Val Val His Glu Gly Leu
545                 550                 555                 560

His Asn His His Thr Thr Lys Ser Phe Ser Arg Thr Pro Gly Lys
                565                 570                 575

<210> SEQ ID NO 7
<211> LENGTH: 535
<212> TYPE: PRT
<213> ORGANISM: Artificial Sequence
<220> FEATURE:
<223> OTHER INFORMATION: human-mouse chimeric sequence

<400> SEQUENCE: 7

Met Val Leu Ala Ser Ser Thr Thr Ser Ile His Thr Met Leu Leu Leu
1               5                   10                  15

Leu Leu Met Leu Ala Gln Pro Ala Met Ala Ala Pro Leu Val Cys Arg
                20                  25                  30

Ala Gly Cys Ser Pro Glu His Gly Phe Cys Glu Gln Pro Gly Glu Cys
            35                  40                  45

Arg Cys Leu Glu Gly Trp Thr Gly Pro Leu Cys Thr Val Pro Val Ser
        50                  55                  60

Thr Ser Ser Cys Leu Ser Pro Arg Gly Pro Ser Ser Ala Thr Thr Gly
65                  70                  75                  80
```

-continued

```
Cys Leu Val Pro Gly Pro Cys Asp Gly Asn Pro Cys Ala Asn
                 85              90              95

Gly Gly Ser Cys Ser Glu Thr Pro Arg Ser Phe Glu Cys Thr Cys Pro
            100                 105                 110

Arg Gly Phe Tyr Gly Leu Arg Cys Glu Val Ser Gly Val Thr Cys Ala
            115                 120                 125

Asp Gly Pro Cys Phe Asn Gly Leu Cys Val Gly Gly Ala Asp Pro
            130                 135             140

Asp Ser Ala Tyr Ile Cys His Cys Pro Gly Phe Gln Gly Ser Asn
145                 150                 155                 160

Cys Glu Lys Arg Val Asp Arg Cys Ser Leu Gln Pro Cys Arg Asn Gly
                165                 170                 175

Gly Leu Cys Leu Asp Leu Gly His Ala Leu Arg Cys Arg Cys Arg Ala
            180                 185                 190

Gly Phe Ala Gly Pro Arg Cys Glu His Asp Leu Asp Asp Cys Ala Gly
            195                 200                 205

Arg Ala Cys Ala Asn Gly Gly Thr Cys Val Glu Gly Gly Ala His
    210                 215                 220

Arg Cys Ser Cys Ala Leu Gly Phe Gly Gly Arg Asp Cys Arg Glu Arg
225                 230                 235                 240

Ala Asp Pro Cys Ala Ala Arg Pro Cys Ala His Gly Gly Arg Cys Tyr
            245                 250                 255

Ala His Phe Ser Gly Leu Val Cys Ala Cys Ala Pro Gly Tyr Met Gly
                260                 265                 270

Ala Arg Cys Glu Phe Pro Val His Pro Asp Gly Ala Ser Ala Leu Pro
            275                 280                 285

Ala Ala Pro Pro Gly Leu Arg Pro Gly Asp Pro Gln Arg Tyr Leu Ala
    290                 295                 300

Arg Gly Pro Thr Ile Lys Pro Cys Pro Pro Cys Lys Cys Pro Ala Pro
305                 310                 315                 320

Asn Leu Leu Gly Gly Pro Ser Val Phe Ile Phe Pro Pro Lys Ile Lys
                325                 330                 335

Asp Val Leu Met Ile Ser Leu Ser Pro Ile Val Thr Cys Val Val Val
            340                 345                 350

Asp Val Ser Glu Asp Asp Pro Asp Val Gln Ile Ser Trp Phe Val Asn
            355                 360                 365

Asn Val Glu Val His Thr Ala Gln Thr Gln Thr His Arg Glu Asp Tyr
            370                 375                 380

Asn Ser Thr Leu Arg Val Val Ser Ala Leu Pro Ile Gln His Gln Asp
385                 390                 395                 400

Trp Met Ser Gly Lys Glu Phe Lys Cys Lys Val Asn Asn Lys Asp Leu
            405                 410                 415

Pro Ala Pro Ile Glu Arg Thr Ile Ser Lys Pro Lys Gly Ser Val Arg
            420                 425                 430

Ala Pro Gln Val Tyr Val Leu Pro Pro Glu Glu Glu Met Thr Lys
    435                 440                 445

Lys Gln Val Thr Leu Thr Cys Met Val Thr Asp Phe Met Pro Glu Asp
    450                 455                 460

Ile Tyr Val Glu Trp Thr Asn Asn Gly Lys Thr Glu Leu Asn Tyr Lys
465                 470                 475                 480

Asn Thr Glu Pro Val Leu Asp Ser Asp Gly Ser Tyr Phe Met Tyr Ser
                485                 490                 495

Lys Leu Arg Val Glu Lys Lys Asn Trp Val Glu Arg Asn Ser Tyr Ser
```

```
                    500                 505                 510
Cys Ser Val Val His Glu Gly Leu His Asn His His Thr Thr Lys Ser
            515                 520                 525
Phe Ser Arg Thr Pro Gly Lys
            530                 535

<210> SEQ ID NO 8
<211> LENGTH: 718
<212> TYPE: PRT
<213> ORGANISM: Artificial Sequence
<220> FEATURE:
<223> OTHER INFORMATION: human-mouse chimeric sequence

<400> SEQUENCE: 8

Met Val Ser Leu Gln Val Ser Pro Leu Ser Gln Thr Leu Ile Leu Ala
1               5                   10                  15

Phe Leu Leu Pro Gln Ala Leu Pro Ala Gly Val Phe Glu Leu Gln Ile
            20                  25                  30

His Ser Phe Gly Pro Gly Pro Gly Leu Gly Thr Pro Arg Ser Pro Cys
        35                  40                  45

Asn Ala Arg Gly Pro Cys Arg Leu Phe Phe Arg Val Cys Leu Lys Pro
    50                  55                  60

Gly Val Ser Gln Glu Ala Thr Glu Ser Leu Cys Ala Leu Gly Ala Ala
65                  70                  75                  80

Leu Ser Thr Ser Val Pro Val Tyr Thr Glu His Pro Gly Glu Ser Ala
                85                  90                  95

Ala Ala Leu Pro Leu Pro Asp Gly Leu Val Arg Val Pro Phe Arg Asp
            100                 105                 110

Ala Trp Pro Gly Thr Phe Ser Leu Val Ile Glu Thr Trp Arg Glu Gln
        115                 120                 125

Leu Gly Glu His Ala Gly Gly Pro Ala Trp Asn Leu Leu Ala Arg Val
    130                 135                 140

Val Gly Arg Arg Arg Leu Ala Ala Gly Gly Pro Trp Ala Arg Asp Val
145                 150                 155                 160

Gln Arg Thr Gly Thr Trp Glu Leu His Phe Ser Tyr Arg Ala Arg Cys
                165                 170                 175

Glu Pro Pro Ala Val Gly Ala Ala Cys Ala Arg Leu Cys Arg Ser Arg
            180                 185                 190

Ser Ala Pro Ser Arg Cys Gly Pro Gly Leu Arg Pro Cys Thr Pro Phe
        195                 200                 205

Pro Asp Glu Cys Glu Ala Pro Ser Val Cys Arg Pro Gly Cys Ser Pro
    210                 215                 220

Glu His Gly Tyr Cys Glu Glu Pro Asp Glu Cys Arg Cys Leu Glu Gly
225                 230                 235                 240

Trp Thr Gly Pro Leu Cys Thr Val Pro Val Ser Thr Ser Ser Cys Leu
                245                 250                 255

Asn Ser Arg Val Pro Gly Pro Ala Ser Thr Gly Cys Leu Leu Pro Gly
            260                 265                 270

Pro Gly Pro Cys Asp Gly Asn Pro Cys Ala Asn Gly Gly Ser Cys Ser
        275                 280                 285

Glu Thr Ser Gly Ser Phe Glu Cys Ala Cys Pro Arg Gly Phe Tyr Gly
    290                 295                 300

Leu Arg Cys Glu Val Ser Gly Val Thr Cys Ala Asp Gly Pro Cys Phe
305                 310                 315                 320

Asn Gly Gly Leu Cys Val Gly Gly Glu Asp Pro Asp Ser Ala Tyr Val
```

```
              325                 330                 335
Cys His Cys Pro Pro Gly Phe Gln Gly Ser Asn Cys Glu Lys Arg Val
            340                 345                 350
Asp Arg Cys Ser Leu Gln Pro Cys Gln Asn Gly Gly Leu Cys Leu Asp
        355                 360                 365
Leu Gly His Ala Leu Arg Cys Arg Cys Arg Ala Gly Phe Ala Gly Pro
    370                 375                 380
Arg Cys Glu His Asp Leu Asp Asp Cys Ala Gly Arg Ala Cys Ala Asn
385                 390                 395                 400
Gly Gly Thr Cys Val Glu Gly Gly Ser Arg Arg Cys Ser Cys Ala
                405                 410                 415
Leu Gly Phe Gly Gly Arg Asp Cys Arg Glu Arg Ala Asp Pro Cys Ala
            420                 425                 430
Ser Arg Pro Cys Ala His Gly Gly Arg Cys Tyr Ala His Phe Ser Gly
        435                 440                 445
Leu Val Cys Ala Cys Ala Pro Gly Tyr Met Gly Val Arg Cys Glu Phe
    450                 455                 460
Ala Val Arg Pro Asp Gly Ala Asp Ala Val Pro Ala Ala Pro Arg Gly
465                 470                 475                 480
Leu Arg Gln Ala Asp Pro Gln Arg Gly Pro Thr Ile Lys Pro Cys Pro
                485                 490                 495
Pro Cys Lys Cys Pro Ala Pro Asn Leu Leu Gly Gly Pro Ser Val Phe
            500                 505                 510
Ile Phe Pro Pro Lys Ile Lys Asp Val Leu Met Ile Ser Leu Ser Pro
        515                 520                 525
Ile Val Thr Cys Val Val Val Asp Val Ser Glu Asp Asp Pro Asp Val
    530                 535                 540
Gln Ile Ser Trp Phe Val Asn Asn Val Glu Val His Thr Ala Gln Thr
545                 550                 555                 560
Gln Thr His Arg Glu Asp Tyr Asn Ser Thr Leu Arg Val Val Ser Ala
                565                 570                 575
Leu Pro Ile Gln His Gln Asp Trp Met Ser Gly Lys Glu Phe Lys Cys
            580                 585                 590
Lys Val Asn Asn Lys Asp Leu Pro Ala Pro Ile Glu Arg Thr Ile Ser
        595                 600                 605
Lys Pro Lys Gly Ser Val Arg Ala Pro Gln Val Tyr Val Leu Pro Pro
    610                 615                 620
Pro Glu Glu Glu Met Thr Lys Lys Gln Val Thr Leu Thr Cys Met Val
625                 630                 635                 640
Thr Asp Phe Met Pro Glu Asp Ile Tyr Val Glu Trp Thr Asn Asn Gly
                645                 650                 655
Lys Thr Glu Leu Asn Tyr Lys Asn Thr Glu Pro Val Leu Asp Ser Asp
            660                 665                 670
Gly Ser Tyr Phe Met Tyr Ser Lys Leu Arg Val Glu Lys Lys Asn Trp
        675                 680                 685
Val Glu Arg Asn Ser Tyr Ser Cys Ser Val Val His Glu Gly Leu His
    690                 695                 700
Asn His His Thr Thr Lys Ser Phe Ser Arg Thr Pro Gly Lys
705                 710                 715
```

<210> SEQ ID NO 9
<211> LENGTH: 121
<212> TYPE: PRT
<213> ORGANISM: Mus musculus

<400> SEQUENCE: 9

Gln Val Gln Leu Gln Gln Ser Gly Ala Asp Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Ile Lys Gln Arg Pro Gly Gln Gly Leu Glu Trp Ile
        35                  40                  45

Gly Val Met Asn Pro Gly Ser Gly Gly Thr His Tyr Ser Glu Lys Phe
    50                  55                  60

Arg Gly Lys Ala Thr Leu Thr Ala Asp Lys Ser Ser Thr Ala Tyr
65                  70                  75                  80

Met Gln Leu Ile Ser Leu Thr Ser Asp Asp Ser Ala Val Tyr Phe Cys
                85                  90                  95

Ala Arg Ser Asp Tyr Asp Tyr Val Thr Tyr Ala Met Asp Tyr Trp Gly
            100                 105                 110

Gln Gly Thr Ser Val Thr Val Ser Ser
            115                 120

<210> SEQ ID NO 10
<211> LENGTH: 464
<212> TYPE: PRT
<213> ORGANISM: Mus musculus

<400> SEQUENCE: 10

Met Glu Trp Ser Gly Val Phe Ile Phe Leu Leu Ser Val Thr Ala Gly
1               5                   10                  15

Val His Ser Gln Val Gln Leu Gln Gln Ser Gly Ala Asp Leu Val Arg
            20                  25                  30

Pro Gly Thr Ser Val Lys Val Ser Cys Lys Ala Ser Gly Tyr Ala Phe
        35                  40                  45

Thr Asn Tyr Leu Ile Glu Trp Ile Lys Gln Arg Pro Gly Gln Gly Leu
    50                  55                  60

Glu Trp Ile Gly Val Met Asn Pro Gly Ser Gly Gly Thr His Tyr Ser
65                  70                  75                  80

Glu Lys Phe Arg Gly Lys Ala Thr Leu Thr Ala Asp Lys Ser Ser Ser
                85                  90                  95

Thr Ala Tyr Met Gln Leu Ile Ser Leu Thr Ser Asp Asp Ser Ala Val
            100                 105                 110

Tyr Phe Cys Ala Arg Ser Asp Tyr Asp Tyr Val Thr Tyr Ala Met Asp
        115                 120                 125

Tyr Trp Gly Gln Gly Thr Ser Val Thr Val Ser Ser Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

```
Asp Cys Gly Cys Lys Pro Cys Ile Cys Thr Val Pro Glu Val Ser Ser
            245                 250                 255

Val Phe Ile Phe Pro Pro Lys Pro Lys Asp Val Leu Thr Ile Thr Leu
            260                 265                 270

Thr Pro Lys Val Thr Cys Val Val Val Asp Ile Ser Lys Asp Asp Pro
            275                 280                 285

Glu Val Gln Phe Ser Trp Phe Val Asp Asp Val Glu Val His Thr Ala
            290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
            325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
            355                 360                 365

Pro Pro Pro Lys Glu Gln Met Ala Lys Asp Lys Val Ser Leu Thr Cys
            370                 375                 380

Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asn
            405                 410                 415

Thr Asn Gly Ser Tyr Phe Val Tyr Ser Lys Leu Asn Val Gln Lys Ser
            420                 425                 430

Asn Trp Glu Ala Gly Asn Thr Phe Thr Cys Ser Val Leu His Glu Gly
            435                 440                 445

Leu His Asn His His Thr Glu Lys Ser Leu Ser His Ser Pro Gly Lys
450                 455                 460

<210> SEQ ID NO 11
<211> LENGTH: 470
<212> TYPE: PRT
<213> ORGANISM: Artificial Sequence
<220> FEATURE:
<223> OTHER INFORMATION: chimeric antibody heavy chain

<400> SEQUENCE: 11

Met Glu Trp Ser Gly Val Phe Ile Phe Leu Leu Ser Val Thr Ala Gly
1               5                   10                  15

Val His Ser Gln Val Gln Leu Gln Gln Ser Gly Ala Asp Leu Val Arg
            20                  25                  30

Pro Gly Thr Ser Val Lys Val Ser Cys Lys Ala Ser Gly Tyr Ala Phe
            35                  40                  45

Thr Asn Tyr Leu Ile Glu Trp Ile Lys Gln Arg Pro Gly Gln Gly Leu
        50                  55                  60

Glu Trp Ile Gly Val Met Asn Pro Gly Ser Gly Gly Thr His Tyr Ser
65                  70                  75                  80

Glu Lys Phe Arg Gly Lys Ala Thr Leu Thr Ala Asp Lys Ser Ser Ser
            85                  90                  95

Thr Ala Tyr Met Gln Leu Ile Ser Leu Thr Ser Asp Asp Ser Ala Val
            100                 105                 110

Tyr Phe Cys Ala Arg Ser Asp Tyr Asp Tyr Val Thr Tyr Ala Met Asp
            115                 120                 125

Tyr Trp Gly Gln Gly Thr Ser Val Thr Val Ser Ser Ala Ser Thr Lys
            130                 135                 140
```

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
450                 455                 460

Ser Leu Ser Pro Gly Lys
465                 470

<210> SEQ ID NO 12
<211> LENGTH: 5
<212> TYPE: PRT
<213> ORGANISM: Mus musculus

<400> SEQUENCE: 12

Asn Tyr Leu Ile Glu
1               5

<210> SEQ ID NO 13
<211> LENGTH: 17
<212> TYPE: PRT

<213> ORGANISM: Mus musculus

<400> SEQUENCE: 13

Val Met Asn Pro Gly Ser Gly Gly Thr His Tyr Ser Glu Lys Phe Arg
1               5                   10                  15

Gly

<210> SEQ ID NO 14
<211> LENGTH: 12
<212> TYPE: PRT
<213> ORGANISM: Mus musculus

<400> SEQUENCE: 14

Ser Asp Tyr Asp Tyr Val Thr Tyr Ala Met Asp Tyr
1               5                   10

<210> SEQ ID NO 15
<211> LENGTH: 107
<212> TYPE: PRT
<213> ORGANISM: Mus musculus

<400> SEQUENCE: 15

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ile Trp Phe Gln Gln Lys Pro Gly Lys Ser Pro Lys Thr Leu Ile
        35                  40                  45

Tyr Arg Thr Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Gly Asp Met Gly Ile Tyr Tyr Cys Leu Gln Tyr Asp Glu Phe Pro Phe
                85                  90                  95

Thr Phe Gly Ser Gly Thr Lys Leu Glu Ile Lys
            100                 105

<210> SEQ ID NO 16
<211> LENGTH: 236
<212> TYPE: PRT
<213> ORGANISM: Mus musculus

<400> SEQUENCE: 16

Met Asp Met Arg Thr Pro Ala Gln Phe Leu Gly Ile Leu Leu Leu Trp
1               5                   10                  15

Phe Pro Gly Ile Lys Cys Asp Ile Lys Met Thr Gln Ser Pro Ser Ser
            20                  25                  30

Met Tyr Ala Ser Leu Gly Glu Arg Val Thr Ile Thr Cys Lys Ala Ser
        35                  40                  45

Gln Asp Ile Asn Ser Tyr Leu Ile Trp Phe Gln Gln Lys Pro Gly Lys
    50                  55                  60

Ser Pro Lys Thr Leu Ile Tyr Arg Thr Asn Arg Leu Val Asp Gly Val
65                  70                  75                  80

Pro Ser Arg Phe Ser Gly Ser Gly Ser Gly Gln Asp Tyr Ser Leu Thr
                85                  90                  95

Ile Ser Ser Leu Glu Tyr Gly Asp Met Gly Ile Tyr Tyr Cys Leu Gln
            100                 105                 110

Tyr Asp Glu Phe Pro Phe Thr Phe Gly Ser Gly Thr Lys Leu Glu Ile

```
            115                 120                 125
Lys Arg Ala Asp Ala Pro Thr Val Ser Ile Phe Pro Pro Ser Ser
        130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
            195                 200                 205

Glu Arg His Asn Ser Tyr Thr Cys Glu Ala Thr His Lys Thr Ser Thr
        210                 215                 220

Ser Pro Ile Val Lys Ser Phe Asn Arg Asn Glu Cys
225                 230                 235
```

<210> SEQ ID NO 17
<211> LENGTH: 236
<212> TYPE: PRT
<213> ORGANISM: Artificial Sequence
<220> FEATURE:
<223> OTHER INFORMATION: chimeric antibody light chain

<400> SEQUENCE: 17

```
Met Asp Met Arg Thr Pro Ala Gln Phe Leu Gly Ile Leu Leu Leu Trp
1               5                   10                  15

Phe Pro Gly Ile Lys Cys Asp Ile Lys Met Thr Gln Ser Pro Ser Ser
                20                  25                  30

Met Tyr Ala Ser Leu Gly Glu Arg Val Thr Ile Thr Cys Lys Ala Ser
            35                  40                  45

Gln Asp Ile Asn Ser Tyr Leu Ile Trp Phe Gln Gln Lys Pro Gly Lys
        50                  55                  60

Ser Pro Lys Thr Leu Ile Tyr Arg Thr Asn Arg Leu Val Asp Gly Val
65                  70                  75                  80

Pro Ser Arg Phe Ser Gly Ser Gly Ser Gly Gln Asp Tyr Ser Leu Thr
                85                  90                  95

Ile Ser Ser Leu Glu Tyr Gly Asp Met Gly Ile Tyr Tyr Cys Leu Gln
            100                 105                 110

Tyr Asp Glu Phe Pro Phe Thr Phe Gly Ser Gly Thr Lys Leu Glu Ile
        115                 120                 125

Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235
```

```
<210> SEQ ID NO 18
<211> LENGTH: 11
<212> TYPE: PRT
<213> ORGANISM: Mus musculus

<400> SEQUENCE: 18

Lys Ala Ser Gln Asp Ile Asn Ser Tyr Leu Ile
1               5                   10

<210> SEQ ID NO 19
<211> LENGTH: 7
<212> TYPE: PRT
<213> ORGANISM: Mus musculus

<400> SEQUENCE: 19

Arg Thr Asn Arg Leu Val Asp
1               5

<210> SEQ ID NO 20
<211> LENGTH: 9
<212> TYPE: PRT
<213> ORGANISM: Mus musculus

<400> SEQUENCE: 20

Leu Gln Tyr Asp Glu Phe Pro Phe Thr
1               5

<210> SEQ ID NO 21
<211> LENGTH: 118
<212> TYPE: PRT
<213> ORGANISM: Mus musculus

<400> SEQUENCE: 21

Glu Val Gln Leu Gln Gln Ser Gly Pro Glu Leu Val Lys Pro Gly Ala
1               5                   10                  15

Ser Val Lys Met Ser Cys Arg Ala Ser Gly Tyr Thr Phe Thr Asp Tyr
            20                  25                  30

Tyr Met Lys Trp Val Lys Gln Ser His Gly Lys Ser Leu Glu Trp Ile
        35                  40                  45

Gly Asp Ile Asn Pro Asn Asn Gly Asp Thr Phe Tyr Asn Gln Lys Phe
    50                  55                  60

Lys Gly Lys Ala Thr Leu Thr Ile Asp Lys Ser Ser Ser Thr Ala Tyr
65                  70                  75                  80

Met Gln Leu Asn Ser Leu Thr Ser Asp Asp Ser Ala Val Tyr Tyr Cys
                85                  90                  95

Ala Arg Asp Gly Asn Tyr Ala Tyr Phe Asp Tyr Trp Gly Gln Gly Thr
            100                 105                 110

Thr Leu Thr Val Ser Ser
        115

<210> SEQ ID NO 22
<211> LENGTH: 461
<212> TYPE: PRT
<213> ORGANISM: Mus musculus

<400> SEQUENCE: 22

Met Gly Trp Ser Trp Ile Phe Leu Phe Leu Leu Ser Gly Thr Gly Gly
1               5                   10                  15

Val Leu Ser Glu Val Gln Leu Gln Gln Ser Gly Pro Glu Leu Val Lys
            20                  25                  30

Pro Gly Ala Ser Val Lys Met Ser Cys Arg Ala Ser Gly Tyr Thr Phe
```

```
                35                  40                  45
Thr Asp Tyr Tyr Met Lys Trp Val Lys Gln Ser His Gly Lys Ser Leu
 50                  55                  60

Glu Trp Ile Gly Asp Ile Asn Pro Asn Asn Gly Asp Thr Phe Tyr Asn
 65                  70                  75                  80

Gln Lys Phe Lys Gly Lys Ala Thr Leu Thr Ile Asp Lys Ser Ser Ser
                 85                  90                  95

Thr Ala Tyr Met Gln Leu Asn Ser Leu Thr Ser Asp Asp Ser Ala Val
                100                 105                 110

Tyr Tyr Cys Ala Arg Asp Gly Asn Tyr Ala Tyr Phe Asp Tyr Trp Gly
            115                 120                 125

Gln Gly Thr Thr Leu Thr Val Ser Ser Ala Lys Thr Thr Pro Pro Ser
130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
                165                 170                 175

Thr Trp Asn Ser Gly Ser Leu Ser Ser Gly Val His Thr Phe Pro Ala
                180                 185                 190

Val Leu Gln Ser Asp Leu Tyr Thr Leu Ser Ser Ser Val Thr Val Pro
            195                 200                 205

Ser Ser Thr Trp Pro Ser Glu Thr Val Thr Cys Asn Val Ala His Pro
210                 215                 220

Ala Ser Ser Thr Lys Val Asp Lys Lys Ile Val Pro Arg Asp Cys Gly
225                 230                 235                 240

Cys Lys Pro Cys Ile Cys Thr Val Pro Glu Val Ser Ser Val Phe Ile
                245                 250                 255

Phe Pro Pro Lys Pro Lys Asp Val Leu Thr Ile Thr Leu Thr Pro Lys
                260                 265                 270

Val Thr Cys Val Val Val Asp Ile Ser Lys Asp Asp Pro Glu Val Gln
            275                 280                 285

Phe Ser Trp Phe Val Asp Asp Val Glu Val His Thr Ala Gln Thr Gln
290                 295                 300

Pro Arg Glu Glu Gln Phe Asn Ser Thr Phe Arg Ser Val Ser Glu Leu
305                 310                 315                 320

Pro Ile Met His Gln Asp Trp Leu Asn Gly Lys Glu Phe Lys Cys Arg
                325                 330                 335

Val Asn Ser Ala Ala Phe Pro Ala Pro Ile Glu Lys Thr Ile Ser Lys
                340                 345                 350

Thr Lys Gly Arg Pro Lys Ala Pro Gln Val Tyr Thr Ile Pro Pro Pro
            355                 360                 365

Lys Glu Gln Met Ala Lys Asp Lys Val Ser Leu Thr Cys Met Ile Thr
370                 375                 380

Asp Phe Phe Pro Glu Asp Ile Thr Val Glu Trp Gln Trp Asn Gly Gln
385                 390                 395                 400

Pro Ala Glu Asn Tyr Lys Asn Thr Gln Pro Ile Met Asn Thr Asn Gly
                405                 410                 415

Ser Tyr Phe Val Tyr Ser Lys Leu Asn Val Gln Lys Ser Asn Trp Glu
                420                 425                 430

Ala Gly Asn Thr Phe Thr Cys Ser Val Leu His Glu Gly Leu His Asn
            435                 440                 445

His His Thr Glu Lys Ser Leu Ser His Ser Pro Gly Lys
450                 455                 460
```

<210> SEQ ID NO 23
<211> LENGTH: 467
<212> TYPE: PRT
<213> ORGANISM: Artificial Sequence
<220> FEATURE:
<223> OTHER INFORMATION: chimeric antibody heavy chain

<400> SEQUENCE: 23

```
Met Gly Trp Ser Trp Ile Phe Leu Phe Leu Leu Ser Gly Thr Gly Gly
1               5                   10                  15

Val Leu Ser Glu Val Gln Leu Gln Gln Ser Gly Pro Glu Leu Val Lys
            20                  25                  30

Pro Gly Ala Ser Val Lys Met Ser Cys Arg Ala Ser Gly Tyr Thr Phe
        35                  40                  45

Thr Asp Tyr Tyr Met Lys Trp Val Lys Gln Ser His Gly Lys Ser Leu
    50                  55                  60

Glu Trp Ile Gly Asp Ile Asn Pro Asn Asn Gly Asp Thr Phe Tyr Asn
65                  70                  75                  80

Gln Lys Phe Lys Gly Lys Ala Thr Leu Thr Ile Asp Lys Ser Ser Ser
                85                  90                  95

Thr Ala Tyr Met Gln Leu Asn Ser Leu Thr Ser Asp Asp Ser Ala Val
            100                 105                 110

Tyr Tyr Cys Ala Arg Asp Gly Asn Tyr Ala Tyr Phe Asp Tyr Trp Gly
        115                 120                 125

Gln Gly Thr Thr Leu Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365
```

Tyr Thr Leu Pro Pro Ser Arg Asp Glu Leu Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 24
<211> LENGTH: 5
<212> TYPE: PRT
<213> ORGANISM: Mus musculus

<400> SEQUENCE: 24

Asp Tyr Tyr Met Lys
1               5

<210> SEQ ID NO 25
<211> LENGTH: 17
<212> TYPE: PRT
<213> ORGANISM: Mus musculus

<400> SEQUENCE: 25

Asp Ile Asn Pro Asn Asn Gly Asp Thr Phe Tyr Asn Gln Lys Phe Lys
1               5                   10                  15

Gly

<210> SEQ ID NO 26
<211> LENGTH: 9
<212> TYPE: PRT
<213> ORGANISM: Mus musculus

<400> SEQUENCE: 26

Asp Gly Asn Tyr Ala Tyr Phe Asp Tyr
1               5

<210> SEQ ID NO 27
<211> LENGTH: 111
<212> TYPE: PRT
<213> ORGANISM: Mus musculus

<400> SEQUENCE: 27

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Phe Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

```
Pro Val Glu Glu Asp Ala Ala Thr Tyr Tyr Cys Gln His Ser Arg
                85                  90                  95

His Leu Pro Trp Thr Phe Gly Gly Gly Thr Lys Leu Glu Ile Lys
            100                 105                 110

<210> SEQ ID NO 28
<211> LENGTH: 238
<212> TYPE: PRT
<213> ORGANISM: Mus musculus

<400> SEQUENCE: 28

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Lys Ser
        35                  40                  45

Val Ser Thr Ser Gly Tyr Ser Tyr Met His Trp Tyr Gln Gln Lys Pro
    50                  55                  60

Gly Gln Pro Pro Lys Leu Leu Ile Phe Leu Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Asp Ala Ala Thr Tyr Tyr Cys
            100                 105                 110

Gln His Ser Arg His Leu Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 29
<211> LENGTH: 238
<212> TYPE: PRT
<213> ORGANISM: Artificial Sequence
<220> FEATURE:
<223> OTHER INFORMATION: chimeric antibody light chain

<400> SEQUENCE: 29

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Lys Ser
        35                  40                  45
```

Val Ser Thr Ser Gly Tyr Ser Tyr Met His Trp Tyr Gln Gln Lys Pro
        50                  55                  60

Gly Gln Pro Pro Lys Leu Leu Ile Phe Leu Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Asp Ala Ala Thr Tyr Tyr Cys
            100                 105                 110

Gln His Ser Arg His Leu Pro Trp Thr Phe Gly Gly Gly Thr Lys Leu
            115                 120                 125

Glu Ile Lys Arg Thr Val Ala Ala Pro Ser Val Phe Ile Phe Pro Pro
        130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 30
<211> LENGTH: 15
<212> TYPE: PRT
<213> ORGANISM: Mus musculus

<400> SEQUENCE: 30

Arg Ala Ser Lys Ser Val Ser Thr Ser Gly Tyr Ser Tyr Met His
1               5                   10                  15

<210> SEQ ID NO 31
<211> LENGTH: 7
<212> TYPE: PRT
<213> ORGANISM: Mus musculus

<400> SEQUENCE: 31

Leu Ala Ser Asn Leu Glu Ser
1               5

<210> SEQ ID NO 32
<211> LENGTH: 9
<212> TYPE: PRT
<213> ORGANISM: Mus musculus

<400> SEQUENCE: 32

Gln His Ser Arg His Leu Pro Trp Thr
1               5

<210> SEQ ID NO 33
<211> LENGTH: 119
<212> TYPE: PRT
<213> ORGANISM: Mus musculus

<400> SEQUENCE: 33

Gln Val Gln Leu Gln Gln Ser Gly Gly Asp Leu Met Lys Pro Gly Ala
1               5                   10                  15

Ser Val Lys Ile Ser Cys Lys Ala Ala Gly Tyr Thr Phe Ser Asn Tyr
            20                  25                  30

Tyr Ile Glu Trp Val Lys Gln Arg Pro Gly His Gly Leu Glu Trp Ile
        35                  40                  45

Gly Glu Ile Leu Pro Gly Ser Gly Ser Thr Thr Tyr Asn Glu Lys Phe
 50                  55                  60

Lys Gly Lys Ala Ser Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Trp Gly Ala Arg Glu Pro Gly Phe Pro Tyr Trp Gly Gln Gly
            100                 105                 110

Thr Leu Val Thr Val Ser Ala
            115

<210> SEQ ID NO 34
<211> LENGTH: 462
<212> TYPE: PRT
<213> ORGANISM: Mus musculus

<400> SEQUENCE: 34

Met Glu Trp Thr Trp Val Phe Leu Phe Leu Leu Ser Val Thr Ala Gly
1               5                   10                  15

Val His Ser Gln Val Gln Leu Gln Gln Ser Gly Gly Asp Leu Met Lys
            20                  25                  30

Pro Gly Ala Ser Val Lys Ile Ser Cys Lys Ala Ala Gly Tyr Thr Phe
        35                  40                  45

Ser Asn Tyr Tyr Ile Glu Trp Val Lys Gln Arg Pro Gly His Gly Leu
 50                  55                  60

Glu Trp Ile Gly Glu Ile Leu Pro Gly Ser Gly Ser Thr Thr Tyr Asn
65                  70                  75                  80

Glu Lys Phe Lys Gly Lys Ala Ser Phe Thr Ala Asp Thr Ser Ser Asn
                85                  90                  95

Thr Ala Tyr Met Gln Leu Ser Ser Leu Thr Ser Glu Asp Ser Ala Val
            100                 105                 110

Tyr Tyr Cys Ala Arg Trp Gly Ala Arg Glu Pro Gly Phe Pro Tyr Trp
        115                 120                 125

Gly Gln Gly Thr Leu Val Thr Val Ser Ala Ala Lys Thr Thr Pro Pro
130                 135                 140

Ser Val Tyr Pro Leu Ala Pro Gly Ser Ala Ala Gln Thr Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ser Leu Ser Ser Gly Val His Thr Phe Pro
            180                 185                 190

Ala Val Leu Gln Ser Asp Leu Tyr Thr Leu Ser Ser Ser Val Thr Val
        195                 200                 205

Pro Ser Ser Thr Trp Pro Ser Glu Thr Val Thr Cys Asn Val Ala His
210                 215                 220

Pro Ala Ser Ser Thr Lys Val Asp Lys Lys Ile Val Pro Arg Asp Cys
225                 230                 235                 240

Gly Cys Lys Pro Cys Ile Cys Thr Val Pro Glu Val Ser Ser Val Phe
                245                 250                 255

Ile Phe Pro Pro Lys Pro Lys Asp Val Leu Thr Ile Thr Leu Thr Pro

```
            260                 265                 270
Lys Val Thr Cys Val Val Asp Ile Ser Lys Asp Asp Pro Glu Val
        275                 280                 285

Gln Phe Ser Trp Phe Val Asp Asp Val Glu Val His Thr Ala Gln Thr
    290                 295                 300

Gln Pro Arg Glu Glu Gln Phe Asn Ser Thr Phe Arg Ser Val Ser Glu
305                 310                 315                 320

Leu Pro Ile Met His Gln Asp Trp Leu Asn Gly Lys Glu Phe Lys Cys
                325                 330                 335

Arg Val Asn Ser Ala Ala Phe Pro Ala Pro Ile Glu Lys Thr Ile Ser
            340                 345                 350

Lys Thr Lys Gly Arg Pro Lys Ala Pro Gln Val Tyr Thr Ile Pro Pro
        355                 360                 365

Pro Lys Glu Gln Met Ala Lys Asp Lys Val Ser Leu Thr Cys Met Ile
    370                 375                 380

Thr Asp Phe Phe Pro Glu Asp Ile Thr Val Glu Trp Gln Trp Asn Gly
385                 390                 395                 400

Gln Pro Ala Glu Asn Tyr Lys Asn Thr Gln Pro Ile Met Asn Thr Asn
                405                 410                 415

Gly Ser Tyr Phe Val Tyr Ser Lys Leu Asn Val Gln Lys Ser Asn Trp
            420                 425                 430

Glu Ala Gly Asn Thr Phe Thr Cys Ser Val Leu His Glu Gly Leu His
        435                 440                 445

Asn His His Thr Glu Lys Ser Leu Ser His Ser Pro Gly Lys
    450                 455                 460

<210> SEQ ID NO 35
<211> LENGTH: 468
<212> TYPE: PRT
<213> ORGANISM: Artificial Sequence
<220> FEATURE:
<223> OTHER INFORMATION: chimeric antibody heavy chain

<400> SEQUENCE: 35

Met Glu Trp Thr Trp Val Phe Leu Phe Leu Leu Ser Val Thr Ala Gly
1               5                   10                  15

Val His Ser Gln Val Gln Leu Gln Gln Ser Gly Gly Asp Leu Met Lys
            20                  25                  30

Pro Gly Ala Ser Val Lys Ile Ser Cys Lys Ala Ala Gly Tyr Thr Phe
        35                  40                  45

Ser Asn Tyr Tyr Ile Glu Trp Val Lys Gln Arg Pro Gly His Gly Leu
    50                  55                  60

Glu Trp Ile Gly Glu Ile Leu Pro Gly Ser Gly Ser Thr Thr Tyr Asn
65                  70                  75                  80

Glu Lys Phe Lys Gly Lys Ala Ser Phe Thr Ala Asp Thr Ser Ser Asn
                85                  90                  95

Thr Ala Tyr Met Gln Leu Ser Ser Leu Thr Ser Glu Asp Ser Ala Val
            100                 105                 110

Tyr Tyr Cys Ala Arg Trp Gly Ala Arg Glu Pro Gly Phe Pro Tyr Trp
        115                 120                 125

Gly Gln Gly Thr Leu Val Thr Val Ser Ala Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
```

```
                165                 170                 175
Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
            195                 200                 205

Val Pro Ser Ser Ser Leu Gly Thr Gln Thr Tyr Ile Cys Asn Val Asn
            210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
            290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Asp Glu Leu Thr Lys Asn Gln Val
            370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
            450                 455                 460

Ser Pro Gly Lys
465

<210> SEQ ID NO 36
<211> LENGTH: 5
<212> TYPE: PRT
<213> ORGANISM: Mus musculus

<400> SEQUENCE: 36

Asn Tyr Tyr Ile Glu
1               5

<210> SEQ ID NO 37
<211> LENGTH: 17
<212> TYPE: PRT
<213> ORGANISM: Mus musculus

<400> SEQUENCE: 37

Glu Ile Leu Pro Gly Ser Gly Ser Thr Thr Tyr Asn Glu Lys Phe Lys
```

-continued

```
1               5                   10                  15
Gly

<210> SEQ ID NO 38
<211> LENGTH: 10
<212> TYPE: PRT
<213> ORGANISM: Mus musculus

<400> SEQUENCE: 38

Trp Gly Ala Arg Glu Pro Gly Phe Pro Tyr
1               5                   10

<210> SEQ ID NO 39
<211> LENGTH: 107
<212> TYPE: PRT
<213> ORGANISM: Mus musculus

<400> SEQUENCE: 39

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Asn Tyr Pro Leu
                85                  90                  95

Thr Phe Gly Ala Gly Thr Lys Leu Glu Leu Lys
            100                 105

<210> SEQ ID NO 40
<211> LENGTH: 238
<212> TYPE: PRT
<213> ORGANISM: Mus musculus

<400> SEQUENCE: 40

Met Gly Ile Lys Met Glu Ser Gln Thr Gln Val Phe Val Tyr Met Leu
1               5                   10                  15

Leu Trp Leu Ser Gly Val Asp Gly Asp Ile Val Met Thr Gln Ser Gln
            20                  25                  30

Lys Phe Met Ser Thr Ser Val Gly Asp Arg Val Ser Val Thr Cys Lys
        35                  40                  45

Ala Ser Gln Asn Val Gly Thr Asn Val Ala Trp Tyr Gln Gln Lys Pro
    50                  55                  60

Gly Gln Ser Pro Lys Ala Leu Ile Tyr Ser Ala Ser Tyr Arg Tyr Ser
65                  70                  75                  80

Gly Val Pro Asp Arg Phe Thr Gly Ser Gly Ser Gly Thr Asp Phe Thr
                85                  90                  95

Leu Thr Ile Ser Asn Val Gln Ser Glu Asp Leu Ala Glu Tyr Phe Cys
            100                 105                 110

Gln Gln Tyr Asn Asn Tyr Pro Leu Thr Phe Gly Ala Gly Thr Lys Leu
        115                 120                 125

Glu Leu Lys Arg Ala Asp Ala Ala Pro Thr Val Ser Ile Phe Pro Pro
    130                 135                 140
```

```
Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235
```

<210> SEQ ID NO 41
<211> LENGTH: 238
<212> TYPE: PRT
<213> ORGANISM: Artificial Sequence
<220> FEATURE:
<223> OTHER INFORMATION: chimeric antibody light chain

<400> SEQUENCE: 41

```
Met Gly Ile Lys Met Glu Ser Gln Thr Gln Val Phe Val Tyr Met Leu
1               5                   10                  15

Leu Trp Leu Ser Gly Val Asp Gly Asp Ile Val Met Thr Gln Ser Gln
            20                  25                  30

Lys Phe Met Ser Thr Ser Val Gly Asp Arg Val Ser Val Thr Cys Lys
        35                  40                  45

Ala Ser Gln Asn Val Gly Thr Asn Val Ala Trp Tyr Gln Gln Lys Pro
50                  55                  60

Gly Gln Ser Pro Lys Ala Leu Ile Tyr Ser Ala Ser Tyr Arg Tyr Ser
65                  70                  75                  80

Gly Val Pro Asp Arg Phe Thr Gly Ser Gly Ser Gly Thr Asp Phe Thr
                85                  90                  95

Leu Thr Ile Ser Asn Val Gln Ser Glu Asp Leu Ala Glu Tyr Phe Cys
            100                 105                 110

Gln Gln Tyr Asn Asn Tyr Pro Leu Thr Phe Gly Ala Gly Thr Lys Leu
        115                 120                 125

Glu Leu Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 42
<211> LENGTH: 11
<212> TYPE: PRT
<213> ORGANISM: Mus musculus

```
<400> SEQUENCE: 42

Lys Ala Ser Gln Asn Val Gly Thr Asn Val Ala
1               5                   10

<210> SEQ ID NO 43
<211> LENGTH: 7
<212> TYPE: PRT
<213> ORGANISM: Mus musculus

<400> SEQUENCE: 43

Ser Ala Ser Tyr Arg Tyr Ser
1               5

<210> SEQ ID NO 44
<211> LENGTH: 9
<212> TYPE: PRT
<213> ORGANISM: Mus musculus

<400> SEQUENCE: 44

Gln Gln Tyr Asn Asn Tyr Pro Leu Thr
1               5

<210> SEQ ID NO 45
<211> LENGTH: 123
<212> TYPE: PRT
<213> ORGANISM: Mus musculus

<400> SEQUENCE: 45

Glu Val Lys Leu Val Glu Ser Gly Gly Gly Leu Val Gln Pro Gly Gly
1               5                   10                  15

Ser Leu Ser Leu Ser Cys Ala Ala Ser Gly Phe Thr Phe Thr Asp Tyr
            20                  25                  30

Tyr Met Asn Trp Val Arg Gln Pro Pro Gly Lys Ala Leu Glu Trp Leu
        35                  40                  45

Ala Leu Ile Arg Asn Lys Ala Asn Gly Tyr Thr Thr Glu Tyr Asn Ala
    50                  55                  60

Ser Val Lys Gly Arg Phe Thr Ile Ser Arg Asp Asn Ser Gln Asn Ile
65                  70                  75                  80

Leu Tyr Leu Gln Met Asn Ala Leu Arg Ala Glu Asp Ser Ala Thr Tyr
                85                  90                  95

Tyr Cys Ala Arg Asp Ser Asp Gly Tyr Tyr Glu Tyr Tyr Phe Asp Tyr
            100                 105                 110

Trp Gly Gln Gly Thr Thr Leu Thr Val Ser Ser
        115                 120

<210> SEQ ID NO 46
<211> LENGTH: 466
<212> TYPE: PRT
<213> ORGANISM: Mus musculus

<400> SEQUENCE: 46

Met Lys Leu Trp Leu Asn Trp Ile Phe Leu Val Thr Leu Leu Asn Gly
1               5                   10                  15

Ile Gln Cys Glu Val Lys Leu Val Glu Ser Gly Gly Gly Leu Val Gln
            20                  25                  30

Pro Gly Gly Ser Leu Ser Leu Ser Cys Ala Ala Ser Gly Phe Thr Phe
        35                  40                  45

Thr Asp Tyr Tyr Met Asn Trp Val Arg Gln Pro Pro Gly Lys Ala Leu
    50                  55                  60
```

```
Glu Trp Leu Ala Leu Ile Arg Asn Lys Ala Asn Gly Tyr Thr Thr Glu
 65                  70                  75                  80

Tyr Asn Ala Ser Val Lys Gly Arg Phe Thr Ile Ser Arg Asp Asn Ser
                 85                  90                  95

Gln Asn Ile Leu Tyr Leu Gln Met Asn Ala Leu Arg Ala Glu Asp Ser
            100                 105                 110

Ala Thr Tyr Tyr Cys Ala Arg Asp Ser Asp Gly Tyr Glu Tyr Tyr
            115                 120                 125

Phe Asp Tyr Trp Gly Gln Gly Thr Thr Leu Thr Val Ser Ser Ala Lys
        130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Val Glu Val His
    290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu
    370                 375                 380

Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asn Thr Asn Gly Ser Tyr Phe Val Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys
465
```

```
<210> SEQ ID NO 47
<211> LENGTH: 472
<212> TYPE: PRT
<213> ORGANISM: Artificial Sequence
<220> FEATURE:
<223> OTHER INFORMATION: chimeric antibody heavy chain

<400> SEQUENCE: 47
```

Met Lys Leu Trp Leu Asn Trp Ile Phe Leu Val Thr Leu Leu Asn Gly
1               5                   10                  15

Ile Gln Cys Glu Val Lys Leu Val Glu Ser Gly Gly Gly Leu Val Gln
            20                  25                  30

Pro Gly Gly Ser Leu Ser Leu Ser Cys Ala Ala Ser Gly Phe Thr Phe
        35                  40                  45

Thr Asp Tyr Tyr Met Asn Trp Val Arg Gln Pro Pro Gly Lys Ala Leu
    50                  55                  60

Glu Trp Leu Ala Leu Ile Arg Asn Lys Ala Asn Gly Tyr Thr Thr Glu
65                  70                  75                  80

Tyr Asn Ala Ser Val Lys Gly Arg Phe Thr Ile Ser Arg Asp Asn Ser
                85                  90                  95

Gln Asn Ile Leu Tyr Leu Gln Met Asn Ala Leu Arg Ala Glu Asp Ser
            100                 105                 110

Ala Thr Tyr Tyr Cys Ala Arg Asp Ser Asp Gly Tyr Tyr Glu Tyr Tyr
        115                 120                 125

Phe Asp Tyr Trp Gly Gln Gly Thr Thr Leu Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr

```
                    370                 375                 380
Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
                435                 440                 445

Ser Cys Ser Val Met His Glu Ala Leu His Asn His Tyr Thr Gln Lys
                450                 455                 460

Ser Leu Ser Leu Ser Pro Gly Lys
465                 470

<210> SEQ ID NO 48
<211> LENGTH: 5
<212> TYPE: PRT
<213> ORGANISM: Mus musculus

<400> SEQUENCE: 48

Asp Tyr Tyr Met Asn
1               5

<210> SEQ ID NO 49
<211> LENGTH: 19
<212> TYPE: PRT
<213> ORGANISM: Mus musculus

<400> SEQUENCE: 49

Leu Ile Arg Asn Lys Ala Asn Gly Tyr Thr Thr Glu Tyr Asn Ala Ser
1               5                   10                  15

Val Lys Gly

<210> SEQ ID NO 50
<211> LENGTH: 12
<212> TYPE: PRT
<213> ORGANISM: Mus musculus

<400> SEQUENCE: 50

Asp Ser Asp Gly Tyr Tyr Glu Tyr Tyr Phe Asp Tyr
1               5                   10

<210> SEQ ID NO 51
<211> LENGTH: 107
<212> TYPE: PRT
<213> ORGANISM: Mus musculus

<400> SEQUENCE: 51

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Asp Tyr
                20                  25                  30

Leu Ser Trp Leu Gln Gln Lys Pro Asp Gly Thr Ile Lys Arg Leu Ile
            35                  40                  45

Phe Ala Ala Ser Thr Leu Asp Ser Gly Val Pro Lys Arg Phe Ser Gly
        50                  55                  60

Ser Arg Ser Gly Ser Asp Phe Ser Leu Ser Ile Ser Ser Leu Glu Ser
65                  70                  75                  80

Glu Asp Phe Ala Asp Tyr Tyr Cys Leu Gln Tyr Ala Ser Tyr Pro Tyr
```

```
                        85                  90                  95

Thr Phe Gly Ser Gly Thr Lys Leu Glu Ile Lys
            100                 105

<210> SEQ ID NO 52
<211> LENGTH: 236
<212> TYPE: PRT
<213> ORGANISM: Mus musculus

<400> SEQUENCE: 52

Met Asp Met Arg Val Pro Ala His Val Phe Gly Phe Leu Leu Leu Trp
1               5                   10                  15

Phe Pro Gly Thr Arg Cys Asp Ile Gln Met Thr Gln Ser Pro Ser Ser
            20                  25                  30

Leu Ser Ala Ser Leu Gly Glu Arg Val Ser Leu Thr Cys Arg Ala Ser
        35                  40                  45

Gln Glu Ile Ser Asp Tyr Leu Ser Trp Leu Gln Gln Lys Pro Asp Gly
    50                  55                  60

Thr Ile Lys Arg Leu Ile Phe Ala Ala Ser Thr Leu Asp Ser Gly Val
65                  70                  75                  80

Pro Lys Arg Phe Ser Gly Ser Arg Ser Gly Ser Asp Phe Ser Leu Ser
                85                  90                  95

Ile Ser Ser Leu Glu Ser Glu Asp Phe Ala Asp Tyr Tyr Cys Leu Gln
            100                 105                 110

Tyr Ala Ser Tyr Pro Tyr Thr Phe Gly Ser Gly Thr Lys Leu Glu Ile
        115                 120                 125

Lys Arg Ala Asp Ala Ala Pro Thr Val Ser Ile Phe Pro Pro Ser Ser
    130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
    210                 215                 220

Ser Pro Ile Val Lys Ser Phe Asn Arg Asn Glu Cys
225                 230                 235

<210> SEQ ID NO 53
<211> LENGTH: 236
<212> TYPE: PRT
<213> ORGANISM: Artificial Sequence
<220> FEATURE:
<223> OTHER INFORMATION: chimeric antibody light chain

<400> SEQUENCE: 53

Met Asp Met Arg Val Pro Ala His Val Phe Gly Phe Leu Leu Leu Trp
1               5                   10                  15

Phe Pro Gly Thr Arg Cys Asp Ile Gln Met Thr Gln Ser Pro Ser Ser
            20                  25                  30

Leu Ser Ala Ser Leu Gly Glu Arg Val Ser Leu Thr Cys Arg Ala Ser
        35                  40                  45

Gln Glu Ile Ser Asp Tyr Leu Ser Trp Leu Gln Gln Lys Pro Asp Gly
    50                  55                  60
```

Thr Ile Lys Arg Leu Ile Phe Ala Ala Ser Thr Leu Asp Ser Gly Val
 65                  70                  75                  80

Pro Lys Arg Phe Ser Gly Ser Arg Ser Gly Ser Asp Phe Ser Leu Ser
                 85                  90                  95

Ile Ser Ser Leu Glu Ser Glu Asp Phe Ala Asp Tyr Tyr Cys Leu Gln
            100                 105                 110

Tyr Ala Ser Tyr Pro Tyr Thr Phe Gly Ser Gly Thr Lys Leu Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 54
<211> LENGTH: 11
<212> TYPE: PRT
<213> ORGANISM: Mus musculus

<400> SEQUENCE: 54

Arg Ala Ser Gln Glu Ile Ser Asp Tyr Leu Ser
1               5                   10

<210> SEQ ID NO 55
<211> LENGTH: 7
<212> TYPE: PRT
<213> ORGANISM: Mus musculus

<400> SEQUENCE: 55

Ala Ala Ser Thr Leu Asp Ser
1               5

<210> SEQ ID NO 56
<211> LENGTH: 9
<212> TYPE: PRT
<213> ORGANISM: Mus musculus

<400> SEQUENCE: 56

Leu Gln Tyr Ala Ser Tyr Pro Tyr Thr
1               5

<210> SEQ ID NO 57
<211> LENGTH: 1857
<212> TYPE: DNA
<213> ORGANISM: homo sapiens

<400> SEQUENCE: 57
atggtctccc cacgcgatgtc cgggctcctc tcccagactg tgatcctagc gctcattttc     60
ctcccccaga cacggcccgc tggcgtcttc gagctgcaga tccactcttt cgggccgggt    120

-continued

| | |
|---|---|
| ccaggccctg gggccccgcg gtcccctgc agcgcccggc tccctgccg cctcttcttc | 180 |
| agagtctgcc tgaagcctgg gctctcagag gaggccgccg agtccccgtg cgccctgggc | 240 |
| gcggcgctga gtgcgcgcgg accggtctac accgagcagc ccggagcgcc cgcgcctgat | 300 |
| ctcccactgc ccgacggcct cttgcaggtg cccttccggg acgcctggcc tggcaccttc | 360 |
| tctttcatca tcgaaacctg gagagaggag ttaggagacc agattggagg gcccgcctgg | 420 |
| agcctgctgg cgcgcgtggc tggcaggcgg cgcttggcag ccggaggccc gtgggccgg | 480 |
| gacattcagc gcgcaggcgc ctgggagctg cgcttctcgt accgcgcgcg ctgcgagccg | 540 |
| cctgccgtcg ggaccgcgtg cacgcgcctc tgccgtccgc gcagcgcccc ctcgcggtgc | 600 |
| ggtccgggac tgcgcccctg cgcaccgctc gaggacgaat gtgaggcgcc gctggtgtgc | 660 |
| cgagcaggct gcagccctga gcatggcttc tgtgaacagc ccggtgaatg ccgatgccta | 720 |
| gagggctgga ctggaccct ctgcacgtc cctgtctcca ccagcagctg cctcagcccc | 780 |
| aggggcccgt cctctgctac caccggatgc cttgtccctg gcctgggcc ctgtgacggg | 840 |
| aacccgtgtg ccaatggagg cagctgtagt gagacaccca ggtcctttga atgcacctgc | 900 |
| ccgcgtgggt tctacgggct cggtgtgag gtgagcgggg tgacatgtgc agatggaccc | 960 |
| tgcttcaacg gcggcttgtg tgtcgggggt gcagaccctg actctgccta catctgccac | 1020 |
| tgcccacccg gtttccaagg ctccaactgt gagaagaggg tggaccggtg cagcctgcag | 1080 |
| ccatgccgca atggcggact ctgcctggac ctggccacg ccctgcgctg ccgctgccgc | 1140 |
| gccggcttcg cgggtcctcg ctgcgagcac gacctggacg actgcgcggg ccgcgcctgc | 1200 |
| gctaacggcg gcacgtgtgt ggagggcggc ggcgcgcacc gctgctcctg cgcgctgggc | 1260 |
| ttcggcggcc gcgactgccg cgagcgcgcg gacccgtgcg ccgcgcgccc ctgtgctcac | 1320 |
| ggcggccgct gctacgccca cttctccggc ctcgtctgcg cttgcgctcc cggctacatg | 1380 |
| ggagcgcggt gtgagttccc agtgcacccc gacggcgcaa gcgccttgcc cgcggccccg | 1440 |
| ccgggcctca ggcccgggga ccctcagcgc tacctttgc ctccggctct gggactgctc | 1500 |
| gtggccgcgg gcgtggccgg cgctgcgctc ttgctggtcc acgtgcgccg ccgtggccac | 1560 |
| tcccaggatg ctgggtctcg cttgctggct gggaccccgg agccgtcagt ccacgcactc | 1620 |
| ccggatgcac tcaacaacct aaggacgcag gagggttccg gggatggtcc gagctcgtcc | 1680 |
| gtagattgga atcgccctga agatgtagac cctcaaggga tttatgtcat atctgctcct | 1740 |
| tccatctacg ctcgggaggt agcgacgccc cttttccccc cgctacacac tgggcgcgct | 1800 |
| gggcagaggc agcacctgct ttttccctac ccttcctcga ttctgtccgt gaaatga | 1857 |

<210> SEQ ID NO 58
<211> LENGTH: 1758
<212> TYPE: DNA
<213> ORGANISM: Mus musculus

<400> SEQUENCE: 58

| | |
|---|---|
| atggtctctc tgcaggtgtc tccgcttcc cagacgctga tcctggcttt tcttcttcct | 60 |
| caggcactgc cagctggtgt cttcgagcta caaattcatt cttcgggcc aggcccaggc | 120 |
| ctcgggaccc cacgctcccc ctgcaacgcc cgaggccctt gccgcctctt cttcagggtc | 180 |
| tgcctgaagc ccggagtctc ccaggaggcc accgagtccc tgtgcgccct gggcgcagca | 240 |
| ctgagcacga gcgtcccggt ctatacggag caccccggag agtcagcggc tgccctgccg | 300 |
| ctgcctgatg gcctcgtacg tgtgcccttc cgcgatgctt ggccgggcac cttctccctc | 360 |
| gtcattgaaa cctggagaga gcagctggga gagcatgctg gagggcccgc ctggaacctg | 420 |

-continued

| | |
|---|---|
| ctagcacgtg tggtcggccg tagacgcctg gcggctgggg gcccgtgggc ccgcgatgtg | 480 |
| cagcgcacag gcacatggga gttgcacttc tcctaccgcg cgcggtgcga gccgcccgcc | 540 |
| gtcgggggccg cctgcgcgcg cctgtgccgc tcacgcagtg cccctcgcg gtgtggcccg | 600 |
| ggactgcgac cctgcacgcc attcccagac gagtgcgaag cccgtctgt gtgtcgacca | 660 |
| ggctgcagcc ccgagcacgg ctactgtgaa gagcctgatg aatgccgttg cctggagggc | 720 |
| tggactggac ccctctgcac ggtccctgtc tccaccagta gctgcctgaa ctccagggtt | 780 |
| cctggtcctg ccagcactgg atgccttta cctgggcctg gaccttgtga tgggaaccca | 840 |
| tgtgccaatg ggggcagctg tagtgaaacc tctggctcct ttgaatgtgc ctgtccccgg | 900 |
| ggattctacg ggcttcgatg tgaggtgagc ggggtcacgt gcgcagatgg accctgcttc | 960 |
| aatggcggct tgtgtgttgg cggtgaagat cctgactctg cctatgtctg tcattgccca | 1020 |
| cctggtttcc aaggctctaa ctgtgagaag agggtggacc gctgtagcct gcagccatgt | 1080 |
| cagaatggcg gcctctgcct ggacctgggc cacgcgttgc gctgccgctg tcgcgcggga | 1140 |
| ttcgccgggc cgcgctgcga gcacgacctg gacgactgcg ccggccgcgc ctgtgccaac | 1200 |
| ggcggcacgt gcgtggaggg cggcggctcg cgccgctgct cctgtgcgct gggcttcggc | 1260 |
| gggcgcgact gccgagaacg cgccgacccc tgcgcctccc gccctgcgc gcatggaggc | 1320 |
| cgttgctacg cccacttctc tggcctggtc tgcgcctgcg cgcccggcta catgggcgtg | 1380 |
| agatgcgagt cgctgtgcg cccggacggc gcggacgcgg tgcccgccgc ccgcggggc | 1440 |
| ctgaggcagg cggatccaca gcgctttctt ctgcctcccg ccttggggct gctggtggcc | 1500 |
| gccggtttgg ctggcgccgc actcttggtc atccacgttc gccgccgagg tcctggccag | 1560 |
| gataccggga ctcgcctgct ttctgggacc cgggagcctt cggtccacac gctcccggat | 1620 |
| gcactcaaca acctgaggtt acaagacggt gctggggatg gccccagttc gtcggctgac | 1680 |
| tggaatcatc ctgaagatgg agactctaga tccatttatg tcataccagc cccttccatt | 1740 |
| tatgcacgag aggcctga | 1758 |

<210> SEQ ID NO 59
<211> LENGTH: 2172
<212> TYPE: DNA
<213> ORGANISM: homo sapiens

<400> SEQUENCE: 59

| | |
|---|---|
| atgggcagtc ggtgcgcgct ggccctggcg gtgctctcgg ccttgctgtg tcaggtctgg | 60 |
| agctctgggg tgttcgaact gaagctgcag gagttcgtca acaagaaggg gctgctgggg | 120 |
| aaccgcaact gctgccgcgg gggcgcgggg ccaccgccgt gcgcctgccg gaccttcttc | 180 |
| cgcgtgtgcc tcaagcacta ccaggccagc gtgtcccccg agccgccctg cacctacggc | 240 |
| agcgccgtca cccccgtgct gggcgtcgac tccttcagtc tgcccgacgg cggggcgcc | 300 |
| gactccgcgt tcagcaaccc catccgcttc cccttcggct tcacctggcc gggcaccttc | 360 |
| tctctgatta ttgaagctct ccacacagat tctcctgatg acctcgcaac agaaaaccca | 420 |
| gaaagactca tcagccgcct ggccacccag aggcacctga cggtgggcga ggagtggtcc | 480 |
| caggacctgc acagcagcgg ccgcacggac ctcaagtact cctaccgctt cgtgtgtgac | 540 |
| gaacactact acgagaggg ctgctccgtt ttctgccgtc cccgggacga tgccttcggc | 600 |
| cacttcacct gtgggagcg tggggagaaa tgtgcaacc ctggctggaa agggccctac | 660 |
| tgcacagagc cgatctgcct gcctggatgt gatgagcagc atggattttg tgacaaacca | 720 |

| | |
|---|---:|
| ggggaatgca agtgcagagt gggctggcag ggccggtact gtgacgagtg tatccgctat | 780 |
| ccaggctgtc tccatggcac ctgccagcag ccctggcagt gcaactgcca ggaaggctgg | 840 |
| gggggccttt tctgcaacca ggacctgaac tactgcacac accataagcc ctgcaagaat | 900 |
| ggagccacct gcaccaacac gggccagggg agctacactt gctcttgccg gcctgggtac | 960 |
| acaggtgcca cctgcgagct ggggattgac gagtgtgacc ccagcccttg taagaacgga | 1020 |
| gggagctgca cggatctcga aacagctac tcctgtacct gcccacccgg cttctacggc | 1080 |
| aaaatctgtg aattgagtgc catgacctgt gcggacggcc cttgctttaa cggggtcgg | 1140 |
| tgctcagaca gccccgatgg agggtacagc tgccgctgcc ccgtgggcta ctccggcttc | 1200 |
| aactgtgaga agaaaattga ctactgcagc tcttcaccct gttctaatgg tgccaagtgt | 1260 |
| gtggacctcg gtgatgccta cctgtgccgc tgccaggccg gcttctcggg gaggcactgt | 1320 |
| gacgacaacg tggacgactg cgcctcctcc ccgtgcgcca acggggcac ctgccgggat | 1380 |
| ggcgtgaacg acttctcctg cacctgcccg cctggctaca cgggcaggaa ctgcagtgcc | 1440 |
| cccgtcagca ggtgcgagca cgcacccctgc cacaatgggg ccacctgcca cgagagggc | 1500 |
| caccgctatg tgtgcgagtg tgcccgaggc tacgggggtc ccaactgcca gttcctgctc | 1560 |
| cccgagctgc ccccgggccc agcggtggtg gacctcactg agaagctaga ggccagggc | 1620 |
| gggccattcc cctgggtggc cgtgtgcgcc ggggtcatcc ttgtcctcat gctgctgctg | 1680 |
| ggctgtgccg ctgtggtggt ctgcgtccgg ctgaggctgc agaagcaccg gcccccagcc | 1740 |
| gaccccctgcc gggggagac ggagaccatg aacaacctgg ccaactgcca gcgtgagaag | 1800 |
| gacatctcag tcagcatcat cggggccacg cagatcaaga acaccaacaa gaaggcggac | 1860 |
| ttccacgggg accacagcgc cgacaagaat ggcttcaagg cccgctaccc agcggtggac | 1920 |
| tataacctcg tgcaggacct caagggtgac gacaccgccg tcaggacgc gcacagcaag | 1980 |
| cgtgacacca gtgccagcc ccagggctcc tcaggggagg agaaggggac cccgaccaca | 2040 |
| ctcaggggtg gagaagcatc tgaaagaaaa aggccggact cgggctgttc aacttcaaaa | 2100 |
| gacaccaagt accagtcggt gtacgtcata tccgaggaga aggatgagtg cgtcatagca | 2160 |
| actgaggtgt aa | 2172 |

<210> SEQ ID NO 60
<211> LENGTH: 7668
<212> TYPE: DNA
<213> ORGANISM: homo sapiens

<400> SEQUENCE: 60

| | |
|---|---:|
| atgccgccgc tcctggcgcc cctgctctgc ctggcgctgc tgcccgcgct cgccgcacga | 60 |
| ggcccgcgat gctcccagcc cggtgagacc tgcctgaatg cgggaagtg tgaagcggcc | 120 |
| aatggcacgg aggcctgcgt ctgtggcggg gccttcgtgg gcccgcgatg ccaggacccc | 180 |
| aacccgtgcc tcagcacccc ctgcaagaac gccgggacat gccacgtggt ggaccgcaga | 240 |
| ggcgtggcag actatgcctg cagctgtgcc ctggcttct ctgggcccct ctgcctgaca | 300 |
| cccctggaca atgcctgcct caccaaccc tgccgcaacg gggcacctg cgacctgctc | 360 |
| acgctgacga agtacaagtg ccgctgcccg cccggctggt cagggaaatc gtgccagcag | 420 |
| gctgacccgt gcgcctccaa cccctgcgcc aacggtggcc agtgcctgcc cttcgaggcc | 480 |
| tcctacatct gccactgcc acccagcttc catggcccca cctgccggca ggatgtcaac | 540 |
| gagtgtggcc agaagcccgg gctttgccgc cacgaaggca cctgccacaa cgaggtcggc | 600 |
| tcctaccgct gcgtctgccg cgccacccac actggcccca actgcgagcg gccctacgtg | 660 |

```
ccctgcagcc cctcgccctg ccagaacggg ggcacctgcc gccccacggg cgacgtcacc    720
cacgagtgtg cctgcctgcc aggcttcacc ggccagaact gtgaggaaaa tatcgacgat    780
tgtccaggaa acaactgcaa gaacgggggt gcctgtgtgg acggcgtgaa cacctacaac    840
tgccgctgcc cgccagagtg gacaggtcag tactgtaccg aggatgtgga cgagtgccag    900
ctgatgccaa atgcctgcca gaacggcggg acctgccaca cacccacggg tggctacaac    960
tgcgtgtgtg tcaacggctg gactggtgag gactgcagcg agaacattga tgactgtgcc   1020
agcgccgcct gcttccacgg cgccacctgc catgaccgtg tggcctcctt ctactgcgag   1080
tgtccccatg gccgcacagg tctgctgtgc cacctcaacg acgcatgcat cagcaacccc   1140
tgtaacgagg gctccaactg cgacaccaac cctgtcaatg gcaaggccat ctgcacctgc   1200
ccctcggggt acacgggccc ggcctgcagc caggacgtgg atgagtgctc gctgggtgcc   1260
aacccctgcg agcatgcggg caagtgcatc aacacgctgg gctccttcga gtgccagtgt   1320
ctgcagggct acacgggccc ccgatgcgag atcgacgtca acgagtgcgt ctcgaacccg   1380
tgccagaacg acgccacctg cctggaccag attggggagt ccagtgcat ctgcatgccc    1440 ggctacgagg tgtgcactg cgaggtcaac acagacgagt gtgccagcag cccctgcctg    1500
cacaatggcc gctgcctgga caagatcaat gagttccagt gcgagtgccc cacgggcttc   1560
actgggcatc tgtgccagta cgatgtggac gagtgtgcca gcacccctg caagaatggt   1620 gccaagtgcc tggacggacc caacacttac acctgtgtgt gcacggaagg gtacacgggg   1680
acgcactgcg aggtggacat cgatgagtgc gaccccgacc cctgccacta cggctcctgc   1740
aaggacggcg tcgccacctt cacctgcctc tgccgcccag gctacacggg ccaccactgc   1800
gagaccaaca tcaacgagtg ctccagccag ccctgccgcc acgggggcac ctgccaggac   1860
cgcgacaacg cctacctctg cttctgcctg aaggggacca caggacccaa ctgcgagatc   1920
aacctggatg actgtgccag cagcccctg gactcgggca cctgtctgga caagatcgat   1980
ggctacgagt gtgcctgtga gccgggctac acagggagca tgtgtaacat caacatcgat   2040
gagtgtgcgg gcaaccccctg ccacaacggg ggcacctgcg aggacggcat caatggcttc   2100
acctgccgct gccccgaggg ctaccacgac cccacctgcc tgtctgaggt caatgagtgc   2160
aacagcaacc cctgcgtcca cggggcctgc cgggacagcc tcaacgggta caagtgcgac   2220
tgtgaccctg ggtggagtgg gaccaactgt gacatcaaca acaatgagtg tgaatccaac   2280
ccttgtgtca acggcggcac ctgcaaagac atgaccagtg gctacgtgtg cacctgccgg   2340
gagggcttca gcgtcccaa ctgccagacc aacatcaacg agtgtcgtc caacccatgt    2400 ctgaaccagg gcacgtgtat tgacgacgtt gccgggtaca agtgcaactg cctgctgccc   2460
tacacaggtg ccacgtgtga ggtggtgctg gccccgtgtg cccccagccc ctgcagaaac   2520 ggcgggagt gcaggcaatc cgaggactat gagagcttct cctgtgtctg ccccacgggc   2580
tggcaagggc agacctgtga ggtcgacatc aacgagtgcg ttctgagccc gtgccggcac   2640
ggcgcatcct gccagaacac ccacggcggc taccgctgcc actgccaggc cggctacagt   2700
gggcgcaact gcgagaccga catcgacgac tgccggccca acccgtgtca acggggggc   2760 tcctgcacag acgccatcaa cacggccttc tgcgactgcc tgcccggctt ccggggcact   2820
ttctgtgagg aggacatcaa cgagtgtgcc agtgaccct gccgcaacgg ggccaactgc   2880
acggactgcg tggacagcta cacgtgcacc tgccccgcag gcttcagcgg gatccactgt   2940
gagaacaaca cgcctgactg cacagagagc tcctgcttca acggtggcac ctgcgtggac   3000
```

```
ggcatcaact cgttcacctg cctgtgtcca cccggcttca cgggcagcta ctgccagcac    3060
gatgtcaatg agtgcgactc acagccctgc ctgcatggcg gcacctgtca ggacggctgc    3120
ggctcctaca ggtgcacctg ccccagggc tacactggcc ccaactgcca gaaccttgtg     3180
cactggtgtg actcctcgcc ctgcaagaac ggcggcaaat gctggcagac ccacacccag    3240
taccgctgcg agtgccccag cggctggacc ggcctttact gcgacgtgcc cagcgtgtcc    3300
tgtgaggtgg ctgcgcagcg acaaggtgtt gacgttgccc gcctgtgcca gcatggaggg    3360
ctctgtgtgg acgcgggcaa cacgcaccac tgccgctgcc aggcgggcta cacaggcagc    3420
tactgtgagg acctggtgga cgagtgctca cccagcccct gccagaacgg ggccacctgc    3480
acggactacc tgggcggcta ctcctgcaag tgcgtggccg gctaccacgg ggtgaactgc    3540
tctgaggaga tcgacgagtg cctctcccac ccctgccaga cgggggcac ctgcctcgac     3600 ctccccaaca cctacaagtg ctcctgccca cggggcactc agggtgtgca ctgtgagatc    3660
aacgtggacg actgcaatcc ccccgttgac cccgtgtccc ggagcccaa gtgctttaac     3720 aacggcacct gcgtggacca ggtgggcggc tacagctgca cctgcccgcc gggcttcgtg    3780
ggtgagcgct gtgaggggga tgtcaacgag tgcctgtcca atccctgcga cgcccgtggc    3840
acccagaact gcgtgcagcg cgtcaatgac ttccactgcg agtgccgtgc tggtcacacc    3900
gggcgccgct gcgagtccgt catcaatggc tgcaaaggca agccctgcaa gaatggggc    3960 acctgcgccg tggcctccaa caccgcccgc gggttcatct gcaagtgccc tgcgggcttc    4020
gagggcgcca cgtgtgagaa tgacgctcgt acctgcggca gcctgcgctg cctcaacggc    4080
ggcacatgca tctccggccc cgcgcagccc acctgcctgt gcctgggccc cttcacgggc    4140
cccgaatgcc agttcccggc cagcagcccc tgcctgggcg gcaacccctg ctacaaccag    4200
gggacctgtg agcccacatc cgagagcccc ttctaccgtt gcctgtgccc cgccaaattc    4260
aacgggctct tgtgccacat cctggactac agcttcgggg gtggggccgg gcgcgacatc    4320
cccccgccgc tgatcgagga ggcgtgcgag ctgcccgagt gccaggagga cgcgggcaac    4380
aaggtctgca gcctgcagtg caacaaccac gcgtgcggct gggacggcgg tgactgctcc    4440
ctcaacttca atgacccctg gaagaactgc acgcagtctc tgcagtgctg gaagtacttc    4500
agtgacggcc actgtgacag ccagtgcaac tcagccggct gcctcttcga cggctttgac    4560
tgccagcgtg cggaaggcca gtgcaaccc ctgtacgacc agtactgcaa ggaccacttc     4620
agcgacgggc actgcgacca gggctgcaac agcgcggagt gcgagtggga cgggctggac    4680
tgtgcggagc atgtacccga gaggctggcg gccggcacgc tggtggtggt ggtgctgatg    4740
ccgccggagc agctgcgcaa cagctccttc cacttcctgc gggagctcag ccgcgtgctg    4800
cacaccaacg tggtcttcaa gcgtgacgca cacggccagc agatgatctt ccctactac    4860 ggccgcgagg aggagctgcg caagcacccc atcaagcgtg ccgccgaggg ctgggccgca    4920
cctgacgccc tgctgggcca ggtgaaggcc tcgctgctcc ctggtggcag cgagggtggg    4980
cggcggcgga gggagctgga ccccatggac gtccgcggct ccatcgtcta cctggagatt    5040
gacaaccggc agtgtgtgca ggcctcctcg cagtgcttcc agagtgccac cgacgtggcc    5100
gcattcctgg agcgctcgct ctcgctgggc agcctcaaca tcccctacaa gatcgaggcc    5160
gtgcagagtg agaccgtgga gccgcccccg ccggcgcagc tgcacttcat gtacgtggcg    5220
gcggccgcct ttgtgcttct gttcttcgtg ggctgcgggg tgctgctgtc ccgcaagcgc    5280
cggcggcagc atgccagct ctggttccct gagggcttca aagtgtctga ggccagcaag    5340
aagaagcggc gggagcccct cggcgaggac tccgtgggcc tcaagcccct gaagaacgct    5400
```

```
tcagacggtg ccctcatgga cgacaaccag aatgagtggg gggacgagga cctggagacc   5460
aagaagttcc ggttcgagga gcccgtggtt ctgcctgacc tggacgacca gacagaccac   5520
cggcagtgga ctcagcagca cctggatgcc gctgacctgc gcatgtctgc catggccccc   5580
acaccgcccc agggtgaggt tgacgccgac tgcatggacg tcaatgtccg cgggcctgat   5640
ggcttcaccc cgctcatgat cgcctcctgc agcggggggcg gcctggagac gggcaacagc   5700
gaggaagagg aggacgcgcc ggccgtcatc tccgacttca tctaccaggg cgccagcctg   5760
cacaaccaga cagaccgcac gggcgagacc gccttgcacc tggccgcccg ctactcacgc   5820
tctgatgccg ccaagcgcct gctggaggcc agcgcagatg ccaacatcca ggacaacatg   5880
ggccgcaccc cgctgcatgc ggctgtgtct gccgacgcac aaggtgtctt ccagatcctg   5940
atccggaacc gagccacaga cctggatgcc cgcatgcatg atggcacgac gccactgatc   6000
ctggctgccc gcctggccgt ggagggcatg ctggaggacc tcatcaactc acacgccgac   6060
gtcaacgccg tagatgacct gggcaagtcc gccctgcact gggccgccgc cgtgaacaat   6120
gtggatgccg cagttgtgct cctgaagaac ggggctaaca agatatgca gaacaacagg    6180 gaggagacac ccctgtttct ggccgcccgg gagggcagct acgagaccgc caaggtgctg   6240
ctggaccact ttgccaaccg ggacatcacg gatcatatgg accgcctgcc gcgcgacatc   6300
gcacaggagc gcatgcatca cgacatcgtg aggctgctgg acgagtacaa cctggtgcgc   6360
agcccgcagc tgcacggagc cccgctgggg ggcacgccca cctgtcgcc ccgctctgc    6420 tcgcccaacg gctacctggg cagcctcaag cccggcgtgc agggcaagaa ggtccgcaag   6480
cccagcagca aaggcctggc ctgtggaagc aaggaggcca aggacctcaa ggcacggagg   6540
aagaagtccc aggacggcaa gggctgcctg ctggacagct ccggcatgct ctcgcccgtg   6600
gactccctgg agtcacccca tggctacctg tcagacgtgg cctcgccgcc actgctgccc   6660
tccccgttcc agcagtctcc gtccgtgccc ctcaaccacc tgcctgggat gcccgacacc   6720
cacctgggca tcgggcacct gaacgtggcg gccaagcccg agatggcggc gctgggtggg   6780
ggcggccggc tggcctttga gactggccca cctcgtctct cccacctgcc tgtggcctct   6840
ggcaccagca ccgtcctggg ctccagcagc ggaggggccc tgaatttcac tgtgggcggg   6900
tccaccagtt tgaatggtca atgcgagtgg ctgtcccggc tgcagagcgg catggtgccg   6960
aaccaataca ccctctgcg ggggagtgtg caccaggcc cctgagcac acaggccccc     7020 tccctgcagc atggcatggt aggcccgctg cacagtagcc ttgctgccag cgccctgtcc   7080
cagatgatga gctaccaggg cctgcccagc acccggctgg ccacccagcc tcacctggtg   7140
cagacccagc aggtgcagcc acaaaactta cagatgcagc agcagaacct gcagccagca   7200
aacatccagc agcagcaaag cctgcagccg ccaccaccac caccacagcc gcaccttggc   7260
gtgagctcag cagccagcgg ccacctgggc cggagcttcc tgagtggaga gccgagccag   7320
gcagacgtgc agccactggg ccccagcagc ctggcggtgc acactattct gccccaggag   7380
agccccgccc tgcccacgtc gctgccatcc tcgctggtcc cacccgtgac cgcagcccag   7440
ttcctgacgc ccccctcgca gcacagctac tcctcgcctg tggacaacac ccccagccac   7500
cagctacagg tgcctgagca ccccttcctc acccgtcc ctgagtcccc tgaccagtgg     7560
tccagctcgt ccccgcattc caacgtctcc gactggtccg agggcgtctc cagccctccc   7620
accagcatgc agtcccagat cgcccgcatt ccggaggcct tcaagtaa               7668
```

<210> SEQ ID NO 61

```
<211> LENGTH: 4
<212> TYPE: PRT
<213> ORGANISM: artificial
<220> FEATURE:
<223> OTHER INFORMATION: artificial linker

<400> SEQUENCE: 61

Gly Gly Gly Ser
1

<210> SEQ ID NO 62
<211> LENGTH: 4
<212> TYPE: PRT
<213> ORGANISM: artificial
<220> FEATURE:
<223> OTHER INFORMATION: artificial linker

<400> SEQUENCE: 62

Ser Gly Gly Gly
1

<210> SEQ ID NO 63
<211> LENGTH: 5
<212> TYPE: PRT
<213> ORGANISM: artificial
<220> FEATURE:
<223> OTHER INFORMATION: artificial linker

<400> SEQUENCE: 63

Gly Gly Gly Gly Ser
1               5

<210> SEQ ID NO 64
<211> LENGTH: 5
<212> TYPE: PRT
<213> ORGANISM: artificial
<220> FEATURE:
<223> OTHER INFORMATION: artificial linker

<400> SEQUENCE: 64

Ser Gly Gly Gly Gly
1               5

<210> SEQ ID NO 65
<211> LENGTH: 6
<212> TYPE: PRT
<213> ORGANISM: artificial
<220> FEATURE:
<223> OTHER INFORMATION: artificial linker

<400> SEQUENCE: 65

Gly Gly Gly Gly Gly Ser
1               5

<210> SEQ ID NO 66
<211> LENGTH: 6
<212> TYPE: PRT
<213> ORGANISM: artificial
<220> FEATURE:
<223> OTHER INFORMATION: artificial linker

<400> SEQUENCE: 66

Ser Gly Gly Gly Gly Gly
1               5

<210> SEQ ID NO 67
<211> LENGTH: 7
```

```
<212> TYPE: PRT
<213> ORGANISM: artificial
<220> FEATURE:
<223> OTHER INFORMATION: artificial linker

<400> SEQUENCE: 67

Gly Gly Gly Gly Gly Ser
1               5

<210> SEQ ID NO 68
<211> LENGTH: 7
<212> TYPE: PRT
<213> ORGANISM: artificial
<220> FEATURE:
<223> OTHER INFORMATION: artificial linker

<400> SEQUENCE: 68

Ser Gly Gly Gly Gly Gly Gly
1               5

<210> SEQ ID NO 69
<211> LENGTH: 475
<212> TYPE: PRT
<213> ORGANISM: Mus musculus

<400> SEQUENCE: 69

Met Glu Trp Ser Gly Val Phe Ile Phe Leu Leu Ser Val Thr Ala Gly
1               5                   10                  15

Val His Ser Gln Val Gln Leu Gln Gln Ser Gly Ala Asp Leu Val Arg
            20                  25                  30

Pro Gly Thr Ser Val Lys Val Ser Cys Lys Ala Ser Gly Tyr Ala Phe
        35                  40                  45

Thr Asn Tyr Leu Ile Glu Trp Ile Lys Gln Arg Pro Gly Gln Gly Leu
    50                  55                  60

Glu Trp Ile Gly Val Met Asn Pro Gly Ser Gly Gly Thr His Tyr Ser
65                  70                  75                  80

Glu Lys Phe Arg Gly Lys Ala Thr Leu Thr Ala Asp Lys Ser Ser Ser
                85                  90                  95

Thr Ala Tyr Met Gln Leu Ile Ser Leu Thr Ser Asp Asp Ser Ala Val
            100                 105                 110

Tyr Phe Cys Ala Arg Ser Asp Tyr Asp Tyr Val Thr Tyr Ala Met Asp
        115                 120                 125

Tyr Trp Gly Gln Gly Thr Ser Val Thr Val Ser Ser Ala Lys Thr Thr
    130                 135                 140

Ala Pro Ser Val Tyr Pro Leu Ala Pro Val Cys Gly Gly Thr Thr Gly
145                 150                 155                 160

Ser Ser Val Thr Leu Gly Cys Leu Val Lys Gly Tyr Phe Pro Glu Pro
                165                 170                 175

Val Thr Leu Thr Trp Asn Ser Gly Ser Leu Ser Ser Gly Val His Thr
            180                 185                 190

Phe Pro Ala Leu Leu Gln Ser Gly Leu Tyr Thr Leu Ser Ser Ser Val
        195                 200                 205

Thr Val Thr Ser Asn Thr Trp Pro Ser Gln Thr Ile Thr Cys Asn Val
    210                 215                 220

Ala His Pro Ala Ser Ser Thr Lys Val Asp Lys Lys Ile Glu Pro Arg
225                 230                 235                 240

Val Pro Ile Thr Gln Asn Pro Cys Pro Pro Leu Lys Glu Cys Pro Pro
                245                 250                 255
```

-continued

```
Cys Ala Ala Pro Asp Leu Leu Gly Gly Pro Ser Val Phe Ile Phe Pro
            260                 265                 270
Pro Lys Ile Lys Asp Val Leu Met Ile Ser Leu Ser Pro Met Val Thr
        275                 280                 285
Cys Val Val Val Asp Val Ser Glu Asp Asp Pro Asp Val Gln Ile Ser
    290                 295                 300
Trp Phe Val Asn Asn Val Glu Val His Thr Ala Gln Thr Gln Thr His
305                 310                 315                 320
Arg Glu Asp Tyr Asn Ser Thr Leu Arg Val Val Ser Ala Leu Pro Ile
                325                 330                 335
Gln His Gln Asp Trp Met Ser Gly Lys Glu Phe Lys Cys Lys Val Asn
            340                 345                 350
Asn Arg Ala Leu Pro Ser Pro Ile Glu Lys Thr Ile Ser Lys Pro Arg
        355                 360                 365
Gly Pro Val Arg Ala Pro Gln Val Tyr Val Leu Pro Pro Pro Ala Glu
    370                 375                 380
Glu Met Thr Lys Lys Glu Phe Ser Leu Thr Cys Met Ile Thr Gly Phe
385                 390                 395                 400
Leu Pro Ala Glu Ile Ala Val Asp Trp Thr Ser Asn Gly Arg Thr Glu
                405                 410                 415
Gln Asn Tyr Lys Asn Thr Ala Thr Val Leu Asp Ser Asp Gly Ser Tyr
            420                 425                 430
Phe Met Tyr Ser Lys Leu Arg Val Gln Lys Ser Thr Trp Glu Arg Gly
        435                 440                 445
Ser Leu Phe Ala Cys Ser Val Val His Glu Gly Leu His Asn His Leu
    450                 455                 460
Thr Thr Lys Thr Ile Ser Arg Ser Leu Gly Lys
465                 470                 475

<210> SEQ ID NO 70
<211> LENGTH: 472
<212> TYPE: PRT
<213> ORGANISM: Mus musculus

<400> SEQUENCE: 70

Met Gly Trp Ser Trp Ile Phe Leu Phe Leu Leu Ser Gly Thr Gly Gly
1               5                   10                  15
Val Leu Ser Glu Val Gln Leu Gln Gln Ser Gly Pro Glu Leu Val Lys
            20                  25                  30
Pro Gly Ala Ser Val Lys Met Ser Cys Arg Ala Ser Gly Tyr Thr Phe
        35                  40                  45
Thr Asp Tyr Tyr Met Lys Trp Val Lys Gln Ser His Gly Lys Ser Leu
    50                  55                  60
Glu Trp Ile Gly Asp Ile Asn Pro Asn Asn Gly Asp Thr Phe Tyr Asn
65                  70                  75                  80
Gln Lys Phe Lys Gly Lys Ala Thr Leu Thr Ile Asp Lys Ser Ser Ser
                85                  90                  95
Thr Ala Tyr Met Gln Leu Asn Ser Leu Thr Ser Asp Asp Ser Ala Val
            100                 105                 110
Tyr Tyr Cys Ala Arg Asp Gly Asn Tyr Ala Tyr Phe Tyr Trp Gly
        115                 120                 125
Gln Gly Thr Thr Leu Thr Val Ser Ser Ala Lys Thr Thr Ala Pro Ser
    130                 135                 140
Val Tyr Pro Leu Ala Pro Val Cys Gly Gly Thr Thr Gly Ser Ser Val
145                 150                 155                 160
```

```
Thr Leu Gly Cys Leu Val Lys Gly Tyr Phe Pro Glu Pro Val Thr Leu
                165                 170                 175
Thr Trp Asn Ser Gly Ser Leu Ser Ser Gly Val His Thr Phe Pro Ala
            180                 185                 190
Leu Leu Gln Ser Gly Leu Tyr Thr Leu Ser Ser Val Thr Val Thr
        195                 200                 205
Ser Asn Thr Trp Pro Ser Gln Thr Ile Thr Cys Asn Val Ala His Pro
210                 215                 220
Ala Ser Ser Thr Lys Val Asp Lys Lys Ile Glu Pro Arg Val Pro Ile
225                 230                 235                 240
Thr Gln Asn Pro Cys Pro Pro Leu Lys Glu Cys Pro Pro Cys Ala Ala
                245                 250                 255
Pro Asp Leu Leu Gly Gly Pro Ser Val Phe Ile Phe Pro Pro Lys Ile
                260                 265                 270
Lys Asp Val Leu Met Ile Ser Leu Ser Pro Met Val Thr Cys Val Val
                275                 280                 285
Val Asp Val Ser Glu Asp Asp Pro Asp Val Gln Ile Ser Trp Phe Val
                290                 295                 300
Asn Asn Val Glu Val His Thr Ala Gln Thr Gln Thr His Arg Glu Asp
305                 310                 315                 320
Tyr Asn Ser Thr Leu Arg Val Val Ser Ala Leu Pro Ile Gln His Gln
                325                 330                 335
Asp Trp Met Ser Gly Lys Glu Phe Lys Cys Lys Val Asn Asn Arg Ala
                340                 345                 350
Leu Pro Ser Pro Ile Glu Lys Thr Ile Ser Lys Pro Arg Gly Pro Val
                355                 360                 365
Arg Ala Pro Gln Val Tyr Val Leu Pro Pro Pro Ala Glu Glu Met Thr
370                 375                 380
Lys Lys Glu Phe Ser Leu Thr Cys Met Ile Thr Gly Phe Leu Pro Ala
385                 390                 395                 400
Glu Ile Ala Val Asp Trp Thr Ser Asn Gly Arg Thr Glu Gln Asn Tyr
                405                 410                 415
Lys Asn Thr Ala Thr Val Leu Asp Ser Asp Gly Ser Tyr Phe Met Tyr
                420                 425                 430
Ser Lys Leu Arg Val Gln Lys Ser Thr Trp Glu Arg Gly Ser Leu Phe
                435                 440                 445
Ala Cys Ser Val Val His Glu Gly Leu His Asn His Leu Thr Thr Lys
450                 455                 460
Thr Ile Ser Arg Ser Leu Gly Lys
465                 470

<210> SEQ ID NO 71
<211> LENGTH: 477
<212> TYPE: PRT
<213> ORGANISM: Mus musculus

<400> SEQUENCE: 71

Met Lys Leu Trp Leu Asn Trp Ile Phe Leu Val Thr Leu Leu Asn Gly
1               5                   10                  15
Ile Gln Cys Glu Val Lys Leu Val Glu Ser Gly Gly Gly Leu Val Gln
                20                  25                  30
Pro Gly Gly Ser Leu Ser Leu Ser Cys Ala Ala Ser Gly Phe Thr Phe
            35                  40                  45
Thr Asp Tyr Tyr Met Asn Trp Val Arg Gln Pro Pro Gly Lys Ala Leu
```

-continued

```
            50                  55                  60
Glu Trp Leu Ala Leu Ile Arg Asn Lys Ala Asn Gly Tyr Thr Thr Glu
 65                  70                  75                  80

Tyr Asn Ala Ser Val Lys Gly Arg Phe Thr Ile Ser Arg Asp Asn Ser
                 85                  90                  95

Gln Asn Ile Leu Tyr Leu Gln Met Asn Ala Leu Arg Ala Glu Asp Ser
                100                 105                 110

Ala Thr Tyr Tyr Cys Ala Arg Asp Ser Asp Gly Tyr Tyr Glu Tyr Tyr
            115                 120                 125

Phe Asp Tyr Trp Gly Gln Gly Thr Thr Leu Thr Val Ser Ser Ala Lys
        130                 135                 140

Thr Thr Ala Pro Ser Val Tyr Pro Leu Ala Pro Val Cys Gly Gly Thr
145                 150                 155                 160

Thr Gly Ser Ser Val Thr Leu Gly Cys Leu Val Lys Gly Tyr Phe Pro
                165                 170                 175

Glu Pro Val Thr Leu Thr Trp Asn Ser Gly Ser Leu Ser Ser Gly Val
                180                 185                 190

His Thr Phe Pro Ala Leu Leu Gln Ser Gly Leu Tyr Thr Leu Ser Ser
            195                 200                 205

Ser Val Thr Val Thr Ser Asn Thr Trp Pro Ser Gln Thr Ile Thr Cys
        210                 215                 220

Asn Val Ala His Pro Ala Ser Ser Thr Lys Val Asp Lys Lys Ile Glu
225                 230                 235                 240

Pro Arg Val Pro Ile Thr Gln Asn Pro Cys Pro Pro Leu Lys Glu Cys
                245                 250                 255

Pro Pro Cys Ala Ala Pro Asp Leu Leu Gly Gly Pro Ser Val Phe Ile
                260                 265                 270

Phe Pro Pro Lys Ile Lys Asp Val Leu Met Ile Ser Leu Ser Pro Met
            275                 280                 285

Val Thr Cys Val Val Val Asp Val Ser Glu Asp Asp Pro Asp Val Gln
        290                 295                 300

Ile Ser Trp Phe Val Asn Asn Val Glu Val His Thr Ala Gln Thr Gln
305                 310                 315                 320

Thr His Arg Glu Asp Tyr Asn Ser Thr Leu Arg Val Val Ser Ala Leu
                325                 330                 335

Pro Ile Gln His Gln Asp Trp Met Ser Gly Lys Glu Phe Lys Cys Lys
                340                 345                 350

Val Asn Asn Arg Ala Leu Pro Ser Pro Ile Glu Lys Thr Ile Ser Lys
            355                 360                 365

Pro Arg Gly Pro Val Arg Ala Pro Gln Val Tyr Val Leu Pro Pro Pro
        370                 375                 380

Ala Glu Glu Met Thr Lys Lys Glu Phe Ser Leu Thr Cys Met Ile Thr
385                 390                 395                 400

Gly Phe Leu Pro Ala Glu Ile Ala Val Asp Trp Thr Ser Asn Gly Arg
                405                 410                 415

Thr Glu Gln Asn Tyr Lys Asn Thr Ala Thr Val Leu Asp Ser Asp Gly
                420                 425                 430

Ser Tyr Phe Met Tyr Ser Lys Leu Arg Val Gln Lys Ser Thr Trp Glu
            435                 440                 445

Arg Gly Ser Leu Phe Ala Cys Ser Val Val His Glu Gly Leu His Asn
        450                 455                 460
```

```
His Leu Thr Thr Lys Thr Ile Ser Arg Ser Leu Gly Lys
465                 470                 475
```